(12) United States Patent
Betschart et al.

(10) Patent No.: US 8,039,455 B2
(45) Date of Patent: Oct. 18, 2011

(54) MACROCYCLIC COMPOUNDS USEFUL AS BACE INHIBITORS

(75) Inventors: Claudia Betschart, Basel (CH); Manuel Koller, Schliern (CH); Kurt Laumen, March (DE); Andreas Lerchner, Binningen (CH); Rainer Machauer, Freiburg (DE); Clive McCarthy, Basel (CH); Marina Tintelnot-Blomley, Maulburg (DE); Siem Jacob Veenstra, Lorrach (DE)

(73) Assignee: Novartis AG, Basel (CH)

( * ) Notice: Subject to any disclaimer, the term of this patent is extended or adjusted under 35 U.S.C. 154(b) by 345 days.

(21) Appl. No.: 12/159,742

(22) PCT Filed: Dec. 28, 2006

(86) PCT No.: PCT/EP2006/012569
§ 371 (c)(1),
(2), (4) Date: Jun. 30, 2008

(87) PCT Pub. No.: WO2007/077004
PCT Pub. Date: Jul. 12, 2007

(65) Prior Publication Data
US 2009/0029960 A1    Jan. 29, 2009

(30) Foreign Application Priority Data
Dec. 30, 2005  (GB) .................................. 0526614.3

(51) Int. Cl.
*C07D 245/04* (2006.01)
*A61K 31/33* (2006.01)
(52) U.S. Cl. ........ 514/183; 514/290; 514/291; 514/292; 514/293; 540/456; 540/460; 540/461
(58) Field of Classification Search ............. 514/183, 514/290, 291, 292, 293; 540/456, 460, 461
See application file for complete search history.

(56) References Cited

U.S. PATENT DOCUMENTS

| 6,969,709 | B2 * | 11/2005 | Pulley et al. ............... 514/183 |
| 7,612,055 | B2 | 11/2009 | Auberson et al. |
| 2008/0132477 | A1 | 6/2008 | Betschart et al. |
| 2008/0214526 | A1 | 9/2008 | Lerchner et al. |
| 2010/0010025 | A1 | 1/2010 | Duthaler et al. |

FOREIGN PATENT DOCUMENTS

| WO | WO 02/100399 A1 | 12/2002 |
| WO | WO 02/100856 A1 | 12/2002 |
| WO | WO 2005/003106 A1 | 1/2005 |
| WO | WO 2005/016876 A2 | 2/2005 |
| WO | WO 2005/018545 A2 | 3/2005 |
| WO | WO 2005/049585 A1 | 6/2005 |
| WO | WO 2006/074940 A2 | 7/2006 |
| WO | WO 2006/074950 A1 | 7/2006 |
| WO | 2008/009734 A1 | 1/2008 |
| WO | 2008/009750 A2 | 1/2008 |

* cited by examiner

*Primary Examiner* — Bruck Kifle

(57) ABSTRACT

The invention relates to novel macrocyclic compounds of the formula (I)

in which all of the variables are as defined in the specification, in free base form or in acid addition salt form, to their preparation, to their use as medicaments and to medicaments comprising them.

3 Claims, No Drawings

MACROCYCLIC COMPOUNDS USEFUL AS BACE INHIBITORS

This application is the National Stage of Application No. PCT/EP2006/012569, filed on Dec. 28, 2006, which claims benefit under 35 U.S.C. §119(a)-(d) or (f) or 365(b) of GB Application No. 0526614.3, filed Dec. 30, 2005, the contents of which are incorporated herein by reference in their entirety.

The present invention relates to novel macrocyclic compounds, to their preparation, to their use as medicaments and to medicaments comprising them.

More particularly the invention relates to a compound of the formula

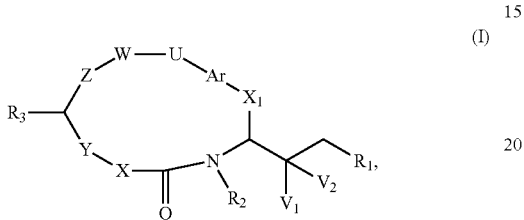

(I)

in which $R_1$ is $-(CH_2)_kN(R_a)R_b$, in which
  k is 0, 1 or 2;
  $R_a$ is hydrogen or an optionally substituted $(C_{1-8})$alkyl, $(C_{3-8})$cycloalkyl, $(C_{3-8})$cycloalkyl-$(C_{1-4})$alkyl, aryl, aryl$(C_{1-4})$alkyl, heteroaryl, heteroaryl$(C_{1-4})$alkyl, chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydro-quinol-4-yl, 1,2,3,4-tetrahydro-isoquinol-4-yl, 1,2,3,4-tetrahydro-naphth-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4dihydro-1H-1 lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl or 1,3,4,5-tetrahydro-benzo[c]oxepin-5-yl group; and
  $R_b$ is a $(C_{3-8})$cycloalkyl group, in which
    (a) one of the carbon ring members of the $(C_{3-8})$cycloalkyl moiety, which are different from the carbon ring member, to which the nitrogen atom carrying $R_a$ is attached, is optionally replaced by a hetero ring member, selected from the group consisting of $-O-$, $-S-$, $-S(=O)-$, $-S(=O)_2$ and $-N(R_c)-$, in which
      $R_c$ is hydrogen or an optionally substituted $(C_{1-8})$alkyl, $(C_{1-8})$cycloalkyl, $(C_{3-8})$cycloalkyl$(C_{1-4})$alkyl, aryl, aryl$(C_{1-4})$alkyl, heteroaryl or heteroaryl$(C_{1-4})$alkyl group,
    (b) the $(C_{3-8})$cycloalkyl moiety is substituted by 1 to 4 substituents, independently selected from the group consisting of halogen, cyano, oxo, hydroxy, $(C_{1-4})$-alkoxy, $(C_{1-4})$alkoxy$(C_{1-4})$alkoxy, $(C_{1-4})$alkylthio, $(C_{1-4})$alkylsulfinyl, $(C_{1-4})$alkylsulfonyl, $(C_{1-4})$alkylcarbonyl, $(C_{1-4})$alkylcarbonyloxy, $(C_{1-4})$alkoxycarbonyl, $(C_{1-4})$alkoxycarbonyloxy and an optionally substituted $(C_{1-8})$alkyl, $(C_{3-8})$cycloalkyl, $(C_{3-8})$cycloalkyl-$(C_{1-4})$alkyl, aryl, aryl$(C_{1-4})$alkyl, heteroaryl, heteroaryl$(C_{1-4})$alkyl, non-aromatic heterocyclyl, non-aromatic heterocyclyl$(C_{1-4})$alkyl, chroman-4-yl, isochromanyl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydro-quinol-4-yl, 1,2,3,4-tetrahydro-isoquinol-4-yl, 1,2,3,4-tetrahydro-naphth-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl or 1,3,4,5-tetrahydro-benzo[c]-oxepin-5-yl group, and
    (c) the $(C_{3-8})$cycloalkyl moiety is optionally substituted at two adjacent carbon ring members by two substituents, which form, together with the two adjacent carbon ring members, to which they are attached, a $(C_{3-8})$cycloalkyl group, in which
      (i) one of the carbon ring members of the $(C_{3-8})$cycloalkyl group thus formed, which are different from the said two adjacent carbon ring members, to which the said two substituents are optionally attached, is optionally replaced by a hetero ring member, selected from the group consisting of $-O-$, $-S-$, $-S(=O)-$, $-S(=O)_2-$ and $-N(R_d)-$, in which
        $R_d$ is hydrogen or an optionally substituted $(C_{1-8})$alkyl, $(C_{3-8})$cycloalkyl, $(C_{3-8})$cycloalkyl$(C_{1-4})$alkyl, aryl, aryl$(C_{1-4})$alkyl, heteroaryl or heteroaryl$(C_{1-4})$alkyl group, and
      (ii) the $(C_{3-8})$cycloalkyl group thus formed is optionally substituted by 1 to 4 substituents, independently selected from the group consisting of halogen, cyano, oxo, hydroxy, $(C_{1-4})$alkoxy, $(C_{1-4})$alkoxy$(C_{1-4})$alkoxy, $(C_{1-4})$alkylthio, $(C_{1-4})$alkylsulfinyl, $(C_{1-4})$alkylsulfonyl, $(C_{1-4})$alkylcarbonyl, $(C_{1-4})$alkylcarbonyloxy, $(C_{1-4})$alkoxycarbonyl, $(C_{1-4})$alkoxycarbonyloxy and an optionally substituted $(C_{1-8})$alkyl, $(C_{3-8})$cycloalkyl, $(C_{3-8})$cycloalkyl$(C_{1-4})$alkyl, aryl, aryl$(C_{1-4})$alkyl, heteroaryl, heteroaryl$(C_{1-4})$alkyl, non-aromatic heterocyclyl, non-aromatic heterocyclyl$(C_{1-4})$alkyl, chroman-4-yl, isochroman-4-yl, thiochroman-4-yl, isothiochroman-4-yl, 1,1-dioxo-1lambda*6*-thio-chroman-4-yl, 2,2-dioxo-2lambda*6*-isothiochroman-4-yl, 1,2,3,4-tetrahydro-quinol-4-yl, 1,2,3,4-tetrahydro-isoquinol-4 yl, 1,2,3,4-tetrahydro-naphth-1-yl, 1,1-dioxo-1,2,3,4-tetrahydro-1lambda*6*-benzo[e][1,2]thiazin-4-yl, 2,2-dioxo-1,2,3,4-tetra-hydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]-oxathiin-4-yl, 2,3,4,5-tetrahydro-benzo[b]oxepin-5-yl or 1,3,4,5-tetrahydro-benzo[c]-oxepin-5-yl group;

$R_2$ is hydrogen or $(C_{1-4})$alkyl;
$R_3$ is hydrogen, $(C_{1-6})$alkyl or an optionally substituted $(C_{1-6})$alkylOC(=O)NH, $(C_{3-8})$cyclo-alkylOC(=O)NH, $(C_{3-8})$cycloalkyl$(C_{1-4})$alkylOC(=O)NH, aryl$(C_{1-4})$alkylOC(=O)NH, heteroaryl$(C_{1-4})$alkylOC(=O)NH, $(C_{1-4})$alkylC(=O)NH, $(C_{3-8})$cycloalkylC(=O)NH, arylC(=O)NH, aryl$(C_{1-4})$alkylC(=O)NH, heteroarylC(=O)NH or heteroaryl$(C_{1-4})$al-kylC(=O)NH group;
Ar is an arylene or heteroarylene ring, which ring is optionally substituted with halogen, $(C_{1-4})$alkoxy, hydroxy or $(C_{1-4})$alkyl, whereby U and $X_1$ are in ortho- or meta-position to each other;

U is a bond, O, $CF_2$, $CF_2CF_2$, CHF, CHFCHF, cycloprop-1,2-ylene, $(C_{1-3})$alkylenoxy, $(C_{1-3})$alkylenamino, $(C_{1-8})$alkylene or $NR_e$, in which
  $R_e$ is hydrogen, $(C_{1-8})$alkyl or $(C_{3-8})$cycloalkyl;
either
$V_1$ is hydrogen and
$V_2$ is hydroxy
or
$V_1$ and $V_2$ together are oxo;
W is CH=CH, cycloprop-1,2-ylene, phen-1,2-ylene, $CH_2CH(OH)$, $CH(OH)CH_2$ or $CR_fR_fCR_fR_f$, in which
  each $R_f$, independently, is hydrogen, fluorine or $(C_{1-4})$alkyl;
X is an optionally substituted $(C_{1-4})$alkanylylidene, $(C_{1-4})$alkylene, $(C_{3-8})$cycloalkylene, piperidin-diyl, pyrrolidin-diyl, benzothiazole-4,6-diyl, benzoxazole-4,6-diyl, 1H-benzotriazole-4,6-diyl, imidazo[1,2-a]pyridine-6,8-diyl, benzo[1,2,5]oxadiazole-4,6-diyl, benzo[1,2,5]thiadiazole-4,6-diyl, 1H-indole-5,7-diyl, 1H-indole-4,6-diyl, 1H-benzimidazole-4,6-diyl or 1H-indazole-1,6-diyl group or an optionally substituted arylene or heteroarylene ring, whereby Y and C(=O)NR₂ are in meta-position to each other;
$X_1$ is $CR_gR_g$, in which
  each $R_g$, independently, is hydrogen, fluorine or an optionally substituted $(C_{1-8})$alkyl, $(C_{1-4})$alkoxy$(C_{1-4})$alkyl, $(C_{3-8})$cycloalkyl or $(C_{3-8})$cycloalkyl$(C_{1-4})$alkyl group;
Y is a bond, O, S(=O)₂, S(=O)₂NR$_h$, N(R$_h$)S(=O)₂, NR$_h$, C(R$_h$)OH, C(=O)NR$_h$, N(R$_h$)C(=O), C(=O)N(R$_h$)O or ON(R$_h$)C(=O), in which
  $R_h$ is hydrogen, $(C_{1-8})$alkyl or (C=)cycloalkyl; and
Z is O, $CH_2$, $CF_2$, CHF, cycloprop-1,2-ylene or a bond,
the number of ring atoms included in the macrocyclic ring being 14, 15, 16 or 17,
in free base form or in acid addition salt form.

More particularly the invention relates to a compound of the formula I, in which
$R_1$ is $-(CH_2)_kN(R_a)R_b$, in which
  k is 0, 1 or 2;
  $R_a$ is hydrogen or an optionally substituted $(C_{1-8})$alkyl, $(C_{3-8})$cycloalkyl, $(C_{3-8})$cycloalkyl-$(C_{1-4})$alkyl, aryl, aryl$(C_{1-4})$alkyl, heteroaryl, heteroaryl$(C_{1-4})$alkyl, chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydro-quinol-4-yl, 1,2,3,4-tetrahydro-isoquinol-4-yl, 1,2,3,4-tetrahydro-naphth-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1 lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl or 1,3,4,5-tetrahydro-benzo[c]oxepin-5-yl group; and
  $R_b$ is a $(C_{3-8})$cycloalkyl group, in which
    (a) one of the carbon ring members of the $(C_{3-8})$cycloalkyl moiety, which are different from the carbon ring member, to which the nitrogen atom carrying $R_a$ is attached, is optionally replaced by a hetero ring member, selected from the group consisting of —O—, —S—, —S(=O)—, —S(=O)₂— and —N(R$_c$)—, in which
      $R_c$ is hydrogen or an optionally substituted $(C_{1-8})$alkyl, $(C_{3-8})$cycloalkyl, $(C_{3-8})$cycloalkyl$(C_{1-4})$alkyl, aryl, aryl$(C_{1-4})$alkyl, heteroaryl or heteroaryl$(C_{1-4})$alkyl group,
    (b) the $(C_{3-8})$cycloalkyl moiety is substituted by 1 to 4 substituents, independently selected from the group consisting of halogen, cyano, oxo, hydroxy, $(C_{1-4})$alkoxy, $(C_{1-4})$alkoxy$(C_{1-4})$alkoxy, $(C_{1-4})$alkylthio, $(C_{1-4})$alkylsulfinyl, $(C_{1-4})$alkylsulfonyl, $(C_{1-4})$alkylcarbonyl, $(C_{1-4})$alkylcarbonyloxy, $(C_{1-4})$alkoxycarbonyl, $(C_{1-4})$alkoxycarbonyloxy and an optionally substituted $(C_{1-8})$alkyl, $(C_{3-8})$cycloalkyl, $(C_{3-8})$cycloalkyl-$(C_{1-4})$alkyl, aryl, aryl$(C_{1-4})$alkyl, heteroaryl, heteroaryl$(C_{1-4})$alkyl, non-aromatic heterocyclyl, non-aromatic heterocyclyl$(C_{1-4})$alkyl, chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydro-quinol-4-yl, 1,2,3,4-tetrahydro-isoquinol-4-yl, 1,2,3,4-tetrahydro-naphth-1-yl, 1,1-dioxo-1,2,3,4-tetrahydro-1 lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl or 1,3,4,5-tetrahydro-benzo[c]-oxepin-5-yl group, and
    (c) the $(C_{3-8})$cycloalkyl moiety is optionally substituted at two adjacent carbon ring members by two substituents, which form, together with the two adjacent carbon ring members, to which they are attached, a $(C_{3-8})$cycloalkyl group, in which
      (i) one of the carbon ring members of the $(C_{3-8})$cycloalkyl group thus formed, which are different from the said two adjacent carbon ring members, to which the said two substituents are optionally attached, is optionally replaced by a hetero ring member, selected from the group consisting of —O—, —S—, —S(=O)—, —S(=O)₂— and —N(R$_d$)—, in which
        $R_d$ is hydrogen or an optionally substituted $(C_{1-8})$alkyl, $(C_{3-8})$cycloalkyl, $(C_{3-8})$cycloalkyl$(C_{1-4})$alkyl, aryl, aryl$(C_{1-4})$alkyl, heteroaryl or heteroaryl$(C_{1-4})$alkyl group, and
      (ii) the $(C_{3-8})$cycloalkyl group thus formed is optionally substituted by 1 to 4 substituents, independently selected from the group consisting of halogen, cyano, oxo, hydroxy, $(C_{1-4})$alkoxy, $(C_{1-4})$alkoxy$(C_{1-4})$alkoxy, $(C_{1-4})$alkylthio, $(C_{1-4})$alkylsulfinyl, $(C_{1-4})$alkylsulfonyl, $(C_{1-4})$alkylcarbonyl, $(C_{1-4})$alkylcarbonyloxy, $(C_{1-4})$alkoxycarbonyl, $(C_{1-4})$alkoxycarbonyloxy and an optionally substituted $(C_{1-8})$alkyl, $(C_{3-8})$cycloalkyl, $(C_{3-8})$cycloalkyl$(C_{1-4})$alkyl, aryl, aryl$(C_{1-4})$alkyl, heteroaryl, heteroaryl$(C_{1-4})$alkyl, non-aromatic heterocyclyl, non-aromatic heterocyclyl$(C_{1-4})$alkyl, chroman-4-yl, isochroman-4-yl, thiochroman-4-yl, isothiochroman-4-yl, 1,1-dioxo-1lambda*6*thiochroman-4-yl, 2,2-dioxo-2lambda*6*-isothiochromanyl, 1,2,3,4-tetrahydro-quinol-4-yl, 1,2,3,4-tetrahydro-isoquinol-4-yl, 1,2,3,4-tetrahydro-naphth-1-yl, 1,1-dioxo-1,2,3,4-tetrahydro-1-lambda*6*-benzo[e][1,2]thiazin-4-yl, 2,2-dioxo-1,2,3,4-tetra-hydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]-oxathiin-4-yl, 2,3,4,5-tetrahydro-benzo[b]oxepin-5 yl or 1,3,4,5-tetrahydro-benzo[c]-oxepin-5-yl group;
$R_2$ is hydrogen or $(C_{1-4})$alkyl;
$R_3$ is hydrogen, $(C_{1-6})$alkyl or an optionally substituted $(C_{1-6})$alkylOC(=O)NH, $(C_{3-8})$cyclo-alkylOC(=O)NH, ($C_{3-8}$)cycloalkyl($C_{1-4}$)alkylOC(=O)NH, aryl($C_{1-4}$)alkylOC(=O)NH, heteroaryl($C_{1-4}$)alkylOC(=O)NH, ($C_{1-4}$)alkylC(=O)NH, ($C_{>8}$)cycloalkylC(=O)NH, arylC(=O)NH, aryl($C_{1-4}$)alkylC(=O)NH, heteroarylC(=O)NH or heteroaryl($C_{1-4}$)al-kylC(=O)NH group;

Ar is an aromatic or heteroaromatic ring, which ring is optionally substituted with halogen, ($C_{1-4}$)alkoxy, hydroxy or ($C_{1-4}$)alkyl, whereby U and $X_1$ are in ortho- or meta-position to each other;

U is a bond, $CF_2$, $CF_2CF_2$, CHF, CHFCHF, cycloprop-1,2-ylene, ($C_{1-3}$)alkylenoxy, ($C_{1-3}$)alkylenamino, ($C_{1-8}$)alkylene or $NR_e$, in which $R_e$ is hydrogen, ($C_{1-8}$)alkyl or ($C_{3-8}$)cycloalkyl;

$V_1$ is hydrogen, and $V_2$ is hydroxy, or $V_1$ and $V_2$ together are oxo;

W is CH=CH, cycloprop-1,2-ylene, $CH_2CH(OH)$, CH(OH)$CH_2$ or $CR_fR_fCR_fR_f$, in which each $R_f$, independently, is hydrogen, fluorine or ($C_{1-4}$)alkyl;

X is an optionally substituted ($C_{1-4}$)alkanylylidene, ($C_{1-4}$)alkylene, ($C_{3-8}$)cycloalkylene, piperidin-diyl, pyrrolidin-diyl, benzothiazole-4,6-diyl, benzoxazole-4,6-diyl, 1H-benzotriazole-4,6-diyl, imidazo[1,2-a]pyridine-6,8-diyl, benzo[1,2,5]oxadiazole-4,6-diyl, benzo[1,2,5]thiadiazole-4,6-diyl, 1H-indole-5,7-diyl, 1H-indole-4,6-diyl, 1H-benzimidazole-4,6-diyl or 1H-indazole-1,6-diyl group or an optionally substituted aromatic or heteroaromatic ring, whereby Y and C(=O)$NR_2$ are in meta-position to each other;

$X_1$ is $CR_gR_g$, in which each $R_g$, independently, is hydrogen, fluorine or an optionally substituted ($C_{1-8}$)alkyl, ($C_{1-4}$)alkoxy($C_{1-4}$)alkyl, ($C_{3-4}$)cycloalkyl or ($C_{3-4}$)cycloalkyl($C_{1-4}$)alkyl group;

Y is a bond, O, S(=O)$_2$, S(=O)$_2NR_h$, N($R_h$)S(=O)$_2$, $NR_h$, C($R_h$)OH, C(=O)$NR_h$, N($R_h$)C(=O), C(=O)N($R_h$)O or ON($R_h$)C(=O), in which $R_h$ is hydrogen, ($C_{1-8}$)alkyl or ($C_{3-8}$)cycloalkyl; and Z is O, $CH_2$, $CF_2$, CHF, cycloprop-1,2-ylene or a bond, the number of ring atoms included in the macrocyclic ring being 14, 15, 16 or 17, in free base form or in acid addition salt form.

On account of the asymmetrical carbon atoms present in the compounds of the formula I, the compounds may exist in pure optically active form or in the form of mixtures of optical isomers, e.g. in the form of racemic mixtures. All pure optical isomers and all their mixtures, including the racemic mixtures, are part of the present invention.

Halogen denotes fluorine, bromine, chlorine or iodine.

Optional substituents on alkyl, alkoxy or cycloalkyl groups or moieties may be, for example, one to three groups, independently selected from hydroxy, hydroxy($C_{1-4}$)alkyl, ($C_{1-4}$)alkoxy, ($C_{1-4}$)alkoxy($C_{1-4}$)alkyl, ($C_{1-4}$)alkoxy($C_{1-4}$)alkoxy, ($C_{1-4}$)alkylthio, ($C_{1-4}$)alkoxycarbonyl, ($C_{1-4}$)-alkylcarbonyloxy, ($C_{1-4}$)alkylcarbonyl, ($C_{1-4}$)alkylsulfonyl, cyano oxo and ($C_{3-8}$)cycloalkyl.

Optional substituents on chroman-4-yl, isochroman-4-yl, thiochroman-4-yl, isothiochroman-4-yl, 1,1-dioxo-1lambda*6*-isothiochroman-4-yl, 1,2,3,4-tetrahydro-quinol-4-yl, 1,2,3,4-tetrahydro-isoquinol-4-yl, 1,2,3,4-tetrahydro-naphth-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl, 1,3,4,5-tetrahydro-benzo[c]oxepin-5-yl, benzothiazole-4,6-diyl, benzoxazole-4,6-diyl, 1H-benzotriazole-4,6-diyl, imidazo[1,2-a]pyridine-6,8-diyl, benzo[1,2,5]oxadiazole-4,6-diyl, benzo[1,2,5]thiadiazole-4,6-diyl, 1H-indole-5,7-diyl, 1H-indole-4,6-diyl, 1H-benzimidazole-4,6-diyl, 1H-indazole-1,6-diyl, non-aromatic heterocyclyl, aryl or heteroaryl rings or moieties are, for example, one to four, especially one to three, groups independently selected from hydroxy, optionally substituted ($C_{1-8}$)alkyl, optionally substituted ($C_{1-6}$)alkoxy, S(=O)$_2$($C_{1-4}$)alkyl, ($C_{3-8}$)cycloalkyl, ($C_{3-8}$)cycloalkyl($C_{1-4}$)alkyl, cyano, nitro, trifluoromethyl, halogen, aryl, heteroaryl and optionally substituted carbamoyl.

An optionally substituted aryl or heteroaryl group may also carry, as optional substituents, for example, one to three groups selected from benzyloxy, phenoxy, S(=O)$_2NH_2$, N(H)S(=O)$_2$($C_{1-6}$)alkyl, N[($C_{1-6}$)alkyl]S(=O)$_2$($C_{1-4}$)alkyl, 2-oxo-pyrrolidin-1-yl, 2,5-dioxa-cyclopent-1-yl, carboxy, ($C_{1-4}$)alkoxycarbonyl, ($C_{1-4}$)alkylcarbamoyl, ($C_{1-4}$)alkylsulfonyl, ($C_{1-4}$)alkyl-carbonyloxy, ($C_{1-4}$)alkylcarbonyl, hydroxy($C_{1-4}$)alkyl and optionally substituted amino.

Optional substituents on alkanylylidene, alkylene, cycloalkylene, piperidin-diyl or pyrrolidin-diyl groups or moieties may be, for example, one to three groups independently selected from hydroxy, hydroxy($C_{1-4}$)alkyl, ($C_{1-4}$)alkoxy, ($C_{1-4}$)alkoxy($C_{1-4}$)alkyl, ($C_{1-4}$)alkoxy-($C_{1-4}$)-alkoxy, ($C_{1-4}$)alkylsulfanyl, ($C_{1-4}$)alkoxycarbonyl, ($C_{1-4}$)alkylcarbonyloxy, ($C_{1-4}$)alkylcarbonyl, ($C_{1-4}$)alkylsulfonyl, cyano, oxo, carboxy, carbamoyl and ($C_{3-8}$)cycloalkyl.

Optional substituents on amino groups can be, for example, one or two groups independently selected from ($C_{1-4}$)alkyl, ($C_{1-4}$)alkoxy($C_{1-4}$)alkyl, ($C_{1-4}$)alkoxycarbonyl, aryl($C_{1-4}$)alkoxycarbonyl and heteroaryl($C_{1-4}$)alkoxycarbonyl.

Optional substituents on carbamoyl can be, for example, one or two groups selected from ($C_{1-4}$)alkyl and ($C_{1-4}$)alkoxy ($C_{1-4}$)alkyl.

Aryl (and the aryl moiety in arylene) is, for example, naphthyl or preferably phenyl.

Heteroaryl (and the heteroaryl moiety in heteroarylene) is, for example, an aromatic 5- or 6-membered ring, in which 1, 2 or 3 ring atoms are hetero atoms independently selected from O, N and S, such as thiazolyl, oxazolyl, isoxazolyl, or preferably pyridyl.

Non-aromatic heterocyclyl is, for example, a non-aromatic 5- or 6-membered ring, in which 1, 2 or 3 ring atoms are hetero atoms independently selected from O, N and S, such as pyrrolidinyl, tetrahydrofuryl, tetrahydrothienyl or piperidyl.

Any non-cyclic carbon containing group or moiety with more than 1 carbon atom is straight-chain or branched.

Unless defined otherwise, carbon containing groups, moieties or molecules contain, for example, 1 to 8, preferably 1 to 6, more preferably 1 to 4, most preferably 1 or 2, carbon atoms.

In preferred embodiments, the invention relates to a compound of the formula I, in free base form or in acid addition salt form, in which (1) $R_a$ is hydrogen;
(2) k is 0;
(3) $R_2$ is hydrogen;
(4) $R_3$ is hydrogen;
(5) W is $CH_2CH_2$, CH=CH or phen-1,2-ylene;
(6) Y is O or NH;
(7) Z is a bond;
(8) the number of ring atoms included in the macrocyclic ring is 15 or 16;
(9) $V_1$ is hydrogen and $V_2$ is hydroxy;
(10) $X_1$ is $CH_2$;

(11) Ar is a phen-1,2-ylene or preferably phen-1,3-ylene ring, which ring is substituted with halogen or preferably unsubstituted;
(12) U is O, $CH_2$ or $CH_2O$;
(13) $R_b$ is a $(C_{3-8})$cycloalkyl, preferably a cyclopropyl, group, which $(C_{3-8})$cycloalkyl group is substituted by 1 to 4 substituents, preferably by 1 substituent, independently selected from the group consisting of an aryl and a heteroaryl group, preferably consisting of a phenyl, a pyridyl and an isoxazole group, which aryl or heteroaryl group is unsubstituted or substituted by 1 to 4 substituents, preferably by 1 substituent, independently selected from the group consisting of $(C_{1-8})$alkyl and hydroxy$(C_{1-8})$alkyl;
(14) X is an optionally substituted ar-1,3-ylene or heteroar-2,4-ylene ring, preferably a mono-substituted phen-1,3-ylene or pyrid-2,4-ylene ring, the substituent being selected from the group consisting of halogen, $(C_{1-8})$alkyl, $(C_{1-8})$alkoxy, $N(H)S(=O)_2(C_{1-6})$alkyl, $N[(C_{1-6})alkyl]-S(=O)_2(C_{1-6})$alkyl, 2-oxo-pyrrolidin-1-yl, 2,5-dioxa-cyclopent-1-yl, heteroaryl, $(C_{1-4})$alkoxy-$(C_{1-4})$alkyl, $(C_{1-8})$alkyl mono-substituted by oxo, $(C_{1-8})$alkoxy mono-substituted by oxo and carbamoyl substituted by two groups independently selected from $(C_{1-4})$alkyl.

The preferred embodiments (1) to (14) are preferred independently, collectively or in any combination or sub-combination.

In especially preferred embodiments, the invention relates to one or more than one of the compounds of the formula I mentioned in the Examples hereinafter, in free base form or in acid addition salt form.

In a further aspect; the invention relates to a process for the preparation of the compounds of the formula I and their salts, comprising the steps of
a) cyclisation by metathesis of a compound of the formula

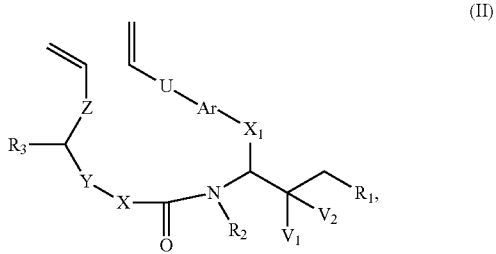

(II)

in which $R_1$, $R_2$, $R_3$, Ar, U, $V_1$, $V_2$, X, $X_1$, Y and Z are as defined for the formula I, in the presence of a catalyst, for instance a ruthenium, tungsten or molybdenum complex, optionally followed by reduction or functionalisation of the resulting carbon-carbon-double bond, or
b) intramolecular cyclisation of a compound of the formula

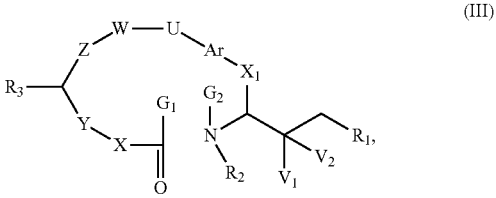

(III)

in which $R_1$, $R_2$, $R_3$, Ar, U, $V_1$, $V_2$, W, X, $X_1$, Y and Z are as defined for the formula I, $G_1$ is a leaving group and $G_2$ is hydrogen or a protecting group, in each case optionally followed by reduction, oxidation or functionalisation of the resulting compound and/or by cleavage of protecting groups optionally present, and of recovering the so obtainable compound of the formula I in free base form or in acid addition salt form.

The reactions can be effected according to conventional methods, for example as described in the Examples.

The working-up of the reaction mixtures and the purification of the compounds thus obtainable may be carried out in accordance with known procedures.

Acid addition salts may be produced from the free bases in known manner, and vice-versa.

Compounds of the formula I can also be prepared by further conventional processes, which processes are further aspects of the invention, e.g. as described in the Examples.

The starting materials of the formulae II and III are known or may be prepared according to conventional procedures starting from known compounds, for example as described in the Examples.

Compounds of the formula I and their pharmaceutically acceptable acid addition salts, hereinafter referred to as "agents of the invention", exhibit valuable pharmacological properties when tested in vitro and in animals, and are therefore useful as medicaments.

The agents of the invention are inhibitors of aspartic proteases and can be used for the treatment of disorders involving processing by such enzymes. Particularly they inhibit beta-secretase and as such inhibit the generation of beta-amyloid and the subsequent aggregation into oligomers and fibrils.

Test 1: Inhibition of Human BACE

Recombinant BACE (extracellular domain, expressed in baculovirus and purified using standard methods) at 0.1-10 nM concentration is incubated with the test compound at various concentrations for 1 hour at room temperature in 10-100 mM acetate buffer, pH 4.5, containing 0.1% CHAPS. Synthetic fluorescence-quenched peptide substrate, derived from the sequence of APP and containing a suitable fluorophore-quencher pair is added to a final concentration of 1-5 µM and the increase in fluorescence is recorded at a suitable excitation/emission wavelength in a microplate spectro-fluorimeter for 5-30 minutes in 1-minute intervals. $IC_{50}$ values are calculated from percentage of inhibition of BACE-activity as a function of the test compound concentration.

Test 2: Inhibition of Human BACE-2

Recombinant BACE-2 (extracellular domain, expressed in baculovirus and purified using standard methods) at 0.1-10 nM concentrations is incubated with the test compound at various concentrations for 1 hour at room temperature in 10-100 mM acetate buffer, pH 4.5, containing 0.1% CHAPS. Synthetic peptide substrate derived from the sequence of APP and containing a suitable fluorophore-quencher pair is added to a final concentration of 1-5 µM and the increase in fluorescence is recorded at a suitable excitation/emission wavelength in a microplate spectro-fluorimeter for 5-30 minutes in 1-minute intervals. $IC_{50}$ values are calculated from percentage of inhibition of BACE-2-activity as a function of the test compound concentration.

Test 3: Inhibition of Human Cathepsin D

Recombinant cathepsin D (expressed as procathepsin D in baculovirus, purified using standard methods and activated by incubation in sodium formate buffer pH 3.7) is incubated with the test compound at various concentrations for 1 hour at room temperature in sodium formate or sodium acetate buffer at a suitable pH within the range of pH 3.0-5.0 Synthetic peptide substrate Mca-Gly-Lys-Pro-Ile-Leu-Phe-Phe-Arg-Leu-Lys(DNP)-D-Arg-$NH_2$ is added to a final concentration of 1-5 µM and the increase in fluorescence is recorded at excitation of 325 nm and emission at 400 nm in a microplate spectro-fluorimeter for 5-30 minutes in 1-minute intervals. $IC_{50}$ values are calculated from percentage of inhibition of cathepsin D-activity as a function of the test compound concentration.

Test 4: Inhibition of Cellular Release of Amyloid Peptide 1-40

Chinese hamster ovary cells are transfected with the gene for amyloid precursor protein. Cells are plated at a density of 8000 cells/well in a 96-well microtiter plate and cultivated for 24 hours in DMEM cell culture medium containing 10% FCS. The test compound is added to the cells at various concentrations, and cells are cultivated for 24 hours in the presence of the test compound. The supernatants are collected, and the concentration of amyloid peptide 1-40 is determined using sandwich ELISA. The potency of the compound is calculated from the percentage of inhibition of amyloid peptide release as a function of the test compound concentration.

In at least one of the above-indicated tests, the agents of the invention show activity at concentrations below 50 µM.

Specifically, the agent of the invention described in Example 5 shows an $IC_{50}$ value of 0.25 µM in Test 1.

The agents of the invention are therefore useful e.g. for the treatment and/or prevention of neurological and vascular disorders related to beta-amyloid generation and/or aggregation, such as neurodegenerative diseases like Alzheimer's disease, Down's Syndrome, memory and cognitive impairment, dementia, amyloid neuropathies, brain inflammation, nerve and brain trauma, vascular amyloidosis, or cerebral haemorrhage with amyloidosis.

Some of the agents of the invention also inhibit BACE2 (beta-site APP-cleaving enzyme 2) or Cathepsin D, close homologues of the pepsin-type aspartyl proteases and of beta-secretase. Due to the correlation of BACE2 and CathD expression with a more tumorigenic and metastatic potential of tumor cells, such inhibitors are useful for the suppression of the metastasis process associated with tumor cells.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range from about 10 to about 2000, preferably from about 10 to about 200, mg of an agent of the invention conveniently administered, for example, in divided doses up to four times a day or in sustained release form.

The agent of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a medicament, e.g. for the treatment of neurological or vascular disorders related to beta-amyloid generation and/or aggregation.

The present invention furthermore provides a pharmaceutical composition comprising an agent of the invention in association with at least one pharmaceutical carrier or diluent. Such compositions may be manufactured in conventional manner. Unit dosage forms contain, for example, from about 1 to about 1000, preferably from about 1 to about 500, mg of an agent of the invention.

The agents of the invention can be administered alone or in combination with other pharmaceutical agents effective in the treatment of conditions mentioned above.

The pharmaceutical combination may be in the form of a unit dosage form, whereby each unit dosage will comprise a predetermined amount of the two components, in admixture with suitable pharmaceutical carriers or diluents. Alternatively, the combination may be in form of a package containing the two components separately, e.g. a pack or dispenser-device adapted for the concomitant or separate administration of the two active agents, wherein these agents are separately arranged.

Moreover the present invention provides the use of an agent of the invention, for the manufacture of a medicament for the treatment of any neurological or vascular disorders related to beta-amyloid generation and/or aggregation.

In still a further aspect, the present invention provides a method for the treatment of any neurological or vascular disorders related to beta-amyloid generation and/or aggregation, in a subject in need of such treatment, which comprises administering to such subject a therapeutically effective amount of an agent of the invention.

The following Examples illustrate the invention, but do not limit it.

EXAMPLES

| Abbreviations | |
|---|---|
| AcOH | acetic acid |
| aq | aqueous |
| 9-BBN | 9-borabicyclo[3.3.1]nonane |
| $BF_3*Et_2O$ | boron trifluoride-diethyl etherate |
| BINAP | (±)-1,1 -binaphth-2,2 -diyl-bis(diphenylphosphine) |
| CbzCl | benzyl chloroformate |
| DCM | dichloromethane |
| Dess-Martin reagent | 1,1,1-tris(acetoxy)-1,1-dihydro-1,2-benzdioxol-3(1H)-one |
| DMF | N,N-dimethylformamide |
| DMSO | dimethylsulfoxide |
| EDC*HCl | 1-ethyl-3[3-(dimethylamino)propyl]-carbodiimide hydrochloride |
| eq | equivalent(s) |
| ES | electron spray |
| EtMgBr | ethyl magnesium bromide |
| $Et_3N$ | triethylamine |
| EtOAc | ethyl acetate |
| EtOH | ethanol |
| Grubbs II catalyst | [1,3-bis(2,4,6-trimethylphenyl)-2-imidazolidinylidene]dichloro(phenyl-methylene)(triphenylphosphine)-ruthenium |
| h | hour(s) |
| HATU | O-(7-azabenzotriazole-1-yl)-N,N,N',N'-tetramethyluronium hexafluorophosphate |
| HOBt | hydroxybenzotriazole |
| HPLC | high pressure liquid chromatography |
| LC | liquid chromatography |
| $LiOH*H_2O$ | lithium hydroxide hydrate |
| MeCN | acetonitrile |
| MeI | iodomethane |
| MeMgCl | methyl magnesium chloride |
| MeOH | methanol |
| min | minute(s) |
| m. p. | melting point |
| MS | mass spectrometry |
| $NH_3$ | 14N aqueous ammonia |
| NMR | nuclear magnetic resonance spectrometry |
| Pd/C | palladium on charcoal |
| $Pd(OAc)_2$ | palladium(II) acetate |
| Rf | retention factor (thin layer chromatography) |
| rt | room temperature |
| sec | second(s) |

-continued

| Abbreviations | |
|---|---|
| SK-CC02-A | 2-(dimethylamino)ferrocen-1-yl-palladium(II)chloride dinorbornylphosphine complex |
| $SnCl_2*2\,H_2O$ | tin chloride hydrate |
| TBAI | tetrabutylammonium iodide |
| TBME | tert-butyl methyl ether |
| THF | tetrahydrofuran |

Example 1

(S)-19-Acetyl-4-{(R)-1-hydroxy-2-[1-(3-isopropyl-phenyl)-cyclopropylamino]-ethyl}-11-oxa-3,16-diaza-tricyclo[15.3.1.1*6,10*]docosa-1(21), 6,8,10 (22), 17,19-hexaen-2-one a) [3-Acetyl-5-(1S,2R)-1-(3-(allyloxy-benzyl)-3-benzyloxycarbonyl-[1-(3-isopropyl-phenyl)-cyclopropyl]-amino)-2-hydroxy-propylcarbamoyl)-phenyl]-allyl-carbamic acid benzyl ester 500 mg (795 µmol) of ((1S,2R)-1-(3-allyloxy-benzyl)-3-{benzyloxycarbonyl-[1-(3-isopropyl-phenyl)-cyclopropyl]-amino}-2-hydroxy-propyl)-carbamic acid tert-butyl ester (building block C7) are dissolved in 4 ml of 4 N HCl in dioxane, and the mixture is stirred for 1 h, concentrated and co-evaporated with toluene. The residue is dissolved in DCM (5 ml), and the solution is added to a solution of HOBt (183 mg, 1.19 mmol, 1.5 eq), EDC*HCl (234 mg, 1.19 mmol, 1.5 eq), $Et_3N$ (445 µl, 3.18 mmol, 4 eq) and 3-acetyl-5-allylbenzyloxycarbonyl-amino)benzoic acid (building block A5) in DCM (10 ml). The reaction mixture is stirred at rt for 16 h and then quenched with 1N HCl in $H_2O$. The mixture is diluted with DCM, and the organic layer is separated, washed with aq $NaHCO_3$ and brine, dried over sodium sulfate, filtered and concentrated. The residue is purified by column chromatography using EtOAc/hexane in a ratio of 3 to 7 to give the product.

MS (ES+): 864=$[M+H]^+$.

HPLC (Nucleosil C18HD, 4×70 mm, 3 µm, 20-100% MeCN (6 min), 100%. MeCN 1.5 min)) retention time: 7.12 min.

b) (Z)—(S)-19-Acetyl-4-((R)-2-{benzyloxycarbonyl-[1(3-isopropyl-phenyl)cyclopropyl]-amino}-1-hydroxy-ethyl)-2-oxo-11-oxa-3,16-diaza-tricyclo [15.3.1.1*6,10*]docosa-1(21), 6,8,10(22), 13,17,19-heptaene-16-carboxylic acid benzyl ester Grubbs II catalyst (24.3 mg, 28.6 µmol, 0.05 eq) is dissolved in dry DCM under argon, and the solution is refluxed for 5 min. 3-Acetyl-5-((1S,2R)-1-(3-allyl-benzyl)-3{benzyloxycarbonyl-[1-(3-isopropyl-phenyl)-cyclopropyl]-amino}-2-hydroxy-propylcarbamoyl)-phenyl]-allyl-carbamic acid benzyl ester (495 mg, 573 µmol, 1 eq) is dissolved in DCM (8 ml), and the solution is added by syringe within 3 min. The reaction mixture is refluxed for 90 min and then cooled to rt. Charcoal (2 g) is added, the mixture is stirred for 30 min and filtered, and the filtrate is concentrated. The residue is purified by column chromatography using EtOAc/hexane in a ratio of 2 to 3 to give the product.

MS (ES+): 836=$[M+H]^+$.

HPLC (Nucleosil C18HD, 4×70 mm, 3 µm, 20-100% MeCN (6 min), 100% MeCN (1.5 min)) retention time: 6.79 min.

c) (S)-19-Acetyl-4-{(R)-1-hydroxy-2-[1-(3-isopropyl-phenyl)cyclopropylamino]-ethyl}-11-oxa-3,16-diaza-tricyclo[15.3.1.1*6,10*]docosa-1(21), 6,8,10 (22), 17,19-hexaen-2-one (Z)—(S)-19-Acetyl-4-((R)-2{benzyloxycarbonyl-[1-(3-isopropyl-phenyl)-cyclopropyl]-amino}1-hydroxy-ethyl)-2-oxo-11-oxa-3,16-diaza-tricyclo[15.3.1.1*6,10]*docosa-1 (21), 6,8,10(22), 13,17,19-heptaene-16-carboxylic acid benzyl ester (402 mg, 481 µmol, 1 eq) is dissolved in THF (6 ml), and the solution is added to a suspension of Pd/C (58.3 mg, 5%) in EtOH (30 ml). The reaction mixture is stirred under 1 atmosphere of hydrogen for 2 h. The mixture is filtered, the filtrate is concentrated, the residue is dissolved in MeOH, and diethyl ether is added, until the product precipitates.

MS (ES+): 570=$[M+H]^+$.

HPLC (Nucleosil C18HD, 4×70 mm, 3 µm, 20-100% MeCN (6 min), 100% MeCN (1.5 min)) retention time: 4.09 min.

$^1$H-NMR (400 MHz, DMSO-$d_6$): 8.03 (d, 1H), 7.20-6.94 (m, 8H), 6.81-6.67 (m, 3H), 6.15 (t, 1H), 4.78 (d, 1H), 4.26-4.17 (m, 1H), 3.95-3.82 (m, 2H), 3.55-3.35 (m, 2H), 3.09-2.92 (m, 2H), 2.86-2.75 (m, 1H), 2.71-2.45 (m, 3H), 2.44 (s, 3H), 1.80-1.45 (m, 4H), 1.14 (d, 6H), 0.95-0.75 (m, 4H).

Example 2

(S)-4-{(R)-1-Hydroxy-2-[1-(3-isopropyl-phenyl)-cyclopropylamino]ethyl}-19-(2-oxo-propoxy)-11, 16dioxa-3-aza-tricyclo[15.3.1.1*6,10*]docosa-1(21), 6,8,10(22), 17,19-hexaen-2-one The title compound is obtained by an analogous reaction sequence as for example 1, starting from ((1S,2R)-1-(3-allyloxy-benzyl)-3-{benzyloxycarbonyl-[1-(3-isopropyl-phenyl)-cyclopropyl]-amino}-2-hydroxy-propyl)-carbamic acid tert-butyl ester (building block C7) and 3-allyloxy-5-(2-oxo-propoxy)-benzoic acid (building block A2).

MS (ES+): 601=$[M+H]^+$.

HPLC (Nucleosil C18HD, 4×70 mm, 3 µm, 20-100% MeCN (6 min), 100% MeCN (1.5 min)) retention time: 4.33 min.

$^1$H-NMR (400 MHz, DMSO-$d_6$): 7.95 (d, 1H), 7.19-7.09 (m, 3H), 7.08-6.94 (m, 3H), 6.78 (d, 1H), 6.70 (d, 1H), 6.64 (s, 1H), 6.55 (s, 1H), 6.44 (s, 1H), 4.86-4.74 (m, 1H), 4.75 (s, 2H), 4.39-4.27 (m, 1H), 4.26-4.16 (m, 1H), 4.11-3.83 (m, 3H), 3.55-3.44 (m, 1H), 2.94 (dd, 1H), 2.88-2.75 (m, 1H), 2.71-2.48 (m, 2H), 2.12 (s, 3H), 1.86-1.60 (m, 4H), 1.16 (d, 6H), 0.99-0.76 (m, 4H).

Example 3

(S)-4-{(R)-1-Hydroxy-2-[1-(3-isopropyl-phenyl)-cyclopropylamino]ethyl}-19-oxazol-2-yl-11-oxa-3, 16diaza-tricyclo[15.3.1.1*6,10*]docosa-1(21), 6,8, 10(22), 17,19-hexaen-2-one The title compound is obtained by an analogous reaction sequence as for example 1, starting from ((1S,2R)-1-(3-allyloxy-benzyl)-3-{benzyloxycarbonyl-[1-(3-isopropyl-phenyl)-cyclopropyl]-amino}-2-hydroxy-propyl)carbamic acid tert-butyl ester (building block C7) and 3-(allyl-benzyloxy carbonyl-amino)-5-oxazol-2-yl-benzoic acid (building block A3).

MS (ES+): 595=[M+H]⁺.

HPLC (Nucleosil C18HD, 4×70 mm, 3 μm, 20-100% MeCN (6 min), 100% MeCN (1.5 min)) retention time: 4.16 min.

$^1$H-NMR (400 MHz, DMSO-$d_6$): 8.15 (s, 1H), 8.03 (d, 1H), 7.32 (s, 1H), 7.27 (s, 1H), 7.21 (s, 1H), 7.18-7.07 (m, 3H), 7.06-6.91 (m, 3H), 6.80-6.64 (m, 3H), 6.21 (t, 1H), 4.74 (d, 1H), 4.28-4.18 (m, 1H), 3.95-3.83 (m, 2H), 3.50-3.35 (m, 3H), 3.08-2.92 (m, 2H), 2.81-2.65 (m, 1H), 2.64-2.42 (m, 3H), 1.80-1.45 (m, 4H), 1.10 (d, 6H), 0.97-0.75 (m, 4H).

Example 4

(S)-4-{(R)-2-[3-tert-Butyl-phenyl)-cyclopropylamino]-1-hydroxy-ethyl}-2-oxo-11,16-dioxa-3-azatricyclo[15.3.1.1*6,10*]docosa-1(21), 6,8,10(22),17, 19-hexaene-19-carboxylic acid dimethylamide The title compound is obtained by an analogous reaction sequence as for example 1, starting from ((1S,2R)-1-(3-allyloxy-benzyl)-3-{benzyloxycarbonyl-[1-(3tert-butyl-phenyl)-cyclopropyl]-amino}-2-hydroxy-propyl)-carbamic acid tert-butyl ester (building block C6) and 5-allyloxy-N,N-dimethyl-isophtalamic acid (building block A4).

Rf (DCM/MeOH/NH$_3$=90/9/1): 0.38.

MS (ES+): 614=[M+H]⁺.

$^1$H-NMR (400 MHz, DMSO-$d_6$): 8.08 (d, 1H), 7.33 (s, 1H), 7.20-7.11 (m, 3H), 7.06-6.90 (m, 5H), 6.79 (d, 1H), 6.73 (dd, 1H), 4.83 (d, 1H), 4.43-4.32 (m, 1H), 4.26-4.19 (m, 1H), 4.16-4.08 (m 1H), 4.01-3.84 (m, 2H), 3.55-3.47 (m, 1H), 3.01-2.80 (m, 7H), 2.69-2.57 (m, 2H), 1.88-1.62 (m, 5H), 124 (s, 9H), 1.02-0.79 (m, 5H).

Example 5

(S)-18-Acetyl-4-{(R)-1-hydroxy-2-[1-(3-isopropylphenyl)-cyclopropylamino]-ethyl}-15-oxa-3-azatricyclo[14.3.1.1*6,10*]henicosa-1(20),6,8,10(21), 16,18-hexaen-2-one The title compound is obtained by an analogous reaction sequence as for example 1, starting from ((1S,2R)-1-(3-allyl-benzyl)-3-{benzyloxycarbonyl-[1-(3-isopropyl-phenyl)-cyclopropyl]-amino}-2-hydroxy-propyl)carbamic acid tert-butyl ester (building block C5) and 3-acetyl-5-allyloxy-benzoic acid (building block A6).

MS (ES+): 555=[M+H]⁺.

HPLC (Nucleosil C18HD, 4×70 mm, 3 μm, 20-100% MeCN (6 min), 100% MeCN (1.5 min)) retention time: 4.59 min.

$^1$H-NMR (400 MHz, DMSO-$d_6$): 8.20 (d, 1H), 7.68 (s, 1H), 7.44-7.37 (m, 2H), 7.21-6.91 (m, 8H), 4.81 (d, 1H), 4.42-4.33 (m, 1H), 4.22-4.07 (m, 2H), 3.56-3.50 (m, 1H), 3.15-3.08 (m, 1H), 2.89-2.78 (m, 1H), 2.76-2.52 (m, 8H), 2.00-1.78 (m, 2H), 1.54-1.32 (m, 2H), 1.18 (d, 6H), 1.05-0.82 (m, 4H).

Example 6

(S)-18-Acetyl-4-{(R)-1-hydroxy-2-[1-(3-isopropylphenyl)-cyclopropylamino]-ethyl}-3,15-diaza-tricyclo[14.3.1.1*6,10*]henicosa-1(20),6,8,10(21),16,18-hexaen-2-one The title compound is obtained by an analogous reaction sequence as for example 1, starting from ((1S,2R)-1-(3-allylbenzyl)-3{benzyloxycarbonyl-[1-(3-isopropyl-phenyl)-cyclopropyl]-amino}-2-hydroxy-propyl)-carbamic acid tert-butyl ester (building block C5) and 3-acetyl-5-(allyl-benzyloxycarbonyl-amino)-benzoic acid (building block A5).

MS (ES+): 554=[M+H]⁺.

HPLC (Nucleosil C18HD, 4×70 mm, 3 μm, 20-100% MeCN (6 min), 100% MeCN (1.5 min)) retention time: 4.33 min.

$^1$H-NMR (400 MHz, DMSO-$d_6$): 7.99 (d, 1H), 7.35 (s, 1H), 7.20-6.94 (m, 9H), 6.49 (s, 1H), 6.21 (t, 1H), 4.73 (d, 1H), 4.14-4.04 (m, 1H), 3.56-3.48 (m, 1H), 3.40-3.35 (m, 1H), 3.13-2.95 (m, 2H), 2.90-2.79 (m, 1H), 2.72-2.55 (m, 5H), 2.45 (s, 3H), 1.96-1.87 (m, 1H), 1.85-1.72 (m, 1H), 1.52-1.38 (m, 1H), 1.18 (d, 6H), 1.18-1.05 (m, 1H), 1.05-0.95 (m, 3H), 0.92-0.85 (m, 1H).

Example 7

(S)-4-{(R)-1-Hydroxy-2-[1-(3-isopropyl-phenyl) cyclopropylamino]-ethyl}-18-methoxymethyl-3,15, 17-triaza-tricyclo[14.3.1.1*6,10*]henicosa-1(20),6, 8,10(21),16,18-hexaen-2-one The title compound is obtained by an analogous reaction sequence as for example 1, starting from ((1S,2R)-1-(3-allylbenzyl)-3-{benzyloxycarbonyl-[1-(3-isopropyl-phenyl)-cyclopropyl]-amino}-2-hydroxy-propyl)carbamic acid tert-butyl ester (building block C5) and 2-allylamino-6-methoxymethyl-isonicotinic acid (building block A1).

MS (ES+): 557=[M+H]⁺.

HPLC (Nucleosil C18HD, 4×70 mm, 3 μm, 20-100% MeCN (6 min), 100% MeCN (1.5 min)) retention time: 4.08 min.

$^1$H-NMR (400 MHz, DMSO-$d_6$): 8.05 (d, 1H), 7.32 (s, 1H), 7.20-7.07 (m, 3H), 7.06-6.94 (m, 4H), 6.66 (t, 1H), 6.52 (s, 1H), 5.93 (s, 1H), 4.72 (d, 1H), 4.18 (s, 2H), 4.10-3.98 (m, 1H), 3.53-3.43 (m, 1H), 3.30-3.20 (m, 1H), 3.27 (s, 3H), 3.13-2.94 (m, 2H), 2.90-2.77 (m, 1H), 2.70-2.50 (m, 5H), 1.92-1.85 (m, 1H), 1.80-1.68 (m, 1H), 1.42-1.26 (m, 1H), 1.25-1.10 (m, 1H), 1.16 (d, 6H), 1.05-0.77 (m, 4H).

Example 8

(S)-4-{(R)-1-Hydroxy-2-[1-(3-isopropyl-phenyl)-cyclopropylamino]-ethyl}-19-methoxymethyl-11-oxa-3,16-diaza-tricyclo[15.3.1.1*6,10*]docosa-1 (21),6,8,10(22),17,19-hexaen-2-one The title compound is obtained by an analogous reaction sequence as for example 1, starting from ((1S,2R)-1-(3-allyloxy-benzyl)-3-{benzyloxycarbonyl-[1-(3-isopropyl-phenyl)-cyclopropyl]-amino}2-hydroxy-propyl)-carbamic acid tert-butyl ester (building block C7) and 3-(allyl-benzyloxycarbonyl-amino)-5-methoxymethyl-benzoic acid (building block A7).

MS (ES+): 572=[M+H]⁺.

HPLC (Nucleosil C18HD, 4×70 mm, 3 μm, 20-100% MeCN (6 min), 100% MeCN (1.5 min)) retention time: 3.91 min.

$^1$H-NMR (400 MHz, DMSO-$d_6$): 7.86 (d, 1H), 7.18-6.95 (m, 6H), 6.80-6.65 (m, 2H), 6.58-6.45 (m, 3H), 5.81 (t, 1H), 4.75-4.68 (m, 1H), 4.30-4.23 (m, 1H), 4.23 (s, 2H), 3.95-3.78 (m, 2H), 3.50-3.33 (m, 2H), 3.24 (s, 3H), 3.05-2.92 (m, 2H), 2.89-2.52 (m, 1H), 2.70-2.46 (m, 3H), 1.77-1.45 (m, 4H), 1.17 (d, 6H), 0.98-0.88 (m, 3H), 0.84-0.75 (m, 1H).

Example 9

(S)-4-{(R)-1-Hydroxy-2-[1-(3-isopropyl-phenyl)-cyclopropylamino]ethyl}-19-methyl-11-oxa-3,16,18-triaza-tricyclo[15.3.1.1*6,10*]docosa-1(21),6,8,10(22),17,19-hexaen-2-one The title compound is obtained by an analogous reaction sequence as for example 1, starting from ((1S,2R)-1-(3-allyloxy-benzyl)-3-{benzyloxycarbonyl-[1-(3-isopropyl-phenyl)-cyclopropyl]-amino}-2-hydroxy-propyl)-carbamic acid tert-butyl ester (building block C7) and 2-allylamino-6-methyl-isonicotinic acid hydrochloride (building block A8).

MS (ES+): 543=[M+H]$^+$.

$^1$H-NMR (400 MHz, DMSO-d$_6$): 8.03 (d, 1H), 7.18-7.09 (m, 3H), 7.06-6.94 (m, 3H), 6.78-4.68 (m, 2H), 6.51 (t, 1H), 6.24 (s, 1H), 6.11 (s, 1H), 4.75 (d, 1H), 4.26-4.17 (m, 1H), 3.95-3.77 (m, 2H), 3.46-3.30 (m, 2H), 3.07-2.94 (m, 2H), 2.88-2.77 (m, 1H), 2.65-2.45 (m, 3H), 2.20 (s, 3H), 1.82-1.58 (m, 3H), 1.57-1.45 (m, 1H), 1.17 (d, 6H), 0.98-0.88 (m, 3H), 0.87-0.79 (m, 1H).

Example 10

(S)-19-Acetyl-4-{(R)-1-hydroxy-2-[1-(34isopropyl-phenyl)-cyclopropylamino]-ethyl}-11,16-dioxa-3-aza-tricyclo[15.3.1.1*6,10*]docosa-1(21),6,8,10(22),17,19-hexaen-2-one The title compound is obtained by an analogous reaction sequence as for example 1, starting from ((1S,2R)-1-(3-allyloxy-benzyl)-3-benzyloxycarbonyl-[1-(3-isopropyl-phenyl)-cyclopropyl]-amino-2-hydroxy-propyl)-carbamic acid tert-butyl ester (building block C7) and 3-acetyl-5-allyloxy-benzoic acid (building block A6).

MS (ES+): 571=[M+H]$^+$.

HPLC (Nucleosil C18HD, 4×70 mm, 3 μm, 20-100% MeCN (6 min), 100% MeCN (1.5 min)) retention time: 4.43 min.

$^1$H-NMR (400 MHz, DMSO-d$_6$): 8.14 (d, 1H), 7.60 (s, 1H), 7.48 (s, 1H), 7.28 (s, 1H), 7.19-7.11 (m, 3H), 7.07 (d, 1H), 7.01-6.95 (m, 2H), 6.80 (d, 1H), 6.72 (dd, 1H), 4.84 (d, 1H), 4.47-4.37 (m, 1H), 4.27-4.12 (m, 2H), 4.02-3.91 (m, 2H), 3.58-3.50 (m, 1H), 3.00-2.92 (m, 1H), 2.85-2.76 (m, 1H), 2.73-2.65 (m, 1H), 2.65-2.49 (m, 2H), 2.56 (s, 3H), 1.87-1.63 (m, 4H), 1.15 (d, 6H), 1.00-0.87 (m, 3H), 0.87-0.80 (m, 1H).

Example 11

(S)-4-{(R)-1-Hydroxy-2-[1-(3-isopropyl-phenyl)-cyclopropylamino]ethyl}-19-methoxymethyl-11-oxa-3,16,18-triaza-tricyclo[15.3.1.1*6,10]*docosa-1(21),6,8,10(22), 17,19-hexaen-2-one The title compound is obtained by an analogous reaction sequence as for example 1, starting from ((1S,2R)-1-(3-allyloxy-benzyl)-3{benzyloxycarbonyl-[1-(3-isopropyl-phenyl)-cyclopropyl]-amino}-2-hydroxy-propyl)-carbamic acid tert-butyl ester (building block C7) and 2-allyl-amino-6-methoxymethyl-isonicotinic acid (building block A1).

MS (ES+): 573=[M+H]$^+$.

HPLC (Nucleosil C18HD, 4×70 mm, 3 μm, 20-100% MeCN (6 min), 100% MeCN (1.5 min)) retention time: 4.02 min.

$^1$H-NMR (400 MHz, DMSO-d$_6$): 8.10 (d, 1H), 7.20-7.10 (m, 3H), 7.09-6.98 (m, 3H), 6.80-6.70 (m, 2H), 6.64 (t, 1H), 6.51 (s, 1H), 6.24 (s, 1H), 4.78 (d, 1H), 4.29-4.24 (m, 1H), 4.24 (s, 2H), 3.96-3.80 (m, 2H), 3.50-3.30 (m, 2H), 3.31 (s, 3H), 3.10-2.95 (m, 2H), 2.90-2.77 (m, 1H), 2.70-2.46 (m, 3H), 1.80-1.62 (m, 3H), 1.58-1.44 (m, 1H), 1.16 (d, 6H), 1.00-0.88 (m, 3H), 0.87-0.75 (m, 1H).

Example 12

(S)-4-{(R)-1-Hydroxy-2-[1-(3-isopropyl-phenyl)-cyclopropylamino]-ethyl}-181 ethoxymethyl-3,15-diaza-tricyclo[14.3.1.1*6,10*]henicosa-1(20),6,8,10(21),16,18-hexaen-2-one The title compound is obtained by an analogous reaction sequence as for example 1, starting from ((1S,2R)-1-(3-allyl-benzyl)-3-{benzyloxycarbonyl-[1-(3-isopropyl-phenyl)-cyclopropyl]-amino}-2-hydroxy-propyl)-carbamic acid tert-butyl ester (building block C5) and 3-(allyl-benzyloxycarbonyl-amino)-5-methoxymethyl-benzoic acid (building block A7).

MS (ES+): 556=[M+H]$^+$.

HPLC (Nucleosil C18HD, 4×70 mm, 3 μm, 20-100% MeCN (6 min), 100% MeCN (1.5 min)) retention time: 4.39 min.

$^1$H-NMR (400 MHz, DMSO-d$_6$): 7.81 (d, 1H), 7.34 (s, 1H), 7.19-7.10 (m, 3H), 7.08-6.95 (m, 4H), 6.57 (s, 1H), 6.51 (s, 1H), 6.21 (s, 1H), 5.81 (t, 1H), 4.69 (d, 1H), 4.21 (s, 2H), 4.08-3.98 (m, 1H), 3.52-3.45 (m, 1H), 3.38-3.25 (m, 1H), 3.20 (s, 3H), 3.13-3.05 (m, 1H), 3.02-2.90 (m, 1H), 2.88-2.78 (m, 1H), 2.70-2.50 (m, 5H), 1.95-1.85 (m, 1H), 1.83-1.70 (m, 1H), 1.53-1.38 (m, 1H), 1.19 (d, 6H), 1.18-1.03 (m, 1H), 1.06-0.90 (m, 3H), 0.87-0.79 (m, 1H).

Example 13

(S)-4-{(R)-1-Hydroxy-2-[1-(3-isopropyl-phenyl)-cyclopropylamino]-ethyl}-18-(2-oxo-propoxy)-15-oxa-3-aza-tricyclo[14.3.1.1*6,10*]henicosa-1(20),6,8,10(21),16,18-hexaen-2-one The title compound is obtained by an analogous reaction sequence as for example 1, starting from ((1S,2R)-1-(3-allyl-benzyl)-3-{benzyloxycarbonyl-41-(3-isopropyl-phenyl)-cyclopropyl]-amino}-2-hydroxy-propyl)-carbamic acid tert-butyl ester (building block C5) and 3-allyloxy-5-(2-oxo-propoxy)-benzoic acid (building block A2).

MS (ES+): 585=[M+H]$^+$.

HPLC (Nucleosil C18HD, 4×70 mm, 3 μm, 20-100% MeCN (6 min), 100% MeCN (1.5 min)) retention time: 4.67 min.

$^1$H-NMR (400 MHz, DMSO-d$_6$): 7.95 (d, 1H), 7.36 (s, 1H), 7.20-6.93 (m, 7H), 6.54 (s, 1H), 6.39 (s, 1H), 6.33 (s, 1H), 4.80-4.71 (m, 3H), 4.33-4.24 (m, 1H), 4.13-4.02 (m, 2H), 3.58-3.50 (m, 1H), 3.12-3.06 (m, 1H), 2.90-2.78 (m, 1H), 2.72-2.48 (m, 5H), 2.12 (s, 3H), 1.98-1.73 (m, 2H), 1.56-1.32 (m, 2H), 1.18 (d, 6H), 1.05-0.80 (m, 4H).

Example 14

(S)-4-{(R)-1-Hydroxy-2-[1-(3-isopropyl-phenyl)-cyclopropylamino]-ethyl}-18-oxazol-2-yl-3,15-diaza-tricyclo[14.3.1.1*6,10*]henicosa-1(20),6,8,10(21),16,18-hexaen-2-one The title compound is obtained by an analogous reaction sequence as for example 1, starting from ((1S,2R)-1-(3-allyl-benzyl)-3-{benzyloxycarbonyl-[1-(3-isopropyl-phenyl)-cyclopropyl]amino}-2-hydroxy-propyl)-carbamic acid tert-butyl ester (building block C5) and 3-(allyl-benzyloxycarbonyl-amino)-5-oxazol-2-yl-benzoic acid (building block A3).

MS (ES+): 579=[M+H]+.

HPLC (Nucleosil C18HD, 4×70 mm, 3 μm, 20-100% MeCN (6 min), 100% MeCN (1.5 min)) retention time: 4.54 min.

$^1$H-NMR (400 MHz, DMSO-d$_6$): 8.13 (s, 1H), 7.98 (d, 1H), 7.34 (s, 1H), 7.30 (s, 1H), 7.25-7.09 (m, 5H), 7.09-6.94 (m, 4H), 6.37 (s, 1H), 6-28 (t, 1H), 4.70 (d, 1H), 4.11-3.99 (m, 1H), 3.54-3.44 (m, 1H), 3.41-3.29 (m, 1H), 3.11 (dd, 1H), 3.09-2.95 (m, 1H), 2.88-2.73 (m, 1H), 2.73-2.53 (m, 5H), 1.95-1.85 (m, 1H), 1.85-1.68 (m, 1H), 1.52-1.36 (m, 1H), 1.20-1.05 (m, 6H), 1.04-0.89 (m, 3H), 0.88-0.79 (m, 1H).

Example 15

(S)-4-{(R)-2-[1-(3-tert-Butyl-phenyl)-cyclopropylamino]-1-hydroxy-ethyl}-19-methoxymethyl-11-oxa-3,16-diaza-tricyclo[15.3.1.1*6,10*]docosa-1 (21),6,8,10(22),17,19-hexaen-2-one The title compound is obtained by an analogous reaction sequence as for example 1, starting from ((1S,2R)-1-(3-allyloxy-benzyl)-3-{benzyloxycarbonyl-[1-(3-tert-butyl-phenyl)-cyclopropyl]-amino}-2-hydroxy-propyl)-carbamic acid tert-butyl ester (building block C6) and 3-(allyl-benzyloxycarbonyl-amino)-5-methoxymethyl-benzoic acid (building block A7).

MS (ES+): 586=[M+H]+.

HPLC (Nucleosil C18HD, 4×70 mm, 3 μm, 20-100% MeCN (6 min), 100% MeCN (1.5 min)) retention time: 4.18 min.

$^1$H-NMR (400 MHz, DMSO-d$_6$): 7.91 (d, 1H), 7.31 (s, 1H), 7.20-7.10 (m, 3H), 7.07-6.98 (m, 2H), 6.80-6.68 (m, 2H), 6.60-6.47 (m, 3H), 5.84 (t, 1H) 4.76 (d, 1H), 4.30-4.24 (m, 1H), 4.24 (s, 2H), 3.95-3.80 (m, 2H), 3.53-3.35 (m, 2H), 3.24 (s, 3H), 3.05-2.94 (m, 2H), 2.71-2.45 (m, 3H), 1.81-1.45 (m, 4H), 1.25 (s, 9H), 0.98-0.85 (m, 3H), 0.84-0.77 (m, 1H).

Example 16

(S)-4-{(R)-2-[1-(3-tert-Butyl-phenyl)-cyclopropylamino]-1-hydroxy-ethyl}-19-methoxymethyl-11-oxa-3,16,18-triaza-tricyclo[15.3.1.1*6,10*]docosa-1 (21),6,8,10(22), 17,19-hexaen-2-one The title compound is obtained by an analogous reaction sequence as for example 1, starting from ((1S,2R)-1-(3-allyloxy-benzyl)-3-{benzyloxycarbonyl-[1-(3-tert-butyl-phenyl)-cyclopropyl]-amino}-2-hydroxy-propyl)-carbamic acid tert-butyl ester (building block C6) and 2-allylamino-6-methoxymethyl-isonicotinic acid (building block A1).

MS (ES+): 587=[M+H]+.

HPLC (Nucleosil C18HD, 4×70 mm, 3 μm, 20-100% MeCN (6 min), 100% MeCN (1.5 min)) retention time: 3.53 min.

$^1$H-NMR (400 MHz, DMSO-d$_6$): 8.11 (d, 1H), 7.30 (s, 1H), 7.20-7.10 (m, 3H), 7.05-6.98 (m, 2H), 6.77-6-70 (m, 2H), 6.63 (t, 1H), 6.49 (s, 1H), 6.23 (s, 1H), 4.79 (d, 1H), 4.27-4.21 (m, 1H), 4.21 (s, 2H), 3.95-3.79 (m, 2H), 3.50-3.30 (m, 2H), 3.30 (s, 3H), 3.09-2.94 (m, 2H), 2.66-2.45 (m, H), 2.66-2.45 (m, 3H), 1.82-1.58 (m, 3H), 1.55-1.42 (m, 1H), 1.24 (s, 9H), 0.97-0.86 (m, 3H), 0.86-0.80 (m, 1H).

Example 17

(S)-4-{(R)-2-[1-(3-tert-Butyl-phenyl)-cyclopropylamino]-1-hydroxy-ethyl}-19-(2-oxo-propoxy)-11, 16-dioxa-3-aza-tricyclo[15.3.1.1*6,10*]docosa-1 (21),6,8,10(22), 17,19-hexaen-2-one The title compound is obtained by an analogous reaction sequence as for example 1, starting from ((1S,2R)-1-(3-allyloxy-benzyl)-3-{benzyloxycarbonyl-[1-(3-tert-butyl-phenyl)-cyclopropyl]-amino}-2-hydroxy-propyl)-carbamic acid tert-butyl ester (building block C6) and 3-allyloxy-5-(2-oxo-propoxy)-benzoic acid (building block A2).

Rf (cyclohexane/EtOAc=50/50): 0.14.

MS (ES+): 615=[M+H]+.

$^1$H-NMR (400 MHz, DMSO-d$_6$): 7.97 (d, 1H), 7.33 (s, 1H), 7.20-7.11 (m, 3H), 7.05-6.97 (m, 2H), 6.78 (d, 1H), 6.72 (d, 1H), 6.65 (s, 1H), 6.46 (s, 1H), 4.84 (d, 1H), 4.78 (s, 2H), 4.39-4.29 (m, 1H), 4.26-4.18 (m, 1H), 4.11-4.01 (m 1H), 3.99-3.84 (m, 2H), 3.55-3.46 (m, 1H), 2.95 (d, 1H), 2.67 (t, 1H), 2.62-2.55 (m, 2H), 2.13 (s, 3H), 1.86-1.60 (m, 4H), 1.24 (s, 9H), 0.98-0.79 (m, 4H).

Example 18

(S)-4-{(R)-2-[1-(3-tert-Butyl-phenyl)-cyclopropylamino]-1-hydroxy-ethyl}-19-oxazol-2-yl-11-oxa-3, 16-diaza-tricyclo[15.3.1.1*6,10*]docosa-1 (21),6,8, 10(22),17,19-hexaen-2-one The title compound is obtained by an analogous reaction sequence as for example 1, starting from ((1S,2R)-1-(3-allyloxy-benzyl)-3-{benzyloxycarbonyl-[1-(3-tert-butyl-phenyl)-cyclopropyl]-amino}-2-hydroxy-propyl)-carbamic acid tert-butyl ester (building block C6) and 3-(allyl-benzyloxycarbonyl-amino)-5-oxazol-2-yl-benzoic acid (building block A3).

Rf (DCM/MeOH=95/5): 0.29.

MS (ES+): 609=[M+H]+.

$^1$H-NMR (400 MHz, DMSO-d$_6$): 8.17 (s, 1H), 8.05 (d, 1H), 7.33 (s, 1H), 7.31 (s, 1H), 7.28 (s, 1H), 7.21 (s, 1H), 7.19-7.09 (m, 3H), 7.05-7.00 (m, 2H), 6.78 (d, 1H), 6.72 (dd, 1H), 6.68 (s, 1H), 6.22 (dd, 1H), 4.79 (d, 1H), 4.29-4.21 (m, 1H), 3.97-3.84 (m, 2H), 3.53-3.40 (m, 2H), 3.09-2.95 (m, 2H), 2.70-2.50 (m, 3H), 1.82-1.47 (m, 4H), 1.22 (s, 9H), 0.98-0.78 (m, 4H).

Example 19

(S)-4-{(R)-2-[1-(4-tert-Butyl-pyridin-2-yl)-cyclopropylamino]-1-hydroxy-ethyl}-18-(2-oxo-propoxy)-15-oxa-3-aza-tricyclo[14.3.1.1*6,10*]henicosa-1 (19),6,8, 10(21),16(20),17-hexaen-2-one The title compound is obtained by an analogous reaction sequence as for example 1, starting from [(2R,3S)-4-(3-allyl-phenyl)-3-tert-butoxycarbonylamino-2-hydroxy-butyl]-[1-(4-tert-butyl-pyridin-2-yl)-cyclopropyl]-carbamic acid benzyl ester (building block C8) and 3-allyloxy-5-(2-oxo-propoxy)-benzoic acid (building block A2).

Rf (DCM/MeOH/NH$_3$=90/10/1): 0.47.

MS (LC/MS, ES+): 600=[M+H]+.

$^1$H-NMR (400 MHz, DMSO-d$_6$): 8.33 (d, 1H), 8.03 (d, 1H), 7.77 (s, 1H), 7.41 (s, 1H), 7.17-7.10 (m, 2H), 7.07 (d,

1H), 6.99 (d, 1H), 6.56 (s, 1H), 6.41 (s, 1H), 6.37 (s, 1H), 5.03 (d, 1H), 4.75 (s, 2H), 4.34-4.27 (m, 1H), 4.15-4.04 (m, 2H), 3.64-3.60 (m, 1H), 3.14 (dd, 1H), 2.75-2.60 (m, 6H), 2.11 (s, 3H), 1.96-1.78 (m, 2H), 1.53-1.3 (m, 2H), 1.27 (s, 9H), 1.26-1.17 (m, 2H), 1.06-0.98 (m, 2H).

Example 20

(S)-4-{(R-2-[1-(4-tert-Butyl-pyridin-2-yl)-cyclopropylamino]-1-hydroxy-ethyl}-18-oxazol-2-yl-3,15-diaza-tricyclo[14.3.1.1*6,10*]henicosa-1(19),6,8,10(21),16(20), 17-hexaen-2-one The title compound is obtained by an analogous reaction sequence as for example 1, starting from [(2R,3S)-4-(3-allyl-phenyl)-3-tert-butoxycarbonylamino-2-hydroxy-butyl]-[1-(4-tert-butyl-pyridin-2-yl)-cyclopropyl]-carbamic acid benzyl ester (building block C8) and 3-(allyl-benzyloxycarbonyl-amino)-5-oxazol-2-yl-benzoic acid (building block A3).

Rf (DCM/MeOH/NH$_3$=90/10/1): 0.36.
MS (LC/MS, ES+): 594=[M+H]$^+$.
$^1$H-NMR (400 MHz, DMSO-d$_6$): 8.32 (d, 1H), 8.16 (s, 1H), 8.09 (d, 1H), 7.77 (s, 1H), 7.41 (s, 1H), 7.33 (s, 1H), 7.22 (s, 2H), 7.18 (t, 1H), 7.12-7.07 (m, 2H), 7.01 (d, 1H), 6.42 (s, 1H), 6.33 (t, 1H), 4.99 (d, 1H), 4.15-4.06 (m, 1H), 3.62-3.57 (m, 1H), 3.19-3.15 (m, 1H), 3.07-2.98 (m, 1H), 1.78-2.64 (m, 6H), 1.97-1.74 (m, 2H), 1.50-1.40 (m, 1H), 1.30-1.09 (m, 3H), 1.23 (s, 9H), 1.08-0.98 (m, 2H).

Example 21

Propane-1-sulfonic acid ((S)-4{(R)-1-hydroxy-2-[1-(3-isopropyl-phenyl)-cyclopropylamino]-ethyl}-2-oxo-11-oxa-3,16-diaza-tricyclo[15.3.1.1*6,10*]docosa-1(21),6,8,10(22),17,19-hexaen-19-yl)-methyl-amide The title compound is obtained by an analogous reaction sequence as for example 1, starting from ((1S,2R)-1-(3-allyloxy-benzyl)-3-{benzyloxycarbonyl-[1-(3-isopropyl-phenyl)-cyclopropyl]-amino}-2-hydroxy-propyl)-carbamic acid tert-butyl ester (building block C7) and 3-(allyl-benzyloxycarbonyl-amino)-5-[methyl-(propane-1-sulfonyl)-amino]-benzoic acid (building block A13).

MS (ES+): 663=[M+H]$^+$
HPLC (Nucleosil C18HD, 4×70 mm, 3 μm, 20-100% MeCN (6 min), 100% MeCN (1.5 min)) retention time=4.43 min
$^1$H-NMR (400 MHz, DMSO-d$_6$): 8.01 (d, 1H), 7.25-7.00 (m, 6H), 6.83 (d, 1H), 6.77 (d, 1H), 6.67 (s, 2H), 6.55 (s, 1H), 6.07 (t, 1H), 4.84 (d, 1H), 4.32-4.24 (m, 1H), 4.00-3.87 (m, 2H), 3.68-3.48 (m, 1H), 3.55-3.39 (m, 2H), 3.16 (s, 3H), 3.10-2.92 (m, 4H), 2.90-2.80 (m, 1H), 2.75-2.68 (m, 1H), 2.65-2.45 (m, 2H), 1.82-1.50 (m, 6H), 1.19 (d, 6H), 0.96 (t, 3H), 1.00-0.78 (m, 4H).

Example 22

(S)-19-Acetyl-4-{(R)-2-[1-(3-tert-butyl-phenyl)-cyclopropylamino]-1-hydroxy-ethyl}-11,16-dioxa-3-aza-tricyclo[15.3.1.1*6,10*]docosa-1(21),6,8,10(22),17,19-hexaen-2-one The title compound is obtained by an analogous reaction sequence as for example 1, starting from ((1S,2R)-1-(3-allyloxy-benzyl)-3-benzyloxycarbonyl-[1A3-tert-butyl-phenyl)-cyclopropyl]-amino}-2-hydroxy-propyl)-carbamic acid tert-butyl ester (building block C6) and 3-acetyl-5-allyloxy-benzoic acid (building block A6).

MS (ES+): 585=[M+H]$^+$
HPLC (Nucleosil C18HD, 4×70 mm, 3 μm, 20-100% MeCN (6 min), 100% MeCN (1.5 min)) retention time=4.75 min
$^1$H-NMR (400 MHz, DMSO-d$_6$): 8.11 (d, 1H), 7.57 (s, 1H), 7.45 (s, 1H), 7.31 (s, 1H), 7.25 (s, 1H), 7.20-7.09 (m, 3H), 7.04-6.94 (m, 2H), 6.79 (d, 1H), 6.72 (d, 1H), 4.84 (d, 1H), 4.46-4.30 (m, 1H), 4.25-4.11 (m, 2H), 4.00-3.88 (m, 2H), 3.52-3.49 (m, 1H), 3.00-2.90 (m, 1H), 2.70-2.45 (m, 3H), 2.49 (s, 3H), 1.86-1.60 (m, 4H), 1.22 (s, 9H), 0.98-0.78 (m, 4H).

Example 23

Propane-1-sulfonic acid ((S)-4-{(R)-1-hydroxy-2-[1-(3-isopropyl-phenyl)-cyclopropylamino]-ethyl}-2-oxo-11,16-dioxa-3-aza-tricyclo[15.3.1.1*6,10*]docosa-1(21),6,8,10(22),17,19-hexaen-19-yl)-methyl-amide The title compound is obtained by an analogous reaction sequence as for example 1, starting from ((1S,2R)-1-(3-allyloxy-benzyl)-3{benzyloxycarbonyl-[1-(3-tert-butyl-phenyl)-cyclopropyl]-amino}-2-hydroxy-propyl)-carbamic acid tert-butyl ester (building block C7) and 3-allyloxy-5-[methoxy-(propane-1-sulfonyl)amino]-benzoic acid allyl ester (building block A9).

MS (ES+): 663=[M+H]$^+$
HPLC (Nucleosil C18HD, 4×70 mm, 3 μm, 20-100% MeCN (6 min), 100% MeCN (1.5 min)) retention time=4.66 min
$^1$H-NMR (400 MHz, DMSO-d$_6$): 8.10 (d, 1H), 7.20-6.95 (m, 9H), 6.81 (d, 1H), 6.75 (d, 1H), 4.89 (d, 1H), 4.39-4.32 (m, 1H), 4.28-4.20 (m, 1H), 4.12-4.08 (m, 1H), 4.00-3.88 (m, 2H), 3.68-3.48 (m, 1H), 3.55-3.50 (m, 3H), 3.21 (s, 3H), 3.10-3.05 (m, 2H), 2.92 (d, 1H), 2.84-2.74 (m, 1H), 2.69 (t, 1H), 2.57-2.50 (m, 2H), 1.85-1.60 (m, 6H), 1.19 (d, 6H), 0.94 (t, 3H), 1.00-0.77 (m, 4H).

Example 24

(S)-4-{(R)-2-[1-(4-tert-Butyl-pyridin-2-yl)-cyclopropylamino]-1-hydroxy-ethyl}-19-methyl-11,16-dioxa-3,18-diaza-tricyclo[15.3.1.1*6,10*]docosa-1(21),6,8,10(22),17,19-hexaen-2-one a) 2-[4-(3-{(2S,3R)-2-tert-Butoxycarbonylamino-4-[1-(4-tert-butyl-pyridin-2-yl)-cyclopropylamino]-3-hydroxy-butyl}-phenoxy)-butoxy]-6-methyl-isonicotinic acid methyl ester The product is prepared according to the method described in example 43 (step a), starting from [(1S,2R)-3-[1-(4-tert-butyl-pyridin-2-yl)cyclopropylamino]-2-hydroxy-1-(3-hydroxy-benzyl)-propyl]-carbamic acid tert-butyl ester (building block C16) and 2-(4-methanesulfonyloxy-butoxy)-6-methyl-isonicotinic acid methyl ester (building block E1).
Rf: DCM/MeOH/25% aq NH$_3$ 90/9/1): 0.24
HPLC (Zorbax SB-C18, 3×30 mm, 1.8 μm, 50-100% MeCN (3.25 min), 100% MeCN (0.75 min)): 2.775 min
MS (ES+): 691=[M+H]$^+$ b) (S)-4-{(R)-2-[1-(4-tert-Butyl-pyridin-2-yl)-cyclopropylamino]-1-hydroxy-ethyl}-19-methyl-11,16-dioxa-3,18-diaza-tricyclo[15.3.1.1*6,10*]docosa-1 (21),6,8,10(22),17,19-hexaen-2-one A solution of 60 mg (0.0868 mmol) 2-[4-(3-{(2S,3R)-2-tert-butoxycarbonylamino-4-[1-(4-tert-butyl-pyridin-2-yl)-cyclopropylamino]-3-hydroxy-butyl}-phenoxy)-butoxy]-6-methyl-isonicotinic acid methyl ester is treated with 0.17 ml 1N aq sodium hydroxide and stirred for 18 h. The mixture is acidified with 0.17 ml 1N aq hydrochloric acid and evaporated. The residue is taken up into 3 ml 4N hydrochloric acid in dioxan, stirred for 2 h and evaporated. The product is taken up in 20 ml DCM. To the stirred mixture at +4° C. is added subsequently 22.3 mg (0.13 mmol) HOBt, 25 mg (1.5 mmol) EDC and 0.048 ml N-methylmorpholine. The mixture is slowly warmed to rt and stirred 18 h. Water is added and the organic phase is washed with 5% aq sodium bicarbonate and brine, dried over sodium sulfate and chromatographed on silica gel using a gradient of DCM and MeOH/25% aq NH$_3$ 2-10%. The title compound is obtained as a colorless resin.
Rf: (DCM/MeOH/25% aq NH$_3$ 90/9/1): 0.35
HPLC (Zorbax SB-C18, 3×30 mm, 1.8 μm, 30-100% MeCN (3.25 min), 100% MeCN (0.75 min)): 2.264 min
MS (ES+): 559=[M+H]$^+$ Example 25

(S)-4{(R)-1-Hydroxy-2-[1-(3-isopropyl-phenyl)-cyclopropylamino]-ethyl}-2-oxo-11-oxa-3,16-diaza-tricyclo[15.3.1.1*6,10*]docosa-1(21),6,8,10(22),17,19-hexaene-19-carboxylic acid dimethylamide The title compound is obtained by an analogous reaction sequence as for example 1, starting from ((1S,2R)-1-(3-allyloxy-benzyl)-3-{benzyloxycarbonyl-[1-(3-tert-butyl-phenyl)-cyclopropyl]-amino}-2-hydroxy-propyl)-carbamic acid tert-butyl ester (building block C7) and 5-(allyl-benzyloxycarbonyl-amino)-N,N-dimethyl-isophtalamic acid (building block A15).
MS (ES+): 599=[M+H]$^+$
HPLC (Nucleosil C18HD, 4×70 mm, 3 μm, 20-100% MeCN (6 min), 100% MeCN (1.5 min)) retention time=3.82 min
$^1$H-NMR (400 MHz, DMSO-d$_6$): 7.99 (d, 1H), 7.18-7.09 (m, 3H), 7.08-6.96 (m, 3H), 6.80-6.70 (m, 2H), 6.59 (s, 2H), 6.51 (s, 1H), 6.02 (t, 1H), 4.76 (d, 1H), 4.30-4.20 (m, 1H), 3.96-3.82 (m, 2H), 3.50-3.35 (m, 2H), 3.08-2.75 (m, 9H), 2.70-2.48 (m, 3H), 1.82-1.45 (m, 4H), 1.18 (d, 6H), 0.96-0.73 (m, 4H).

Example 26

(S)-4-{(R)-1-Hydroxy-2-[1-(3-isopropyl-phenyl)-cyclopropylamino]-ethyl}-19-methoxy-11-oxa-3,16-diaza-tricyclo[15.3.1.1*6,10*]docosa-1(21),6,8,10(22),17,19-hexaen-2-one The title compound is obtained by an analogous reaction sequence as for example 1, starting from ((1S,2R)-1-(3-allyloxy-benzyl)-3-{benzyloxycarbonyl-[1-(3-tert-butyl-phenyl)-cyclopropyl]-amino}-2-hydroxy-propyl)-carbamic acid tert-butyl ester (building block C7) and 3-(allyl-benzyloxycarbonyl-amino)-5-methoxy-benzoic acid (building block A14).
MS (ES+): 558=[M+H]$^+$
HPLC (Nucleosil C18HD, 4×70 mm, 3 μm, 20-100% MeCN (6 min), 100% MeCN (1.5 min)) retention time=4.09 min
$^1$H-NMR (400 MHz, DMSO-d$_6$): 7.87 (d, 1H), 7.18-7.10 (m, 3H), 7.05 (d, 1H), 7.03-6.95 (m, 2H), 6.77 (d, 1H), 6.71 (d, 1H), 6.24 (s, 1H), 6.19 (s, 2H), 5.82 (t, 1H), 4.77 (d, 1H), 4.28-4.20 (d, 1H), 3.95-3.80 (m, 2H), 3.64 (s, 3H), 3.52-3.32 (m, 2H), 3.03-2.92 (m, 2H), 2.88-2.78 (m, 1H), 2.70-2.62 (m, 1H), 2.60-2.47 (m, 2H), 1.82-1.47 (m, 4H), 1.19 (d, 6H), 0.97-0.82 (m, 4H).

Example 27

(S)-4-{(R)-1-Hydroxy-2-[1-(3-isopropyl-phenyl)-cyclopropylamino]-ethyl}-19-(2-oxo-propoxy)-11-oxa-3,16-diaza-tricyclo[15.3.1.1*6,10*]docosa-(21),6,8,10(22),17,19-hexaen-2-one The title compound is obtained by an analogous reaction sequence as for example 1, starting from ((1S,2R)-1-(3-allyloxy-benzyl)-3-{benzyloxycarbonyl-[1-(3-tert-butyl-phenyl)-cyclopropyl]-amino}-2-hydroxy-propyl)-carbamic acid tert-butyl ester (building block C7) and 3-(allyl-benzyloxycarbonyl-amino)-5-(2-oxo-propoxy)-benzoic acid (building block A12).
MS (ES+): 600=[M+H]$^+$
HPLC (Nucleosil C18HD, 4×70 mm, 3 μm, 20-100% MeCN (6 min), 100% MeCN (1.5 min)) retention time=4.07 min
$^1$H-NMR (400 MHz, DMSO-d$_6$): 7.89 (d, 1H), 7.19-7.11 (m, 3H), 7.18-6.97 (m, 3H), 6-78 (d, 1H), 6.72 (d, 1H), 6.26 (s, 1H), 6.17-4.11 (m, 2H), 5.82 (t, 1H), 4.78 (d, 1H), 4.63 (m, 2H), 4.29-4.20 (m, 1H), 3.96-3.81 (m, 2H), 3.53-3.32 (m, 2H), 3.04-2.92 (m, 2H), 2.89-2.79 (m, 1H), 2.71-2.61 (m, 1H), 2.61-2.48 (m, 2H), 2.12 (s, 3H), 1.81-1.47 (m, 4H), 1.19 (d, 6H), 0.97-0.78 (m, 4H).

Example 28

(S)-19-Acetyl-4{(R)-2-[1-(3-tert-butyl-phenyl)-cyclopropylamino]-1-hydroxy-ethyl}-11-oxa-3,16-diaza-tricyclo[15.3.1.1*6,10*]docosa-1 (21),6,8,10 (22),17,19-hexaen-2-one The title compound is obtained by an analogous reaction sequence as for example 1, starting from ((1S,2R)-1-(3-allyloxy-benzyl)-3-{benzyloxycarbonyl-[1-(3-tert-butyl-phenyl)-cyclopropyl]-amino}-2-hydroxy-propyl)-carbamic acid tert-butyl ester (building block C6) and 3-acetyl-5-(allyl-benzyloxycarbonyl-amino)-benzoic acid (building block A5).
MS (ES+): 584=[M+H]$^+$
HPLC (Nucleosil C18HD, 4×70 mm, 3 μm, 20-100% MeCN (6 min), 100% MeCN (1.5 min)) retention time=4.38 min
$^1$H-NMR (400 MHz, DMSO-d$_6$): 8.02 (d, 1H), 7.30 (s, 1H), 7.20-7.07 (s, 5H), 7.05-6.95 (m, 2H), 6.82-6.68 (m, 3H), 6.14 (t, 1H), 4.80 (d, 1H), 4.28-4.17 (m, 1H), 3.95-3.74 (m, 2H), 3.55-3.35 (m, 2H), 3.08-2.90 (m, 2H), 2.70-2.42 (m, 3H), 2.45 (s, 3H), 1.80-1.44 (m, 4H), 1.23 (s, 9H), 0.97-0.76 (m, 4H).

Example 29

(S)-4-{(R)-1-Hydroxy-2-[1-(3-isopropyl-phenyl)-cyclopropylamino]-ethyl}-18-methoxymethyl-11,15-dioxa-3-aza-tricyclo[14.3.1.1*6,10*]henicosa-1(20),6,8,10(21),16,18-hexaen-2-one The title compound is obtained by an analogous reaction sequence as for example 50, starting from [(2R,3S)-4-(3-benzyloxy-phenyl)-3-tert-butoxycarbonylamino-2-hydroxy-butyl]-[1-(3-isopropyl-phenyl)-cyclopropyl]-carbamic acid tert-butyl ester and 3-(3-methanesulfonyloxy-propoxy)-5-methoxymethyl-benzoic acid methyl ester (building block E3).

MS (ES+): 559=[M+H]$^+$

HPLC (Nucleosil C18HD, 4×70 mm, 3 μm, 20-100% MeCN (6 min), 100% MeCN (1.5 min)) retention time=4.37 min $^1$H-NMR (400 MHz, DMSO-d$_6$): 7.95 (d, 1H), 7.21-7.12 (m, 4H), 7.07 (d, 1H), 7.01 (d, 1H), 6.92-6.86 (m, 2H), 6.82-6.78 (m, 2H), 6.55 (s, 1H), 4.71 (d, 1H), 4.54 (ddd, 1H), 4.40 (ddd, 1H), 4.31 (s, 2H), 4.25-4.08 (m, 2H), 4.03-3.90 (m, 1H), 3.55-3.43 (m, 1H), 3.24 (s, 3H), 3.12 (dd, 1H), 2.90-2.70 (m, 1H), 2.61-2.50 (m, 3H), 2.04-1.85 (m, 1H), 1.83-1.68 (m, 1H), 1.17 (d, 6H), 1.05-0.80 (m, 4H).

Example 30

(S)-4-{(R)-1-Hydroxy-2-[1-(3-isopropyl-phenyl)-cyclopropylamino]-ethyl}-19-methoxymethyl-11,16-dioxa-3,18-diaza-tricyclo[15.3.1.1*6,10*]docosa-1(21),6,8,10(22),17,19-hexaen-2-one The title compound is obtained by an analogous reaction sequence as for example 1, starting from ((1S,2R)-1-(3-allyloxy-benzyl)-3-{benzyloxycarbonyl-[1-(3-isopropyl-phenyl)-cyclopropyl]-amino}-2-hydroxy-propyl)-carbamic acid tert-butyl ester (building block C7) and 2-allyloxy-6-methoxymethyl-isonicotinic acid (building block A11).

MS (ES+): 574=[M+H]$^+$

HPLC (Nucleosil C18HD, 4×70 mm, 3 μm, 20-100% MeCN (6 min), 100% MeCN (1.5 min)) retention time=4.17 min

Example 31

(S)-4-((R)-2-{1-[5-(2,2-Dimethyl-propyl)-isoxazol-3-yl]-cyclopropylamino]-ethyl}-1-hydroxy-ethyl)-19-methoxymethyl-11-oxa-3,16-diaza-tricyclo[15.3.1.1*6,10*]docosa-1(21),6,8,10(22),17,19-hexaen-2-one The title compound is obtained by an analogous reaction sequence as for example 1, starting from [(2R,3S)-4-(3-allyloxy-phenyl)-3-tert-butoxycarbonylamino-2-hydroxy-butyl]-{1-[5-(2,2-dimethyl-propyl)-isoxazol-3-yl]-cyclopropyl}-carbamic acid benzyl ester (building block C19) and 3-(allyl-benzyloxycarbonyl-amino)-5-methoxymethyl-benzoic acid (building block A7).

MS (ES+): 591=[M+H]$^+$

HPLC (Nucleosil C18HD, 4×70 mm, 3 μm, 20-100% MeCN (6 min), 100% MeCN (1.5 min)) retention time=3.85 min $^1$H-NMR (400 MHz, DMSO-d$_6$): 7.95 (d, 1H), 7.15 (t, 1H), 7.03 (s, 1H), 6.79 (d, 1H), 6.71 (d, 1H), 6.60 (s, 1H), 6.59 (s, 1H), 6.53 (s, 1H), 6.16 (s, 1H), 5.86 (t, 1H), 4.76 (d, 1H), 4.24 (s, 2H), 3.94-3.82 (m, 2H), 3.46-3.34 (m, 2H), 3.24 (s, 3H), 3.04-2.93 (m, 2H), 2.78-2.70 (m, 1H), 2.70-2.58 (m, 3H), 2.54 (s, 2H), 1.76-1.45 (m, 4H), 1.05-0.76 (m, 4H), 0.87 (s, 9H).

Example 32

(S)-4-{(R)-1-Hydroxy-2-[1-(4-isopropyl-pyridin-2-yl)-cyclopropylamino]-ethyl}-18-methoxymethyl-3,15,17-triaza-tricyclo[14.3.1.1*6,10*]henicosa-1(20),6,8,10(21),16,18-hexaen-2-one The title compound is obtained by an analogous reaction sequence as for example 1, starting from [(2R,3S)-4-(3-allyl-phenyl)-3-tert-butoxycarbonylamino-2-hydroxy-butyl]-[1-(4-isopropyl-pyridin-2-yl)-cyclopropyl]-carbamic acid benzyl ester (building block C12) and 2-allylamino-6-methoxymethyl-isonicotinic acid (building block A1).

MS (ES+): 558=[M+H]$^+$

HPLC (Nucleosil C18HD, 4×70 mm, 3 μm, 20-100% MeCN (6 min), 100% MeCN (1.5 min)) retention time=3.27 min $^1$H-NMR (400 MHz, DMSO-d$_6$): 8.28 (d, 1H), 8.11 (d, 1H), 7.55 (s, 1H), 7.35 (s, 1H), 7.20-6.90 (m, 4H), 6.72-4.65 (m, 1H), 6.53 (s, 1H), 5.98 (s, 1H), 4.92 (d, 1H), 4.21 (s, 2H), 4.15-4.05 (m, 1H), 4.00-3.85 (m, 1H), 3.60-3.50 (m, 1H), 3.32 (s, 3H), 3.24-2.95 (m, 3H), 2.92-2.78 (m, 1H), 2.75-2.60 (m, 4H), 2.00-1.88 (m, 1H), 1.82-1.70 (m, 1H), 1.43-1.10 (m, 8H), 1.09-0.82 (m, 4H).

Example 33

(S)-4-{(R)-1-Hydroxy-2-[1-(4-isopropyl-pyridin-2-yl)-cyclopropylamino]ethyl}-19-methoxymethyl-18-oxa-3,16,18-triaza-tricyclo[15.3.1.1*6,10*]docosa-1(21),6,8,10(22),17,19-hexaen-2-one The title compound is obtained by an analogous reaction sequence as for example 1, starting from [(2R,3S)-4-(3-allyloxy-phenyl)-3-tert-butoxycarbonylamino-2-hydroxy-butyl]-[1-(4-isopropyl-pyridin-2-yl)-cyclopropyl]-carbamic acid benzyl ester (building block C11) and 2-allylamino-6-methoxymethyl-isonicotinic acid (building block A1).

MS (ES+): 574=[M+H]$^+$

HPLC (Nucleosil C18HD, 4×70 mm, 3 μm, 20-100% MeCN (6 min), 100% MeCN (1.5 min)) retention time=3.14 min $^1$H-NMR (400 MHz, DMSO-d$_6$): 8.29 (d, 1H), 8.16 (d, 1H), 7.51 (s, 1H), 7.16 (m, 1H), 7.04 (s, 1H), 6.96 (d, 1H), 6.79 (d, 1H), 6.72 (d, 1H), 6.64 (t, 1H), 6.51 (s, 1H), 6.26 (s, 1H), 4.95 (d, 1H), 4.26-4.22 (m, 1H), 4.22 (s, 2H), 3.96-3.85 (m, 2H), 3.58-3.50 (m, 1H), 3.50-3.35 (m, 1H), 3.32 (s, 3H), 3.10-2.98 (m, 2H), 2.88-2.80 (m, 1H), 2.73-2.58 (m, 4H), 1.80-1.62 (m, 3H), 1.58-1.44 (m, 1H), 1.28-1.04 (m, 4H), 1.17 (d, 6H).

Example 34

(S)-18-Acetyl-4{(R)-2-[1-(4-tert-butyl-pyridin-2-yl)-cyclopropylamino]-1-hydroxy-ethyl}-3,15-diaza-tricyclo[14.3.1.1*6,10*]henicosa-1(20),6,8,10(21),16,18-hexaen-2-one The title compound is obtained by an analogous reaction sequence as for example 1, starting from [(2R,3S)-4-(3-allyl-phenyl)-3-tert-butoxycarbonylamino-2-hydroxy-butyl]-[1-(4-tert-butyl-pyrid-2-yl)-cyclopropyl]-carbamic acid benzyl ester (building block C8) and 3-acetyl-5-(allyl-benzyloxycarbonyl-amino)-benzoic acid (building block A5).

MS (ES+): 569=[M+H]$^+$

HPLC (Nucleosil C18HD, 4×70 mm, 3 μm, 20-100% MeCN (6 min), 100% MeCN (1.5 min)) retention time=4.32 min $^1$H-NMR (400 MHz, DMSO-d$_6$): 8.31 (d, 1H), 8.05 (d, 1H), 7.71 (s, 1H), 7.38 (s, 1H), 7.18-7.02 (m, 5H), 6.98 (d, 1H), 6.52 (s, 1H), 6.21 (t, 1H), 4.99 (d, 1H), 4.13-4.06 (m, 1H), 3.62-3.59 (s, 1H), 3.12 (d, 1H), 3.05-2.97 (m, 1H), 2.79-2.59 (m, 6H), 2.43 (s, 3H), 1.95-1.85 (m, 1H), 1.81-1.70 (m, 1H), 1.49-1.38 (m, 1H), 1.26 (s, 9H), 1.30-1.00 (m, 5H).

Example 35

(S)-4-[(R)-1-Hydroxy-2-(2-phenyl-cyclopropylamino)-ethyl]-19-methoxymethyl-11-oxa-3,16-diaza-tricyclo[15.3.1.1*6,10*]docosa-1 (21),6,8,10 (22),17,19-hexaen-2-one The title compound is obtained as mixture of two epimers by an analogous reaction sequence as for example 1, starting from [(2R,3S)-4-(3-allyloxy-phenyl)-3-tert-butoxycarbonylamino-2-hydroxy-butyl]-(2-phenyl-cyclopropyl)-carbamic acid benzyl ester (building block C20) and 3-(allyl-benzyloxycarbonyl-amino)-5-methoxymethyl-benzoic acid (building block A7).

$^1$H-NMR (400 MHz, DMSO-d$_6$): 8.02-7.90 (m, 1H), 7.22-6.99 (m, 7H), 6.81-6.69 (m, 2H), 6.62-6.49 (m, 3H), 5.91-5.82 (m, 1H), 4.92-4.81 (m, 1H), 4.28-4.22 (m, 3H), 3.95-3.80 (m, 2H), 3.50-3.35 (m, 2H), 3.25 (s, 3H), 3.03-2.92 (m, 2H), 2.76-2.59 (m, 3H), 2.28-2.24 (m, 1H), 1.85-1.15 (m, 5H), 1.00-0.85 (m, 2H).

Example 36

(S)-4-{(R)-1-Hydroxy-2-[1-(3-propyl-isoxazol-5-yl)-cyclopropylamino]-ethyl}-19-methoxymethyl-11-oxa-3,16-diaza-tricyclo[15.3.1.1*6,10*]docosa-1 (21),6,8,10(22),17,19-hexaen-2-one The title compound is obtained by an analogous reaction sequence as for example 1, starting from [(2R,3S)-4-(3-allyloxy-phenyl)-3-tert-butoxycarbonylamino-2-hydroxy-butyl]-{1-[5-(2,2-dimethyl-propyl)-isoxazol-3-yl]-cyclopropyl}-carbamic acid benzyl ester (building block C19) and 3-(allyl-benzyloxycarbonyl-amino)-5-methoxymethyl-benzoic acid (building block A7).

MS (ES+): 563=[M+H]$^+$

HPLC (Nucleosil C18HD, 4×70 mm, 3 μm, 20-100% MeCN (6 min), 100% MeCN (1.5 min)) retention time=3.27 min Example 37

(S)-19-Acetyl-4-{(R)-2-[1-(4-tert-butyl-pyridin-2-yl)-cyclopropylamino]-1-hydroxy-ethyl}-11-oxa-3,16-diaza-tricyclo[15.3.1.1*6,10*]docosa-1 (21),6,8,10(22),17,19-hexaen-2-one The title compound is obtained by an analogous reaction sequence as for example 1, starting from [(2R,3S)-4-(3-allyloxy-phenyl)-3-tert-butoxycarbonylamino-2-hydroxy-butyl]-[1-(4-tert-butyl-pyridin-2-yl)-cyclopropyl]-carbamic acid benzyl ester (building block C18) and 3-acetyl-5-(allyl-benzyloxycarbonyl-amino)-benzoic acid (building block A5).

MS (ES+): 585=[M+H]$^+$

HPLC (Nucleosil C18HD, 4×70 mm, 3 μm, 20-100% MeCN (6 min), 100% MeCN (1.5 min)) retention time=4.10 min $^1$H-NMR (400 MHz, DMSO-d$_6$): 8.28 (d, 1H), 8.06 (d, 1H), 7.68 (s, 1H), 7.19 (s, 1H), 7.17-7.13 (m, 2H), 7.09-7.05 (m, 2H), 6.84-6.78 (m, 2H), 6.72 (d, 1H), 6.14 (t, 1H), 4.99 (d, 1H), 4.30-4.21 (m, 1H), 3.96-3.87 (m, 2H), 3.61-3.54 (m, 1H), 3.51-3.40 (m, 1H), 3.07-2.97 (m, 2H), 2.74-2.55 (m, 4H), 2.44 (s, 3H), 1.80-1.42 (m, 4H), 1.25-1.10 (m, 2H), 1.21 (s, 9H), 1.02-0.93 (m, 2H).

Example 38

(S)-4-{(R)-2-[1-(4-tert-Butyl-pyridin-2-yl)-cyclopropylamino]-1-hydroxy-ethyl}-19-methoxy-11-oxa-3,16-diaza-tricyclo[15.3.1.1*6,10*]docosa-1(21),6,8,10(22),17,19-hexaen-2-one The title compound is obtained by an analogous reaction sequence as for example 1, starting from [(2R,3S)-4-(3-allyloxy-phenyl)-3-tert-butoxycarbonylamino-2-hydroxy-butyl]-[1-(4-tert-butyl-pyridin-2-yl)-cyclopropyl]-carbamic acid benzyl ester (building block C18) and 3-(allyl-benzyloxycarbonyl-amino)-5-methoxy-benzoic acid (building block A14).

MS (ES+): 573=[M+H]$^+$

HPLC (Nucleosil C18HD, 4×70 mm, 3 μm, 20-100% MeCN (6 min), 100% MeCN (1.5 min)) retention time=3.97 min $^1$H-NMR (400 MHz, DMSO-d$_6$): 8.28 (d, 1H), 7.90 (d, 1H), 7.69 (s, 1H), 7.17-7.03 (m, 3H), 6.79 (d, 1H), 6.71 (d, 1H), 6.25 (s, 1H), 6.18-6.16 (m, 2H), 5.82 (t, 1H), 4.98 (d, 1H), 4.30-4.24 (m, 1H), 3.94-3.83 (m, 2H), 3.62 (s, 3H), 3.60-3.52 (m, 1H), 3.49-3.35 (m, 1H), 3.04-2.92 (m, 2H), 2.74-2.52 (m, 4H), 1.80-1.45 (m, 4H), 1.27 (s, 9H), 1.28-1.10 (m, 2H), 1.03-0.92 (m, 2H).

Example 39

(E)-(S)-4-{(R)-2-[1-(3-tert-Butyl-phenyl)-cyclopropylamino]-1-hydroxy-ethyl}-9-fluoro-19-methyl-1-oxa-3,16,18-triaza-tricyclo[15.3.1.1*6,10*]docosa-1 (21),6,8,10(22),13,17,19-heptaen-2-one a) [(R)-2-((E)-(S)-16-Acetyl-9-fluoro-19-methyl-2-oxo-11-oxa-3,16,18-triaza-tricyclo[15.3.1.1*6,10*] docosa-1(21),6,8,10(22),13,17,19-heptaen-4-yl)-2-hydroxy-ethyl]-[1-(3-tert-butyl-phenyl)-cyclopropyl]-carbamic acid benzyl ester The title compound is obtained by an analogous reaction sequence (steps a and b) as for example 1, starting from [(2R,3S)-4-(3-allyloxy-4-fluoro-phenyl)-3-tert-butoxycarbonylamino-2-hydroxy-butyl]-[1-(2-tert-butyl-phenyl)-cyclopropyl]-carbamic acid benzyl ester (building block C10) and 2-(acetyl-allyl-amino)-6-methyl-isonicotinic acid (building block A17).

Rf (EtOAc): 0.30.

MS (ES+): 749.3=[M+H]$^+$.

$^1$H-NMR (400 MHz, DMSO-d$_6$, 121° C.): 7.94 (d, 1H), 7.26-7.13 (m, 8H), 7.01 (d, 1H), 6.95 (dd, 1H), 6.88 (d, 1H), 6.81-6.77 (m, 1H), 5.90-5.84 (m, 1H), 5.70-5.63 (m, 1H), 5.09 (dd, 2H), 4.77-4.66 (m, 2H), 4.53-4.46 (m, 1H), 4.13 (dd, 1H), 4.06-3.94 (m, 2H), 3.76 (dd, 1H), 3.32 (dd, 1H), 3.11-

3.06 (m, 1H), 2.77-2.70 (m, 1H), 2.46 (s, 3H), 2.00 (s, 3H), 1.81-1.75 (m, 1H), 1.54-1.47 (m, 1H), 1.34-1.19 (m, 3H), 1.23 (s, 9H), 1.13-1.08 (m, 1H), 0.90-0.83 (m, 1H).

b) (E)-(S)-4{(R)-2-[1-(3-tert-Butyl-phenyl)-cyclopropylamino]-1-hydroxy-ethyl}-9-fluoro-19-methyl-11-oxa-3,16,18-triaza-tricyclo[15.3.1.1*6,10*] docosa-1 (21),6,8,10(22),13,17,19-heptaen-2-one To a solution of [(R)-2-((E)-(S)-16-acetyl-9-fluoro-19-methyl-2-oxo-11-oxa-3,16,18-triaza-tricyclo[15.3.1.1*6, 10*]docosa-1(21),6,8,10(22),13,17,19-heptaen-4-yl)-2-hydroxy-ethyl]-[1-(3-tert-butyl-phenyl)-cyclopropyl]-carbamic acid benzyl ester (35 mg, 0.047 mmol) in 2 ml DCM is added iodotrimethylsilane (137 µl, 0.935 mmol) and the mixture is stirred for 10 min. Excess iodotrimethylsilane is destroyed by addition of 1 ml MeOH, the reaction mixture is diluted with 10 ml water, basified by addition of 2 ml 14N aq ammonia and extracted with DCM. The combined organic layers are dried over sodium sulfate and evaporated. The residue is dissolved in 1 ml EtOH, 2N sodium hydroxide (100 µl, 0.2 mmol) is added and the mixture is stirred for 20 h. After heating at 60° C. for 110 min the reaction mixture is cooled to 0° C. and 500 µl 0.5M hydrochloric acid are added. The organic solvent is separated, the aqueous solution basified by addition of 1 ml 1M potassium hydrogencarbonate and extracted with DCM. The combined organic layers are dried over sodium sulfate and evaporated, the residue is purified by preparative thin layer chromatography (DCM/MeOH/ $NH_3$=95/4.5/0.5) to give the product as colorless solid.

HPLC (Waters SunFire C18, 5 µm, 4.6×150 mm, 30-100% MeCN (3 min), 100% MeCN (2.0 min), 1.5 ml/min) retention time: 1.70 min.

MS (ES+): 573=$[M+H]^+$.

$^1$H-NMR (400 MHz, DMSO-$d_6$): 8.04 (d, 1H), 7.27 (s, 1H), 7.15-7.08 (m, 2H), 6.99-6.95 (m, 2H), 6.83 (d, 1H), 6.77 (t, 1H), 6.72-6.69 (m, 1H), 6.51 (s, 1H), 6.32 (s, 1H), 5.81-5.76 (m, 1H), 5.58-5.50 (m, 1H), 4.83 (d, 1H), 4.76-4.62 (m, 2H), 4.01-3.93 (m, 1H), 3.81 (s, 2H), 3.52-3.46 (m, 1H), 3.04-2.99 (m, 1H), 2.62-2.52 (m, 2H), 2.21 (s, 3H), 1.21 (s, 9H), 0.94-0.77 (m, 4H).

Example 40

(E)-(S)-4-{(R)-2-[1-(3-tert-Butyl-phenyl)-cyclopropylamino]-1-hydroxy-ethyl}-9-fluoro-2-oxo-11-oxa-3,16-diaza-tricyclo[15.3.1.1*6,10*]docosa-1(21),6,8,10(22),13,17,19-heptaene-19-carboxylic acid dimethylamide a) (E)-(S)-4-((R)-2-{Benzyloxycarbonyl-[1-(3-tert-butyl-phenyl)-cyclopropyl]-amino}-1-hydroxy-ethyl)-19-dimethylcarbamoyl-9-fluoro-2-oxo-11-oxa-3,16-diaza-tricyclo[15.3.1.1*6,10*]docosa-1(21),6,8,10(22),13,17,19-heptaene-16-carboxylic acid-benzyl ester The title compound is obtained by an analogous reaction sequence (steps a and b) as for example 1, starting from [(2R,3S)-4-(3-allyloxy-4-fluoro-phenyl)-3-tert-butoxycarbonylamino-2-hydroxy-butyl]-[1-(2-tert-butyl-phenyl)-cyclopropyl]-carbamic acid benzyl ester (building block C10) and 5-(allyl-benzyloxycarbonyl-amino).N,N-dimethyl-isophthalmic acid (building block A15).

Rf (EtOAc): 0.51.

MS (ES+): 897=$[M+H]^+$.

$^1$H-NMR (400 MHz, DMSO-$d_6$, 120° C.): 7.82 (d, 1H), 7.46-7.41 (m, 3H), 7.32-7.12 (m, 10H), 7.05 (dd, 1H), 6.95 (dd, 1H), 6.87-6.84 (m, 1H), 6.80-6.76 (m, 1H), 6.01-5.95 (m, 1H), 5.71-5.64 (m, 1H), 5.19-5.02 (m, 4H), 4.80-4.67 (m, 3H), 4.51-4.46 (m, 1H), 4.16-3.94 (m, 3H), 3.76 (dd, 1H), 3.32 (dd, 1H), 3.07 (dd, 1H), 2.87 (s, 6H), 2.74 (dd, 1H), 1.81-1.75 (m, 1H), 1.53-1.47 (m, 1H), 1.32-1.18 (m, 3H), 1.23 (s, 9H), 1.12-1.06 (m, 1H).

b) (E)-(S)-4-{(R)-2-[1-(3-tert-Butyl-phenyl)-cyclopropylamino]-1-hydroxy-ethyl}-9-fluoro-2-oxo-1-oxa-3,16-diaza-tricyclo[15.3.1.1*6,10*]docosa-1 (21),6,8,10(22),13,17,19-heptaene-19-carboxylic acid dimethylamide To a solution of (E)-(S)-4-((R)-2{benzyloxycarbonyl-[1-(3-tert-butyl-phenyl)-cyclopropyl]-amino}-hydroxy-ethyl)-19-dimethylcarbamoyl-9-fluoro-2-oxo-11-oxa-3,16-diaza-tricyclo[15.3.1.1*6,10*]docosa-1(21),6,8,10(22),13,17,19-heptaene-16-carboxylic acid benzyl ester (67 mg, 0.075 mmol) in 4 ml DCM is added iodotrimethylsilane (220 µl, 1.5 mmol) and the mixture is stirred at rt. After 25 min additional iodotrimethylsilane (33 µl, 0.0225 mmol) is added and stirring is continued for 20 min. Excess iodotrimethylsilane is destroyed by addition of 1 ml MeOH, and the solvents are evaporated. The residue is dissolved in 1.8 ml MeOH and purified by preparative HPLC (XTerra RP18, 5 µm, 19×150 mm, 10-100% MeCN (20 min), 20 ml/min) to give the product as off-white resin.

RF (DCM/MeOH/$NH_3$=90/9/1): 0.21.

MS (ES+): 629=$[M+H]^+$.

$^1$H-NMR (400 MHz, DMSO-$d_6$): 7.96 (d, 1H), 7.28 (s, 1H), 7.14-7.08 (m, 2H), 7.00-6.94 (m, 2H), 6.89-6.86 (m, 1H), 6.76-6.67 (m, 4H), 6.34-6.31 (m, 1H), 5.87-5.80 (m, 1H),5.58-5.50 (m, 1H), 4.82-4.63 (m, 3H), 4.02-3.92 (m, 1H), 3.82 (br s, 2H), 3.52-3.46 (m, 1H), 3.04-2.99 (m, 1H), 2.91 (br s, 3H), 2.84 (br s, 3H), 2.66-2.52 (m, 2H), 1.25-1.13 (m, 2H), 1.20 (s, 9H), 0.92-0.76 (m, 4H).

Example 41

(S)-4-{(R)-1-Hydroxy-2-[1-(3-isopropyl-phenyl)-cyclopropylamino]-ethyl}-18-methoxy-3,15,17-triaza-tricyclo[14.3.1.1*6,10*]henicosa-1(19),6,8,10 (21),16(20),17-hexaen-2-one The title compound can be obtained by an analogous reaction sequence as for example 1, starting from ((1S,2R)-1-(3-allyl-benzyl)-3-{benzyloxycarbonyl-[1-(3-isopropyl-phenyl)-cyclopropyl]-amino}-2-hydroxy-propyl)-carbamic acid tert-butyl ester (building block C5) and 2-allylamino-6-methoxy-isonicotinic acid (building block A18).

Rf (DCM/MeOH=95/5): 0.29.

HPLC (Waters SunFire C18, 5 µm, 4.6×150 mm, 30-100% MeCN (3 min), 100% MeCN (2.0 min), 1.5 ml/min) retention time: 2.48 min.

MS (ES+): 543=$[M+H]^+$.

$^1$H-NMR (400 MHz, DMSO-$d_6$): 7.94 (d, 1H), 7.32 (s, 1H), 7.18-7.12 (m, 3H), 7.06-6.97 (m, 4H), 6.57 (t, 1H), 5.83 (s, 1H), 5.59 (s, 1H), 4.73 (d, 1H), 4.06-3.98 (m, 1H), 3.68 (s, 3H), 3.52-3.46 (m, 1H), 3.29-3.19 (m, 1H), 3.09-2.95 (m, 2H), 2.87-2.80 (m, 1H), 2.68-2.61 (m, 2H), 2.58-2.53 (m, 1H), 1.95-1.87 (m, 1H), 1.77-1.69 (m, 1H), 1.45-1.39 (m, 1H), 1.26-1.15 (m, 3H), 1.18 (d, 6H), 1.00-0.89 (m, 3H), 0.86-0.81 (m, 1H).

Example 42

(S)-4-{(R)-2-[1-(3-tert-Butyl-phenyl)-cyclopropylamino]-1-hydroxy-ethyl}-19-methyl-11-oxa-3,16,18-triaza-tricyclo[15.3.1.1*6,10*]docosa-1(21),6,8,10(22),17,19-hexaen-2-one a) (S)-16-Acetyl-4{(R)-2-[1-(3-tert-butyl-phenyl)-cyclopropylamino]-1-hydroxy-ethyl}-19-methyl-11-oxa-3,16,18-triaza-tricyclo[15.3.1.1*6,10*]docosa-1(21),6,8,10(22),17,19-hexaen-2-one The title compound is obtained by an analogous reaction sequence as for example 1, starting from ((1S,2R)-1-(3-allyloxy-benzyl)-3{benzyloxycarbonyl-[1-(3tert-butyl-phenyl)-cyclopropyl]-amino}-2-hydroxy-propyl)carbamic acid tert-butyl ester (building block C6) and 2-(acetyl-allyl-amino)-6-methyl-isonicotinic acid (building block A17).

Rf (DCM/MeOH=95/5):0.25.
MS (LC/MS, ES+): 598.7=[M+H]$^+$.
HPLC (Waters SunFire C 18, 3.5 μm, 4.6×50 mm+precolumn 3.5 μm, 4.6×20 mm, 5-95% MeCN (7.5 min), 100% MeCN (2.5 min), 1.5 ml/min) retention time: 3.61 min.

b) (S)-4{(R)-2-[1-(3-tert-Butyl-phenyl)-cyclopropylamino]-1-hydroxy-ethyl}-19-methyl-11-oxa-3,16,18-triaza-tricyclo[15.3.1.1*6,10*]docosa-1 (21),6,8,10(22),17,19-hexaen-2-one To a solution of (S)-16-acetyl-4-{(R)-2-[1-(3-tert-butyl-phenyl)-cyclopropylamino]-1-hydroxy-ethyl}-19-methyl-11-oxa-3,16,18-triaza-tricyclo[15.3.1.1*6,10*]docosa-1(21),6,8,10(22),17,19-hexaen-2-one (25 mg, 0.042 mmol) in 1.5 ml EtOH at 0° C. is added 2N aq sodium hydroxide (84 μl, 0.17 mmol) and the mixture is stirred for 5 h at 60° C. The reaction mixture is cooled to 0° C. and 340 μl 0.5M aq hydrochloric acid are added. The organic solvent is evaporated, the aqueous solution basified by addition of 1 ml 1M aq potassium hydrogencarbonate and extracted with DCM. The combined organic layers are washed with water, dried over sodium sulfate and evaporated. The residue is purified by preparative thin layer chromatography (DCM/MeOH=95/5) to give the product as colorless solid.

Rf (DCM/MeOH=95/5): 0.24.
MS (ES+): 557=[M+H]$^+$.
$^1$H-NMR (400 MHz, DMSO-d$_6$): 8.03 (d, 1H), 7.31 (s, 1H), 7.16-7.11 (m, 3H), 7.01-6.97 (m, 2H), 6.76-6.70 (m, 2H), 6.52-6.48 (m, 1H), 6.23 (s, 1H), 6.12 (s, 1H), 4.78-4.75 (m, 1H), 4.24-4.19 (m, 1H), 3.93-3.87 (m, 1H), 3.86-3.77 (m, 1H), 3.47-3.40 (m, 1H), 3.38-3.32 (m, 2H), 3.03-2.93 (m, 2H), 2.63-2.54 (m, 2H), 2.48-2.42 (m, 2H), 2.20 (s, 3H), 1.76-1.59 (m, 2H), 1.52-1.42 (m, 1H), 1.24 (s, 9H), 0.94-0.79 (m, 4H).

Example 43

13,14-Benzo-(S)-4{(R)-1-Hydroxy-2-[1-(3-isopropyl-phenyl)-cyclo-propylamino]-ethyl}-19-methyl-1,16-dioxa-3,18-diaza-tricyclo[15.3.1.1*6,10*]docosa-1(21),6,8,10(22),17,19-hexaen-2-one a) 2-{2-[3-((2S,3R)-4-{Benzyloxycarbonyl-[1-(3-isopropyl-phenyl)-cyclopropyl]-amino}-2-tert-butoxycarbonylamino-3-hydroxy-butyl)-phenoxymethyl]-benzyloxy}-6-methyl-isonicotinic acid methyl ester A suspension of 1 g (2.72 mmol) 2-(2-methanesulfonyloxymethyl-benzyloxy)-6-methyl-isonicotinic acid methyl ester (building block E2), 1.62 g (2.72 mmol), [(2R,3S)-3-tert-butoxycarbonylamino-2-hydroxy-4-(3-hydroxy-phenyl)-butyl]-[1-(3-isopropyl-phenyl)-cyclopropyl]-carbamic acid benzyl ester (building block C17), 0.5 g (1.368 mmol) tetrabutylammonium iodide, 0.44 g (1.368 mmol) caesium carbonate, and 0.56 g (4.10 mmol) potassium carbonate in DMF (10 ml) is stirred for 6 h. The mixture is diluted with EtOAc and water. The organic layer is washed with water and brine, dried over sodium sulfate and chromatographed on silica gel (hexane/EtOAc 6:1, 4:1, 2:1) to yield a yellow resin.

Rf: (EtOAc/hexane 1:2): 0.3
HPLC (Zorbax SB-C18, 3×30 mm, 1.8 μm, 70-100% MeCN (3.25 min), 100% MeCN (0.75 min)): 3.862 min
MS (ES+): 858=[M+H]$^+$ b) 13,14-Benzo-[(R)-2-hydroxy-2-((S)-19-methyl-2-oxo-11,16-dioxa-3,18-diaza-tricyclo[15.3.1.1*6,10*]docosa-1 (21),6,8,10(22),17,19-hexaen-4-yl)-ethyl]-[1-(3-isopropyl-phenyl)-cyclopropyl]-carbamic acid benzyl ester 1.35 g (1.57 mmol) 2-{2-[3-((2S,3R)-4-{benzyloxycarbonyl-[1-(3-isopropyl-phenyl)-cyclopropyl]-amino}-2-tert-butoxycarbonylamino-3-hydroxy-butyl)-phenoxymethyl]-benzyloxy}6-methyl-isonicotinic acid methyl ester are dissolved in 10 ml MeOH and 4 ml 1N aq sodium hydroxide, and stirred 18 h. The mixture is acidified with 5 ml 1N aq hydrochloric acid and extracted with EtOAc. The organic phase is washed with brine, dried over sodium sulfate, and concentrated. The residue is taken up in 10 ml 4N hydrochloric acid in dioxan, stirred for 2 h and the solvent is evaporated at 25° C. under reduced pressure. The residual product is dissolved in 100 ml DCM containing 1.05 ml N-methyl morpholin and added with use of a syringe pump to a stirred solution of 1.2 g (3.15 mmol) HATU in 10 ml DCM over a period of 3 h. Stirring is continued for 1 h. The mixture is washed with 5% aq citric acid, water, 5% aq sodium bicarbonate and water, dried over sodium sulfate, and chromatographed on silica gel (hexane/EtOAc 5:1, 3:1, 2:1, 1:1, 1:2) to obtain a colorless resin.

Rf: (EtOAc/hexane 1:1): 0.38
HPLC (Zorbax SB-C18, 3×30 mm, 1.8 μm, 50-100% MeCN (3.25 min), 100% MeCN (0.75 min)): 3.369 min
MS (ES+): 726=[M+H]$^+$ c) 13,14-Benzo-(S)-4-{(R)-1-Hydroxy-2-[1-(3-isopropyl-phenyl)-cyclo-propylamino]-ethyl}-19-methyl-11,16-dioxa-3,18-diaza-tricyclo[15.3.1.1*6,10*]docosa-1(21),6,8,10(22),17,19-hexaen-2-one 13,14-Benzo-[(R)-2-hydroxy-2-((S)-19-methyl-2-oxo-1,16-dioxa-3,18-diaza-tricyclo[15.3.1.1*6,10*]docosa-1(21),6,8,10(22),17,19-hexaen-4-yl)-ethyl]-[1-(3-isopropyl-phenyl)-cyclopropyl]-carbamic acid benzyl ester (279 mg, 0.384 mmol) is hydrogenated in THF in the presence of 40 mg Pt/C (Engelhard 4709) and 40 mg Pd/C (Engelhard 4505) for 8 h. The mixture is filtered and chromatographed on silica gel (EtOAc/hexanes 3:1, 1:1 and 2:1) to give a resin.

Rf: (EtOAc/hexane 2:1): 0.28
HPLC (Zorbax SB-C18, 3×30 mm, 1.8 μm, 30-100% MeCN (3.25 min), 100% MeCN (0.75 min)): 2.809 min
MS (ES+): 592=[M+H]$^+$

Example 44

(S)-19-[1,3]Dioxolan-2-yl-4-{(R)-1-hydroxy-2-[1-(3-isopropyl-phenyl)-cyclopropylamino]-ethyl}-11-oxa-3,16-diaza-tricyclo[15.3.1.1*6,10*]docosa-1(21),6,8,10(22),17,19-hexaen-2-one The title compound is obtained by an analogous reaction as for example 1, starting from (1S,2R)-1-(3-allyloxy-benzyl)-

3-{benzyloxycarbonyl-[1-(3-isopropyl-phenyl)-cyclopropyl]-amino}-2-hydroxy-propyl)-carbamic acid tert-butyl ester (building block C7) and 3-(allyl-benzyloxycarbonyl-amino)-5-[1,3]dioxolan-2-yl-benzoic acid (building block A21).

Rf: (DCM/MeOH/25% aq NH$_3$, 90/9/1): 0.43
HPLC (Zorbax SB-C18, 3×30 mm, 1.8 μm, 30-100% MeCN (3.25 min), 100% MeCN (0.75 min)): 2.509 min
MS (ES+): 600=[M+H]$^+$

Example 45

(S)-4-{(R)-1-Hydroxy-2-[1-(3-isopropyl-phenyl)-cyclopropylamino]-ethyl}-19-thiazol-2-yl-11-oxa-3,16-diaza-tricyclo[15.3.1.1*6,10*]docosa-1(20),6,8,10(22),17(21),18-hexaen-2-one a) (Z)—(S)-4-((R)-2-{Benzyloxycarbonyl-[1-(3-isopropyl-phenyl)-cyclopropyl]-amino}-1-hydroxy-ethyl)-2-oxo-19-thiazol-2-yl-11-oxa-3,16-diaza-tricyclo[15.3.1.1*6,10*]docosa-1(20),6,8,10(22),13,17(21),18-heptaene-16-carboxylic acid benzyl ester The title compound is obtained by an analogous reaction sequence as for example 1 (steps a-b), starting ((1S,2R)-1-(3-allyloxy-benzyl)-3-{benzyloxycarbonyl-[1-(3-isopropyl-phenyl)-cyclopropyl]-amino}-2-hydroxy-propyl)-carbamic acid tert-butyl ester (building block C7) and 3-(allyl-benzyloxycarbonyl-amino)-5-thiazol-2-yl-benzoic acid (building block A20).

Rf: (hexane/EtOAc 1:1): 0.37
HPLC (Zorbax SB-C18, 3×30 mm, 1.8 μm, 70-100% MeCN (3.25 min), 100% MeCN (0.75 min)): 2.454 min
MS (ES+): 877=[M+H]$^+$ b) (S)-4{(R)-1-Hydroxy-2-[1-(3-isopropyl-phenyl)-cyclopropylamino]-ethyl}-19-thiazol-2-yl-11-oxa-3,16-diaza-tricyclo[15.3.1.1*6,10*]docosa-1(20),6,8,10(22),17(21),18-hexaen-2-one (Z)—(S)-4-((R)-2-{Benzyloxycarbonyl-[1-(3-isopropyl-phenyl)-cyclopropyl]-amino}-1-hydroxy-ethyl)-2-oxo-19-thiazol-2-yl-18-oxa-3,16-diaza-tricyclo[15.3.1.1*6,10*]docosa-1(20),6,8,10(22),13,17(21),18-heptaene-16-carboxylic acid benzyl ester (163 mg, 0.187 mmol) is hydrogenated in THF in the presence of 56 mg Pd/C (Engelhard 4505) for 5 h. The mixture is filtered over high-flow and concentrated. The residue is taken up in 6N aq hydrochloric acid and heated at 60° C. for 3 h. The mixture is diluted with water and washed with hexane, basified with solid sodium carbonate and extracted with THF. The organic phase is dried over sodium sulfate and evaporated. The product is obtained as a colorless resin after chromatography on silica gel (DCM/MeOH/25% aq NH$_3$ 9/2/0.2).

Rf: (DCM/MeOH/25% aq NH$_3$, 90/9/1): 0.23
HPLC (Zorbax SB-C18, 3×30 mm, 1.8 μm, 40-100% MeCN (3.25 min), 100% MeCN (0.75 min)): 1.893 min
MS (ES+): 611=[M+H]$^+$

Example 46

(S)-4-{(R)-1-Hydroxy-2-[1-(3-isopropyl-phenyl)-cyclopropylamino]-ethyl}-19-(2-oxo-pyrrolidin-1-yl)-18-oxa-3,16-diaza-tricyclo[15.3.1.1*6,10*]docosa-1(21),6,8,10(22),17,19-hexaen-2-one The title compound is obtained by an analogous reaction sequence as for example 1, starting from ((1S,2R)-1-(3-allyloxy-benzyl)-3-{benzyloxycarbonyl-[1-(3-isopropyl-phenyl)-cyclopropyl]-amino}-2-hydroxy-propyl)-carbamic acid tert-butyl ester (building block C7) and 3-(allyl-benzyloxycarbonyl-amino)-5-(2-oxo-pyrrolidin-1-yl)-benzoic acid (building block A19).

Rf: (DCM/MeOH/25% aq NH$_3$, 90/9/1): 0.20
HPLC (Zorbax SB-C18, 3×30 mm, 1.8 μm, 40-100% MeCN (3.25 min), 100% MeCN (0.75 min)): 0.914 min
MS (ES+): 611=[M+H]$^+$

Example 47

(S)-8-Fluoro-4-{(R)-1-hydroxy-2-[1-(3-isopropyl-phenyl)-cyclopropylamino]-ethyl}-19-methoxymethyl-11-oxa-3,16diaza-tricyclo[15.3.1.1*6,10*]docosa-1(21),6,8,10(22),17,19-hexaen-2-one The title compound is obtained by an analogous reaction sequence as for example 1, starting from {(1S,2R)-1-(3-allyloxy-5-fluoro-benzyl)-2-hydroxy-3-[1-(3-isopropyl-phenyl)-cyclopropylamino]-propyl}-carbamic acid tert-butyl ester (building block C14) and 3-(allyl-benzyloxycarbonyl-amino)-5-methoxymethyl-benzoic acid (building block A7).

HPLC (Zorbax SB-C18, 3×30 mm, 1.8 μm, 30-100% MeCN (3.25 min), 100% MeCN (0.75 min)): 2.579 min
MS (ES+): 590=[M+H]$^+$
$^1$H-NMR (400 MHz, DMSO-d$_6$): 7.87 (d, 1H), 7.16 (t, 1H), 7.13 (s, 1H), 7.05 (d, 1H), 6.99 (d, 1H), 6.90 (s, 1H), 6.64-6.52 (m, 4H), 6.44 (s, 1H), 5.85 (t, 1H), 4.79 (d, 1H,), 4.25-4.19 (m, 1H), 4.21 (s, 2H), 3.96-3.84 (m, 2H), 3.48-3.40 (m, 1H), 3.22 (s, 3H), 3.01-2.89 (m, 2H), 2.85-2.75 (m, 1H), 2.68-2.59 (m, 1H), 2.57-2.40 (m, 2H), 1.74-1.45 (m, 4H), 1.14 (d, 6H), 0.95-0.75 (m, 4H).

Example 48

(S)-18-Chloro-4-{(R)-1-hydroxy-2-[1-(4-isopropyl-pyridin-2-yl)-cyclopropyl-amino]-ethyl}-3,15,17-triaza-tricyclo[14.3.1.1*6,10*]henicosa-1(20),6,8,10(21),16,18-hexaen-2-one a) [(R)-2-((E)-(S)-15-Acetyl-18-chloro-2-oxo-3,15,17-triaza-tricyclo[14.3.1.1*6,10*]-henicosa-1(20),6,8,10(21),12,16,18-heptaen-4-yl)-2-hydroxy-ethyl]-[1-(4-isopropyl-pyridin-2-yl)-cyclopropyl]-carbamic acid benzyl ester The title compound is obtained by an analogous reaction sequence as for example 1 (steps a-b), starting from [(2R,3S)-4-(3-allyl-phenyl)-3-tert-butoxycarbonylamino-2-hydroxy-butyl]-[1-(4-isopropyl-pyridin-2-yl)-cyclopropyl]-carbamic acid benzyl ester (building block C12) and 2-(acetyl-allyl-amino)-6-chloro-isonicotinic acid (building block A16).

Rf: (hexane/EtOAc 1:2): 0.55
HPLC (Zorbax SB-C18, 3×30 mm, 1.8 μm, 40-100% MeCN (3.25 min), 100% MeCN (0.75 min)): 2.383 min
MS (ES+): 722, 724=[M+H]$^+$ b) (S)-18-Chloro-4-{(R)-1-hydroxy-2-[1-(4-isopropyl-pyridin-2-yl)-cyclopropylamino]-ethyl}-3,15,17-triaza-tricyclo[14.3.1.1*6,10*]henicosa-1(20),6,8,10(21),16,18-hexaen-2-one A solution of 413 mg (0.572 mmol) [(R)-2-((E)-(S)-15-acetyl-18-chloro-2-oxo-3,15,17-triaza-tricyclo[14.3.1.1*6,10*]henicosa-1(20),6,8,10(21),12,16,18-heptaen-4-yl)-2-hydroxy-ethyl]-[1-(4-isopropyl-pyridin-2-yl)-cyclopropyl]- carbamic acid benzyl ester in 5 ml EtOH is hydrogenated in the presence of 80 mg 5% Pt/C (Engelhard 4709) for 5 h. The mixture is filtered over high-flow and evaporated. For complete deprotection of the protective group the residue is taken up in 6N aq hydrochloric acid and stirred at 60° C. for 2 h. The mixture is diluted with water and washed twice with hexan. The aqueous layer is basified with solid sodium carbonate and extracted with THF. The combined organic layers are dried over sodium sulfate and evaporated. Purification by chromatography on silica gel (gradient of DCM and MeOH/25% aq NH3 9:1, 2-10%) gives the product.

Rf: (DCM/MeOH/25% aq $NH_3$ 90/9/1): 0.29
HPLC (Zorbax SB-C18, 3×30 mm, 1.8 μm, 40-100% MeCN (3.25 min), 100% MeCN (0.75 min)): 1.966 min
MS (ES+): 548, 550=$[M+H]^+$ Example 49

(S)-19-Chloro-4-{(R)-1-hydroxy-2-[1-(4-isopropyl-pyridin-2-yl)-cyclo-propylamino]-ethyl}-11-oxa-3,16,18-triaza-tricyclo[15.3.1.1*6,10*]docosa-1(21),6,8,10(22),17,19-hexaen-2-one The title compound is obtained by an analogous reaction sequence as for example 48, starting from [(2R,3S)-4-(3-allyloxy-phenyl)-3-tert-butoxycarbonylamino-2-hydroxy-butyl]-[1-(4-isopropyl-pyridin-2-yl)-cyclopropyl]-carbamic acid benzyl ester (building block C11) and 2-(acetyl-allyl-amino)-6-chloro-isonicotinic acid (building block A16)

Rf: (DCM/MeOH/25% aq $NH_3$ 90/9/1): 0.36
HPLC (Zorbax SB-C18, 3×30 mm, 1.8 μm, 40-100% MeCN (3.25 min), 100% MeCN (0.75 min)): 1.273 min
MS (ES+): 564, 566=$[M+H]^+$ Example 50

(S)-4-{(R)-1-Hydroxy-2-[1-(3-isopropyl-phenyl)-cyclopropylamino]-ethyl}-19-methyl-11,16-dioxa-3,18-diaza-tricyclo[15.3.1.1*6,10*]docosa-1 (21),6,8,10(22),17,19-hexaen-2-one a) {(1S,2R)-1-(3-Benzyloxy-benzyl)-2-hydroxy-3-[1-(3-isopropyl-phenyl)-cyclopropylamino]-propyl}-carbamic acid tert-butyl ester The product is obtained by an analogous reaction sequence as for building block C5 (steps a-d), starting from (S)-3-(3-benzyloxy-phenyl)-2-tert-butoxycarbonylamino-propionic acid methyl ester (building block C1) and 1-(3-isopropyl-phenyl)-cyclopropylamine (building block D1).

MS (ES+): 545=$[M+H]^+$
HPLC (Nucleosil C18HD, 4×70 mm, 3 μm, 20-100% MeCN (6 min), 100% MeCN (1.5 min)) retention time=5.35 min b) [(2R,3S)-4-(3-Benzyloxy-phenyl)-3-tert-butoxy-carbonylamino-2-hydroxy-butyl]-[1-(3-isopropyl-phenyl)-cyclopropyl]-carbamic acid tert-butyl ester {(1S,2R)-1-(3-Benzyloxy-benzyl)-2-hydroxy-3-[1-(3-isopropyl-phenyl)-cyclopropylamino]-propyl}-carbamic acid tert-butyl ester (1.60 g, 2.94 mmol, 1 eq) is dissolved in 20 ml THF. N,N-Diisopropylethylamine (1.06 ml, 5.87 mmol, 2 eq) and di-tert-butyl dicarbonate (838 mg, 3.82 mmol, 1.3 eq) are added. The reaction is stirred for 65 h at 60*C. The mixture is diluted with 10 ml citric acid (10% in water) and EtOAc. The organic layer is dried over magnesium sulfate and concentrated. The residue is purified by chromatography on silica (EtOAc/hexane 3/7) to give the product.

MS (ES+): 645=$[M+H]^+$
HPLC (Nucleosil C18HD, 4×70 mm, 3 μm, 20-100% MeCN (6 min), 100% MeCN (1.5 min)) retention time=7.60 min c) [(2R,3S)-4-(3-Hydroxy-phenyl)-3-tert-butoxycarbonylamino-2-hydroxy-butyl]-[1-(3-isopropyl-phenyl)-cyclopropyl]-carbamic acid tert-butyl ester

[(2R,3S)-4-(3-Benzyloxy-phenyl)-3-tert-butoxycarbonylamino-2-hydroxy-butyl]-[1-(3-isopropyl-phenyl)-cyclopropyl]-carbamic acid tert-butyl ester (925 mg, 1.49 mmol, 1 eq) is dissolved in 60 ml EtOH and added to Pd/C (181 mg) in 5 ml of EtOH under argon. The atmosphere is exchanged against hydrogen, and the reaction is stirred for 2 h. The mixture is filtered through Hyflo and concentrated. The residue is purified by chromatography on silica (hexane/EtOAc 7/3) to give the product.

MS (ES+): 529=$[M+H]^+$
HPLC (Nucleosil C18HD, 4×70 mm, 3 μm, 20-100% MeCN (6 min), 100% MeCN (1.5 min)) retention time=6.21 min d) 2-{4-[3((2S,3R)-2-tert-Butoxycarbonylamino-4{tert-butoxycarbonyl-[1-(3-isopropyl-phenyl)-cyclopropyl]-amino}-3-hydroxy-butyl)-phenoxy]-butoxy}-6-methyl-isonicotinic acid methyl ester

[(2R,3S)-4-(3-Hydroxy-phenyl)-3-tert-butoxycarbonylamino-2-hydroxy-butyl]-[1-(3-isopropyl-phenyl)-cyclopropyl]-carbamic acid tert-butyl ester (400 mg, 721 μmol, 1 eq) and 2-(4-methanesulfonyloxy-butoxy)-6-methyl-isonicotinic acid methyl ester (229 mg, 721 μmol, 1 eq) (building block E1) are dissolved in 4 ml DMF. Caesium carbonate (470 mg, 1.44 mmol, 2 eq) and TBAI (53 mg, 144 μmol, 0.2 eq) are added. The reaction mixture is stirred for 16 h at rt. The mixture is diluted with water and EtOAc. The organic layer is washed with water, dried over magnesium sulfate and concentrated. The residue is purified by chromatography on silica (EtOAc/hexane 3/7) to give the product.

MS (ES+): 776=$[M+H]^+$
HPLC (Nucleosil C18HD, 4×70 mm, 3 μm, 65-100% MeCN (6 min), 100% MeCN (1.5 min)) retention time=6.61 min e) (S)-4-{(R)-1-Hydroxy-2-[1-(3-isopropyl-phenyl)-cyclopropylamino]-ethyl}-19-methyl-11,16-dioxa-3,18-diaza-tricyclo[15.3.1.1*6,10*]docosa-1(21),6,8,10(22),17,19-hexaen-2-one 2-{4-[3((2S,3R)-2-tert-Butoxycarbonylamino-4-{tert-butoxycarbonyl-[1-(3-isopropyl-phenyl)-cyclopropyl]-amino}-3-hydroxy-butyl)-phenoxy]-butoxy}-6-methyl-isonicotinic acid methyl ester (260 mg, 335 μmol, 1 eq) is dissolved in 0.67 ml 1N aq sodium hydroxide and 3 ml MeOH and stirred at rt for 150 min. The mixture is concentrated and diluted with 8 ml of 4N hydrochloric acid in dioxane. The mixture is stirred at rt for 1 h and then concentrated. The obtained white solid is dissolved in DCM (50 ml), N-methylmorpholine (209 μl, 1.90 mmol, 5.67 eq) and $Et_3N$ (210 □, 1.50 mmol, 4.47 eq). This solution is slowly added to HOBt (206 mg, 1.51 mmol, 4.5 eq) and EDC*HCl (295 mg, 1.51 mmol, 4.5 eq) in 150 ml DCM within 6 h. The reaction mixture is stirred for another 12 h and then diluted with citric acid (10% in water), followed by aq sodium bicarbonate and EtOAc. The organic layer is washed with water, dried over sodium sulfate and concentrated. The residue is purified by chromatography on silica (DCM/MeOH/NH$_3$ 480/20/1) to give the product.

MS (ES+): 544=[M+H]$^+$

HPLC (Nucleosil C18HD, 4×70 mm, 3 μm, 20-100% MeCN (6 min), 100% MeCN (1.5 min)) retention time=3.68 min $^1$H-NMR (400 MHz, DMSO-d$_6$): 8.11 (d, 1H), 7.32-6.98 (m, 5H), 6.83 (s, 1H), 6.78-6.60 (m, 3H), 6.53 (s, 1H), 4.88 (d, 1H), 4.45-4.39 (m, 1H), 4.27-4.20 (m, 1H), 4.18-4.12 (m, 1H), 4.00-3.92 (m, 1H), 3.92-3.83 (m, 1H), 3.53-3.46 (m, 1H), 2.99 (d, 1H), 2.87-2.78 (m, 1H), 2.63-2.45 (m, 3H), 2.37 (s, 3H), 1.82-1.50 (m, 4H), 1.18 (d, 6H), 0.95-0.79 (m, 4H).

Example 51

(S)-4-{(R)-1-Hydroxy-2-[1-(3-isopropyl-phenyl)-cyclopropylamino]-ethyl}-19-(2-oxo-pyrrolidin-1-yl)-11,16-dioxa-3-aza-tricyclo[15.3.1.1*6,10*]docosa-1(21),6,8,10(22),17,19-hexaen-2-one The title compound is obtained by an analogous reaction sequence as for example 1, starting ((1S,2R)-1-(3-allyloxy-benzyl)-3-{benzyloxycarbonyl-[1-(3-isopropyl-phenyl)-cyclopropyl]-amino}-2-hydroxy-propyl)-carbamic acid tert-butyl ester (building block C7) and 3-allyloxy-5-(2-oxo-pyrrolidin-1-yl)-benzoic acid (building block A22).

HPLC (Zorbax SB-C18, 3×30 mm, 1.8 μm, 30-100% MeCN (3.25 min), 100% MeCN (0.75 min)) retention time: 2.68 min

MS (LC/MS, ES+): 612=[M+H]$^+$.

$^1$H-NMR (400 MHz, DMSO-d$_6$): 8.01 (d, 1H), 7.31 (s, 1H), 7.18-7.13 (m, 3H), 7.05 (d, 1H), 7.0-6.98 (m, 2H), 6.83 (s, 1H), 6.79 (d, 1H), 6.72 (d, 1H), 4.82 (d, 1H), 4.44-4.33 (m, 1H), 4.24-4.19 (m, 1H), 4.10-4.04 (m, 1H), 3.98-3.86 (m, 2H), 3.75 (t, 2H), 3.54-3.47 (m, 1H), 2.93 (dd, 1H), 2.83-2.76 (m, 1H), 2.67 (dd, 1H), 2.57 (dd, 1H), 2.51-2.45 (m, 4H), 2.06-1.98 (m, 2H), 1.82-1.62 (m, 4H), 1.13 (d, 6H), 0.93-0.87 (m, 3H), 0.81-0.78 (m, 1H).

Example 52

(S)-4-{(R)-2-[1-(4-tert-Butyl-pyridin-2-yl)cyclopropylamino]-1-hydroxy-ethyl}-18-methyl-3,15,17-triaza-tricyclo[14.3.1.1*6,10*]henicosa-1(19),6,8,10(21),16(20),17-hexaen-2-one The title compound is obtained by an analogous reaction sequence as for example 1, starting from [(2R,3S)-4-(3-allyl-phenyl)-3-tert-butoxycarbonylamino-2-hydroxy-butyl]-[1-(4-tert-butyl-pyrid-2-yl)-cyclopropyl]-carbamic acid benzyl ester (building block C8) and 2-(allyl-benzyloxycarbonyl-amino)-6-methyl-isonicotinic acid (building block A23).

HPLC (Zorbax SB-C18, 3×30 mm, 1.8 μm, 10-100% MeCN (3.25 min), 100% MeCN (0.75 min)) retention time: 2.90 min

MS (LC/MS, ES+): 542=[M+H]$^+$.

$^1$H-NMR (400 MHz, DMSO-d$_6$): 8.33 (d, 1H), 8.08 (d, 1H), 7.75 (s, 1H), 7.38 (s, 1H), 7.18 (t, 1H), 7.13 (dd, 1H), 7.07 (d, 1H), 7.02 (d, 1H), 6.59 (t, 1H), 6.34 (s, 1H), 5.89 (s, 1H), 4.99 (d, 1H), 4.11-4.03 (m, 1H), 3.60-3.59 (m, 1H), 3.43-3.38 (m, 1H), 3.37-3.24 (m, 1H), 3.16 (d, 1H), 3.05-2.95 (m, 1H), 2.75-2.62 (m, 6H), 2.18 (s, 3H), 1.98-1.88 (m, 1H), 1.80-1.70 (m, 1H), 1.40-1.30 (m, 1H), 1.27 (s, 9H), 1.21-1.16 (m, 2H), 1.06-0.98 (m, 2H).

Example 53

(S)-4-{(R)-2-[1-(4-tert-Butyl-pyridin-2-yl)-cyclopropylamino]-1-hydroxy-ethyl}-19-methyl-11-oxa-3,16,18-triaza-tricyclo[15.3.1.1*6,10*]docosa-1(21),6,8,10(22),17,19-hexaen-2-one The title compound is obtained by an analogous reaction sequence as for example 1, starting from [(2R,3S)-4-(3-allyloxy-phenyl)-3-tert-butoxycarbonylamino-2-hydroxy-butyl]-[1-(4-tert-butyl-pyridin-2-yl)-cyclopropyl]-carbamic acid benzyl ester (building block C18) and 2-(allyl-benzyloxycarbonyl-amino)-6-methyl-isonicotinic acid (building block A23).

HPLC (Zorbax SB-C18, 3×30 mm, 1.8 μm, 0-100% MeCN (3.25 min), 100% MeCN (0.75 min)) retention time: 3.09 min

MS (LC/MS, ES+): 558=[M+H]$^+$.

$^1$H-NMR (400 MHz, DMSO-d$_6$): 8.33 (d, 1H), 8.15 (d, 1H), 7.72 (s, 1H), 7.18 (t, 1H), 7.13 (dd, 1H), 7.08 (s, 1H), 6.82 (d, 1H), 6.75 (dd, 1H), 6.56 (dd, 1H), 6.30 (s, 1H), 6.19 (s, 1H), 5.03 (d, 1H), 4.30-4.23 (m, 1H), 3.96-3.83 (m, 2H), 3.59-3.51 (m, 1H), 3.05 (d, 2H), 2.72-2.52 (m, 3H), 2.21 (s, 3H), 1.8-1.6 (m, 3H), 1.52-1.42 (m, 1H), 1.27 (s, 9H), 1.28-1.16 (m, 2H), 1.03-0.93 (m, 2H).

Example 54

(S)-4-{(R)-1-Hydroxy-2-[1-(4-isopropyl-pyridin-2-yl)-cyclopropylamino]-ethyl}-18-methoxymethyl-3,15-diaza-tricyclo[14.3.1.1*6,10*]henicosa-1(19),6,8,10(21),16(20),17-hexaen-2-one The title compound is obtained by an analogous reaction sequence as for example 1, starting from [(2R,3S)-4-(3-allyl-phenyl)-3-tert-butoxycarbonylamino-2-hydroxy-butyl]-[1-(4-isopropyl-pyridin-2-yl)-cyclopropyl]-carbamic acid benzyl ester (building block C12) and 3-(allyl-benzyloxycarbonyl-amino)-5-methoxymethyl-benzoic acid (building block A7).

HPLC (Zorbax SB-C18, 3×30 mm, 1.8 μm, 0-100% MeCN (3.25 min), 100% MeCN (0.75 min)) retention time: 3.45 min

MS (LC/MS, ES+): 557=[M+H]$^+$.

$^1$H-NMR (400 MHz, DMSO-d$_6$): 8.32 (d, 1H), 7.93 (d, 1H), 7.61 (s, 1H), 7.40 (s, 1H), 7.18 (t, 1H), 7.06 (d, 1H), 7.08 (d, 1H), 7.02-7.00 (m, 2H), 6.60 (s, 1H), 6.54 (s, 1H), 6.25 (s, 1H), 5.96 (t, 1H), 4.92 (d, 1H), 4.22 (s, 2H), 4.13-4.05 (m, 1H), 3.6-3.5 (m, 1H), 3.22 (s, 3H), 3.20-3.16 (m, 1H), 3.03-2.63 (m, 8H), 1.97-1.87 (m, 1H), 1.82-1.72 (m, 1H), 1.52-1.42 (m, 1H), 1.30-1.27 (m, 1H), 1.20 (d, 6H), 1.21-0.99 (m, 4H).

Example 55

(S)-4-{(R)-2-[1-(4-tert-Butyl-pyridin-2-yl)-cyclopropylamino]-1-hydroxy-ethyl}-18-methoxymethyl-3,15-diaza-tricyclo[14.3.1.1*6,10*]henicosa-1(19),6,8,10(21),16(20),17-hexaen-2-one The title compound is obtained by an analogous reaction sequence as for example 1, starting from [(2R,3S)-4-(3-allyl-phenyl)-3-tert-butoxycarbonylamino-2-hydroxy-butyl]-[1-(4-tert-butyl-pyrid-2-yl)-cyclopropyl]-carbamic acid benzyl ester (building block C8) and 3-(allyl-benzyloxycarbonyl-amino)-5-methoxymethyl-benzoic acid (building block A7).

HPLC (Zorbax SB-C18, 3×30 mm, 1.8 μm, 30-100% MeCN (3.25 min), 100% MeCN (0.75 min)) retention time: 2.69 min

MS (LC/MS, ES+): 571=[M+H]$^+$.

$^1$H-NMR (400 MHz, DMSO-d$_6$): 8.33 (d, 1H), 7.92 (d, 1H), 7.77 (s, 1H), 7.41 (s, 1H), 7.17 (t, 1H), 7.11 (d, 1H), 7.08 (d, 1H), 7.01 (d, 1H), 8.58 (s, 1H), 6.53 9s, 1H), 6.24 (s, 1H), 5.95 (t, 1H), 4.97 (d, 1H), 4.21 (s, 2H), 4.12-4.02 (m, 1H), 3.61-3.5 (m, 1H), 3.43-3.47 (m, 1H), 3.21 (s, 3H), 3.16 (d, 1H), 3.03-2.90 (m, 1H), 2.74-2.65 (m, 5H), 1.97-1.87 (m, 1H), 1.81-1.71 (m, 1H), 1.52-1.41 (m, 1H), 1.29-1.15 (m, 3H), 1.27 (s, 9H), 1.13-0.99 (m, 2H).

Example 56

(S)-4-{(R)-1-Hydroxy-2-[1-(4-isopropyl-pyridin-2-yl)-cyclopropylamino]-ethyl}-19-methoxymethyl-11-oxa-3,16-diaza-tricyclo[15.3.1.1*6,10*]docosa-1(21),6,8,10(22),17,19-hexaen-2-one The title compound is obtained by an analogous reaction sequence as for example 1, starting from [(2R,3S)-4-(3-allyloxy-phenyl)-3-tert-butoxycarbonylamino-2-hydroxy-butyl]-[1-(4-isopropyl-pyridin-2-yl)-cyclopropyl]-carbamic acid benzyl ester (building block C11) and 3-(allyl-benzyloxycarbonyl-amino)-5-methoxymethyl-benzoic acid (building block A7).

HPLC (Zorbax SB-C18, 3×30 mm, 1.8 μm, 30-100% MeCN (3.25 min), 100% MeCN (0.75 min)) retention time: 2.04 min

MS (LC/MS, ES+): 573=[M+H]$^+$.

$^1$H-NMR (400 MHz, DMSO-d$_6$): 8.31 (d, 1H), 7.99 (d, 1H), 7.56 (s; 1H), 7.18 (t, 1H), 7.08 (s, 1H), 7.00 (d, 1H), 6.83 (d, 1H), 6.76 (dd, 1H), 6.61 (s, 1H), 6.59 (s, 1H), 6.56 (s, 1H), 5.89 (dd, 1H), 4.96 (d, 1H), 4.30-4.24 (m, 1H), 4.25 (s, 2H), 3.96-3.88 (m, 2H), 3.57-3.41 (m, 2H), 3.25 (s, 3H), 3.07-2.96 (m, 2H), 2.87-2.81 (m, 1H), 2.74-2.60 (m, 4H), 1.8-1.5 (m, 4H), 1.25 (dd, 1H), 1.21-1.10 (m, 1H), 1.20 (d, 3H), 1.18 (d, 3H), 1.01-0.95 (m, 2H).

Example 57

(S)-4-{(R)-2-[1-(4-tert-Butyl-pyridin-2-yl)-cyclopropylamino]-1-hydroxy-ethyl}-19-methoxymethyl-11-oxa-3,16-diaza-tricyclo[15.3.1.1*6,10*]docosa-1(21),6,8,10(22),17,19-hexaen-2-one The title compound is obtained by an analogous reaction sequence as for example 1, starting from [(2R,3S)-4-(3-allyloxy-phenyl)-3-tert-butoxycarbonylamino-2-hydroxy-butyl]-[1-(4-tert-butyl-pyridin-2-yl)-cyclopropyl]-carbamic acid benzyl ester (building block C18) and 3-(allyl-benzyloxycarbonyl-amino)-5-methoxymethyl-benzoic acid (building block A7).

HPLC (Zorbax SB-C18, 3×30 mm, 1.8 μm, 30-100% MeCN (3.25 min), 100% MeCN (0.75 min)) retention time: 2.38 min

MS (LC/MS, ES+): 587=[M+H]$^+$.

$^1$H-NMR (400 MHz, DMSO-d$_6$): 8.32 (d, 1H), 7.98 (d, 1H), 7.73 (s, 1H), 7.18 (t, 1H), 7.12-7.10 (m, 2H), 6.83 (d, 1H), 6.74 (dd, 1H), 6.60 (s, 1H), 6.57 (s, 1H), 6.54 (s, 1H), 5.88 (dd, 1H), 5.00 (d, 1H), 4.32-4.22 (m, 1H), 4.24 (s, 2H), 3.96-3.85 (m, 2H), 3.6-3.4 (m, 2H), 3.25 (s, 3H), 3.07-2.95 (m, 2H), 2.73-2.56 (m, 3H), 1.8-1.4 (m, 4H), 1.26 (s, 9H), 1.28-1.17 (m, 2H), 1.03-0.93 (m, 2H).

Example 58

(S)-4-{(R)-2-[1-(4-tert-Butyl-pyridin-2-yl)-cyclopropylamino]-1-hydroxy-ethyl}-19-oxazol-2-yl-11-oxa-3,16-diaza-tricyclo[15.3.1.1*6,10*]docosa-1(20),6,8,10(22),17(21),18-hexaen-2-one The title compound is obtained by an analogous reaction sequence as for example 1, starting from [(2R,3S)-4-(3-allyloxy-phenyl)-3-tert-butoxycarbonylamino-2-hydroxy-butyl]-[1-(4-tert-butyl-pyridin-2-yl)-cyclopropyl]-carbamic acid benzyl ester (building block C18) and 3-(allyl-benzyloxycarbonyl-amino)-5-oxazol-2-yl-benzoic acid (building block A3).

Rf (DCM/MeOH/NH$_3$=90/10/1): 0.42.

MS (LC/MS, ES+): 610=[M+H]$^+$.

$^1$H-NMR (400 MHz, DMSO-d$_6$): 8.32 (d, 1H), 8.18 (s, 1H), 8.14 (d, 1H), 7.71 (s, 1H), 7.35 (s, 1H), 7.30 (s, 1H), 7.21-7.16 (m, 2H), 7.11-7.08 (m, 2H), 6.83 (d, 1H), 6.75-6.70 (m, 2H), 6.26 (s, br, 1H), 5.05-5.00 (m, 1H), 4.30-4.25 (m, 1H), 3.97-3.87 (m, 2H), 3.62-3.44 (m, 2H), 3.10-3.00 (m, 2H), 2.75-2.55 (m, 4H), 1.80-1.45 (m, 4H), 1.21 (s, 9H), 1.05-0.95 (m, 2H).

Example 59

(S)-4-{(R)-2-[1-(4-tert-Butyl-pyridin-2-yl)-cyclopropylamino]-1-hydroxy-ethyl}-19-(2-oxo-propoxy)-11,16-dioxa-3-aza-tricyclo[15.3.1.1*6,10*]docosa-1(20),6,8,10(22),17(21),18-hexaen-2-one The title compound is obtained by an analogous reaction sequence as for example 1, starting from [(2R,3S)-4-(3-allyloxy-phenyl)-3-tert-butoxycarbonylamino-2-hydroxy-butyl]-[1-(4-tert-butyl-pyridin-2-yl)-cyclopropyl]-carbamic acid benzyl ester (building block C18) and 3-allyloxy-5-(2-oxo-propoxy)-benzoic acid (building block A2).

Rf (DCM/MeOH/NH$_3$=90/10/1): 0.46.

MS (LC/MS, ES+): 616=[M+H]$^+$.

$^1$H-NMR (400 MHz, DMSO-d$_6$): 8.32 (d, 1H), 8.06 (d, 1H), 7.72 (s, 1H), 7.17 (t, 1H), 7.11 (d, 1H), 7.07 (s, 1H), 6.83 (d, 1H), 6.74 (d, 1H), 6.70 (s, 1H), 6.58 (s, 1H), 6.49 (t, 1H), 5.06 (d, 1H), 4.79 (s, 2H), 4.44-4.34 (m, 1H), 4.28-4.24 (m, 1H), 4.11-4.05 (m, 1H), 4.00-3.90 (m, 1H), 3.62-3.56 (m, 1H), 3.02 (dd, 1H), 2.75-2.69 (m, 2H), 2.62-2.58 (m, 1H), 2.13 (s, 3H), 1.85-1.63 (m, 4H), 1.29-1.15 (m, 3H), 1.26 (s, 9H), 1.02-0.92 (m, 2H).

Example 60

(S)-4-((R)-1-Hydroxy-2-{1-[3-(1-hydroxy-1-methylethyl)-phenyl]-cyclo-propylamino}-ethyl)-19-methoxymethyl-11-oxa-3,16-diaza-tricyclo[15.3.1.1*6,10*]-docosa-1 (21),6,8,10(22),17,19-hexaen-2-one a) (S)-4-((R)-2-{Benzyloxycarbonyl-[1-(3-bromophenyl)-cyclopropyl]-amino}-1-hydroxy-ethyl)-19-methoxymethyl-2-oxo-18-oxa-3,16-diaza-tricyclo[15.3.1.1*6,10*]docosa-1(21),6,8,10(22),13,17,19-heptaene-16-carboxylic acid benzyl ester The title compound is obtained by an analogous reaction sequence as for example 1 (steps 1a-b), starting from [(2R,3S)-4-(3-allyloxy-phenyl)-3-tert-butoxycarbonylamino-2-hydroxy-butyl]-[1-(3-bromo-phenyl)-cyclopropyl]-carbamic acid benzyl ester (building block C22) and 3-(allyl-benzyloxycarbonylamino)-5-methoxymethyl-benzoic acid (building block A7).

MS (ES+): 876 and 874=[M+H]+

HPLC (Nucleosil C18HD, 4×70 mm, 3 µm, 20-100% MeCN (6 min), 100% MeCN (1.5 min)) retention time=6.59 min b) (S)-4-{(R)-2-[1-(3-Bromo-phenyl)-cyclopropylamino]-1-hydroxy-ethyl}-19-methoxy-methyl-11-oxa-3,16-diaza-tricyclo[15.3.1.1*6,10*]docosa-1(21),6,8,10(22),13,17,19-heptaen-2-one (S)-4-((R)-2-{Benzyloxycarbonyl-[1-(3-bromo-phenyl)-cyclopropyl]-amino}-1-hydroxy-ethyl)-19-methoxymethyl-2-oxo-18-oxa-3,16-diaza-tricyclo[15.3.1.1*6,10*]docosa-1(21),6,8,10(22),13,17,19-heptaene-16-carboxylic acid benzyl ester (250 mg, 283 µmol, 1 eq) is dissolved in 4 ml of acetonitrile. TMSI (450 µl, 3.24 mmol, 11 eq) is added within 3 min at 0° C. The reaction mixture is stirred for 40 min at rt and then poured onto a solution of aq ammonia (7 ml, 25% in water) in MeOH (30 ml). The mixture is stirred at rt for 12 h. After concentration the residue is diluted with EtOAc and water. The organic layer is washed with brine, dried over sodium sulfate, and concentrated. The residue is purified by chromatography on silica (MeOH/DCM/NH$_3$ 20/380/1) to give the product.

MS (ES+): 608 and 606=[M+H]+

HPLC (Nucleosil C18HD, 4×70 mm, 3 µm, 20-100% MeCN (6 min), 100% MeCN (1.5 min)) retention time=3.78 min c) (S)-4-((R)-1-Hydroxy-2-{1-[3-(1-hydroxy-1-methyl-ethyl)-phenyl]-cyclopropylamino}-ethyl)-19-methoxymethyl-11-oxa-3,16-diaza-tricyclo[15.3.1.1*6,10*]docosa-1(21),6,8,10(22),13,17,19-heptaen-2-one (S)-4-{(R)-2-[1-(3-Bromo-phenyl)-cyclopropylamino]-1-hydroxy-ethyl}-19-methoxymethyl-11-oxa-3,16-diaza-tricyclo[15.3.1.1*6,10*]docosa-1(21),6,8,10(22),13,17,19-heptaen-2-one (20 mg, 33 µmol, 1 eq) is dissolved in 1 ml of THF. Iso-propyl magnesium chloride (2N in THF, 140 µl, 0.28 mmol, 8-75 eq) is added, and the reaction is cooled to −78° C. and stirred for 30 min at this temperature. Tert-butyl lithium (1.7 N in pentane, 129 µl, 0.20 mmol, 6A4 eq) is added, the reaction is stirred for 60 seconds, and acetone (0.7 ml) is added within 10 seconds. The reaction is warmed to −60° C. and stirred for 10 min. The reaction is warmed to −30° C., 1.5 ml of acetone are added followed by addition of water and EtOAc. The organic layer is dried over sodium sulfate and concentrated. The residue is purified by chromatography on silica (EtOH/DCM/NH$_3$ 4/96/0.7) to give the product.

MS (ES+): 586=[M+H]+

HPLC (Nucleosil C18HD, 4×70 mm, 3 µm, 20-100% MeCN (6 min), 100% MeCN (1.5 min)) retention time=3.32 min d) (S)-4-((R)-1-Hydroxy-2-{1-[3-(1-hydroxy-1-methyl-ethyl)-phenyl]-cyclopropylamino}-ethyl)-19-methoxymethyl-11-oxa-3,16-diaza-tricyclo[15.3.1.1*6,10*]docosa-1(21),6,8,10(22),17,19-hexaen-2-one (S)-4-((R)-1-Hydroxy-2-{1-[3-(1-hydroxy-1-methyl-ethyl)-phenyl]-cyclopropylamino}-ethyl)-19-methoxymethyl-11-oxa-3,16-diaza-tricyclo[15.3.1.1*6,10*]docosa-1(21),6,8,10(22),13,17,19-heptaen-2-one (10 mg, 17 µmol, 1 eq) is dissolved in 10 ml EtOH and added to Pd/C (10 mg) in 2 ml of EtOH under argon. The atmosphere is exchanged against hydrogen, and the reaction is stirred for 2 hours. The mixture is then filtered and concentrated. The product is purified by preparative HPLC (Sunfire Prep C18OBD, 19×50 mm, 5 µm, 5-50% MeCN (17 min), 50-100% MeCN (50 sec), 100% MeCN (70 sec)).

MS (ES+): 588=[M+H]+

HPLC (Nucleosil C18HD, 4×70 mm, 3 µm, 20-100% MeCN (6 min), 100% MeCN (1.5 min)) retention time=3.13 min $^1$H-NMR (400 MHz, DMSO-d$_6$): 7.95 (d, 1H), 7.35-7.02 (m, 6H), 6.80 (d, 1H), 6.74 (d, 1H), 6.61 (s, 1H), 6.58 (s, 1H), 6.51 (s, 1H), 5.88 (t, 1H), 4.90 (s, 1H), 4.79 (s, 1H), 4.28-4.20 (m, 3H), 3.97-3.82 (m, 2H), 3.50-3.32 (m, 2H), 3.28 (s, 3H), 3.08-2.98 (m, 2H), 2.70-2.30 (m, 3H), 1.81-1.50 (m, 4H), 1.41 (s, 6H), 1.00-0.79 (m, 4H).

Building block A1:
2-Allylamino-6-methoxymethyl-isonicotinic acid a) 2-Chloro-6-methyl-1-oxy-isonicotinic acid

2-Chloro-6-methyl-isonicotinic acid (6.86 g, 40 mmol, 1 eq) is dissolved in AcOH (40 ml). 2 ml of H$_2$O$_2$ (35% in H$_2$O) are added, and the reaction mixture is stirred for 76 h at 95° C. During that time, 2 ml of H$_2$O$_2$ (35% in H$_2$O) are added five times in regular intervals. The reaction mixture is concentrated and co-evaporated with toluene to give the product.

HPLC (Nucleosil C18HD, 4×70 mm, 3 µm, 5-100% MeCN (6 min), 100% MeCN (1.5 min)) retention time: 2.46 min.

$^1$H-NMR (400 MHz, DMSO-d$_6$): 8.05 (d, 1H), 7.96 (d, 1H), 2.46 (s, 3H).

b) 2-Chloro-6-hydroxymethyl-isonicotinic acid

2-Chloro-6-methyl-1-oxy-isonicotinic acid (7.3 g, 39 mmol, 1 eq) is dissolved in acetic acid anhydride, and the reaction mixture is stirred at 100° C. for 2 h. The mixture is then cooled to 40° C., and H$_2$O (40 ml) is added over 2 h. The mixture is concentrated, and the residue is purified by column chromatography using DCM/MeOH/AcOH in a ratio of 360 to 39 to 1 to give the acetylated product. The acetylated product is dissolved in MeOH (50 ml), and NaOH (25 ml, 2N in H$_2$O) is added. The reaction mixture is stirred for 4 h and then diluted, with HCl (2N in H$_2$O). The mixture is concentrated, and the residue is diluted with DCM. The organic layer is separated, dried over sodium sulfate, filtered and concentrated to give the product.

MS (ES−): 186=[M−H]−.

HPLC (Nucleosil C18HD, 4×70 mm, 3 µm, 5-100% MeCN (6 min), 100% MeCN (1.5 min)) retention time: 2.97 min.

c) 2-Chloro-6-methoxymethyl-isonicotinic acid

2-Chloro-6-hydroxymethyl-isonicotinic acid (4.6 g, 24.5 mmol, 1 eq) is dissolved in 100 ml of DMF. NaH (3.53 g, 73.5 mmol, 3 eq) is added at 0° C. The reaction mixture is stirred for 1 h at 10° C. MeI (7.63 ml, 123 mmol, 5 eq) is added within 15 min. The reaction mixture is stirred at rt for 4 h and then quenched with 10 ml of NaOH (4N in H$_2$O), diluted with 4N HCl in H$_2$O and concentrated. The residue is diluted with DCM/MeOH 9 to 1, and the organic layer is concentrated.

The residue is purified by column chromatography using DCM/EtOH/AcOH in a ratio of 180 to 19 to 1 to give the product.

MS (ES+): 202=[M+H]$^+$.

HPLC (Nucleosil C18HD, 4×70 mm, 3 μm, 5-100% MeCN (6 min), 100% MeCN (1.5 min)) retention time: 3.80 min.

d) 2-Chloro-6-methoxymethyl-isonicotinic acid tert-butyl ester

2-Chloro-6-methoxymethyl-isonicotinic acid (3.48 g, 15.5 mmol, 1 eq) is dissolved in toluene (60 ml), and the solution is heated to 80° C. N,N-dimethylformamide-di-tert-butylacetal (7.53 ml, 31 mmol, 2 eq) is added in portions over 8 h. The reaction mixture is then diluted with TBME and washed with aq NaHCO$_3$. The organic layer is dried over sodium sulfate, filtered and concentrated to give the product.

MS (ES+): 258=[M+H]$^+$.

HPLC (Nucleosil C18HD, 4×70 mm, 3 μm, 5-100% MeCN (6 min), 100% MeCN (1.5 min)) retention time: 6.24 min.

e) 2-Allylamino-6-methoxymethyl-isonicotinic acid tert-butyl ester

Pd(OAc)$_2$ (97 mg, 0.42 mmol, 0.05 eq), BINAP (269 mg, 0.42 mmol, 0.05 eq), Na-tert-butanolate (1.66 g, 17 mmol, 2 eq) and allylamine (784 mg, 12.7 mmol, 1.5 eq) are dissolved in toluene (80 ml), and the solution is stirred at 50° C. for 20 min. 2-Chloro-6-methoxymethyl-isonicotinic acid tert-butyl ester (1.38 g, 5.4 mmol, 1 eq) is dissolved in toluene (20 ml) and added to the reaction mixture at 50° C. within 20 min. The reaction mixture is stirred at 50° C. for 1 h, cooled to rt and poured on ice and TBME (200 ml). 4 g of NH$_4$Cl is added, and the mixture is stirred for 20 min. The organic layer is separated, dried over sodium sulfate, filtered and concentrated to give the product.

MS (ES+): 279=[M+H]$^+$.

HPLC (Nucleosil C18HD, 4×70 mm, 3 μm, 5-100% MeCN (6 min), 100% MeCN (1.5 min)) retention time: 4.33 min.

$^1$H-NMR (400 MHz, CDCl$_3$): 7.18 (s, 1H), 6.87 (s, 1H), 6.02-5.92 (m, 1H), 5.37-5.19 (m, 2H), 4.88-4.82 (m, 1H), 4.47 (s, 2H), 4.01-3.97 (m, 2H), 3.50 (s, 3H), 1.62 (s, 9H).

f) 2-Allylamino-6-methoxymethyl-isonicotinic acid

2-Allylamino-6-methoxymethyl-isonicotinic acid tert-butyl ester (270 mg, 0.97 mmol, 1 eq) is dissolved in 4N HCl in dioxane (4.9 ml). The reaction mixture is stirred for 83 h at rt, concentrated and co-evaporated with toluene to give the product.

MS (ES+): 223=[M+H]$^+$.

HPLC (Nucleosil C18HD, 4×70 mm, 3 μm, 5-100% MeCN (6 min), 100% MeCN (1.5 min)) retention time: 2.59 min.

Building block A2:3-Allyloxy-5-(2-oxo-propoxy)-benzoic acid a) 3-Allyloxy-5-(2-oxo-propoxy)-benzoic acid methyl ester 300 mg (1.44 mmol, 1 eq) of 3-allyloxy-5-hydroxy-benzoic acid methyl ester (Sörme et al., J. Am. Chem. Soc., 2005, 1737-1743) are dissolved in acetone (10 ml). KI (361 mg, 2.16 mmol, 1.5 eq), K$_2$CO$_3$ (603 mg, 4.32 mmol, 3 eq) and chloroacetone (192 μmol, 2.16 mmol, 1.5 eq) are added. The reaction mixture is refluxed for 19 h and then cooled to room temperature. HCl (1N in H$_2$O) and diethyl ether are added. The organic layer is washed with brine, dried over sodium sulfate, filtered and concentrated. The residue is purified by column chromatography using EtOAc/hexane in a ratio of 1 to 4 to give the product.

HPLC (Nucleosil C18HD, 4×70 mm, 3 μm, 20-100% MeCN (6 min), 100% MeCN (1.5 min)) retention time: 4.55 min.

$^1$H-NMR (400 MHz, CDCl$_3$): 7.26 (t, 1H), 7.17 (t, 1H), 6.70 (t, 1H), 6.10-6.00 (m, 1H), 5.50-5.30 (m, 2H), 4.60-4.57 (m, 4H), 3.93 (s, 3H), 2.32 (s, 3H).

MS: 265 (M+1), 263 (M−1).

b) 3-Allyloxy-5-(2-oxo-propoxy)-benzoic acid

3-Allyloxy-5-(2-oxo-propoxy)-benzoic acid is obtained by an analogous hydrolysis reaction as for building block A3, starting from 3-allyloxy-5-(2-oxo-propoxy)-benzoic acid methyl ester.

MS (ES$^-$): 249=[M−1]$^-$.

HPLC (Nucleosil C18HD, 4×70 mm, 3 μm, 20-100% MeCN (6 min), 100% MeCN (1.5 min)) retention time: 3.57 min.

Building block A3: 3-(Allyl-benzyloxycarbonyl-amino)-5-oxazol-2-yl-benzoic acid a) N-(2,2-Dimethoxy-ethyl)-5-nitro-isophthalamic acid methyl ester

Under ice cooling a solution of 22.1 g (90.7 mmol) of 3-chlorocarbonyl-5-nitro-benzoic acid methyl ester (U.S. Pat. No. 4,120,891) in 200 ml of DCM is added dropwise to a stirred suspension of 11.2 g (181 mmol) of K$_2$CO$_3$ and 11.7 ml (109 mmol) of aminoacetaldehyde dimethylacetal in 200 ml of DCM. The mixture is stirred at ambient temperature for 2 days, diluted with ethyl acetate and extensively washed with water. The organic phase is dried over sodium sulfate and evaporated to yield the product in the form of a yellow oil.

MS (ES$^-$): 311=[M−H]$^-$.

$^1$H-NMR (400 MHz, CDCl$_3$): 9.00 (t, 1H), 8.88 (t, 1H), 8.75 (t, 1H), 6.60 (br s, NH), 4.56 (t, 1H), 4-04 (s, 3H), 3-69 (t, 2H), 3-48 (s, 6H).

b) 5-Nitro-N-(2-oxo-ethyl)-isophthalamic acid methyl ester

A mixture of 29.7 g (95.1 mmol) of N-(2,2-dimethoxy-ethyl)-5-nitro-isophthalamic acid methyl ester in 300 ml of THF and 300 ml of 2N HCl is stirred overnight. Ethyl acetate is added, and the mixture is washed twice with brine. The organic phase is dried over sodium sulfate and evaporated to yield the product in the form of a yellow oil.

MS (ES$^-$): 265=[M−H]$^-$.

$^1$H-NMR (400 MHz, CDCl$_3$): 9.82 (s, 1H), 9.03 (t, 1H), 8.91 (t, 1H), 8.80 (t, 1H), 7.20 (br s, NH), 4.54 (d, 1H), 4.03 (s, 3H).

c) 3-Nitro-5-oxazol-2-yl-benzoic acid methyl ester

A mixture of hexachloroethane (42.7 g, 180 mmol) and 47.2 g of triphenylphosphine (180 mmol) in 1 l of acetonitrile is stirred for 20 minutes. A solution of 24 g (90.2 mmol) of 5-nitro-N-(2-oxo-ethyl)-isophthalamic acid methyl ester in 400 ml of acetonitrile is added, followed by 25.8 ml (361 mmol) of pyridine. After 18 h at rt, the mixture is diluted with 500 ml of ethyl acetate and washed with brine. The organic phase is dried over sodium sulfate and concentrated, and the residue is purified by chromatography on silica gel (EtOAc/hexane 1:3) to yield the product in the form of colorless crystals.

MS (ES+): 249=[M+H]$^+$.
$^1$H-NMR (400 MHz, CDCl$_3$): 9.11 (t, 1H), 9.06 (t, 1H), 8.96 (t, 1H), 7.86 (s, 1H), 7.39 (s, 1H), 4.05 (s, 3H).

d) 3-Amino-5-oxazol-2-yl-benzoic acid methyl ester

A solution of 11.7 g (47.1 mmol) of 3-nitro-5-oxazol-2-yl-benzoic acid methyl ester in 1 l of MeOH and 200 ml of THF is stirred under an atmosphere of hydrogen in the presence of 0.6 g of Pd/C (10%) until the hydrogen up-take ceases. The mixture is filtered over high-flow, and the filtrate is washed with THF and evaporated to yield the product.

MS (ES+): 219=[M+H]$^+$.
$^1$H-NMR (400 MHz, DMSO-d$_6$): 8.22 (t, 1H), 7.86 (s, 1H), 7.47 (t, 1H), 7.39 (s, 1H), 7.33 (t, 1H), 5.77 (br, 2H), 3.86 (s, 3H).

e) 3-Benzyloxycarbonylamino-5-oxazol-2-yl-benzoic acid methyl ester

A mixture of 10.3 g (47.2 mmol) of 3-amino-5-oxazol-2-yl-benzoic acid methyl ester, 25 g of anhydrous sodium carbonate and 7.69 ml (51.9 mmol) of benzyl chloroformate is stirred for 16 h at rt and filtered. The filtrate is concentrated, and the residue is chromatographed on silica gel (EtOAc/hexane 1:2) to yield the product in the form of colorless crystals.

MS (ES+): 353=[M+H]$^+$.
$^1$H-NMR (400 MHz, DMSO-d$_6$): 10.30 (s, 1H), 8.43 (s, 1H), 8.30 (s, 1H), 8.28 (s, 1H), 8.18 (s, 1H), 7.50-7.28 (m, 6H), 5.22 (s, 2H), 3.90 (s, 3H).

f) 3-(Allyl-benzyloxycarbonyl-amino)-5-oxazol-2-yl-benzoic acid methyl ester

3-Benzyloxycarbonylamino-5-oxazol-2-yl-benzoic acid methyl ester (330 mg, 0.927 mmol, 1 eq) is dissolved in THF (10 ml). NaH (48 mg, 60%, 1.21 mmol, 1.3 eq) is added in portions, and the reaction mixture is stirred for 30 min at rt. TBAI (35 mg, 92.7 µmol, 0.1 eq) and allyl bromide (119 µl, 1.39 mmol, 1.5 eq) are added, and the reaction mixture is stirred for 20 h and then quenched with HCl (1N in H$_2$O). The aqueous phase is extracted with EtOAc. The organic layer is washed with brine, dried over sodium sulfate, filtered and concentrated to give the product.

MS (ES+): 393=[M+H]$^+$.
$^1$H-NMR (400 MHz, CDCl$_3$): 8.60-8.55 (m, 1H), 8.17 (s, 1H), 8.00 (s, 1H), 7.72 (s, 1H), 7.32-7.24 (m, 6H), 6.0-5.8 (m, 1H), 5.20 (s, 3H), 5.18-5.15 (m, 1H), 4.38 (d, 2H), 3.95 (s, 3H).

g) 3-(Allyl-benzyloxycarbonyl-amino)-5-oxazol-2-yl-benzoic acid 3-(Allyl-benzyloxycarbonyl-amino)-5-oxazol-2-yl-benzoic acid methyl ester (300 mg, 757 µmol, 1 eq) is dissolved in methanol (10 ml) and H$_2$O (4 ml). LiOH*H$_2$O (100 mg, 2.37 mmol, 3.13 eq) is added to the reaction mixture, which is stirred for 8 h at rt and then diluted with HCl (1N in H$_2$O) and DCM. The combined organic solvents are separated and washed with brine, dried over sodium sulfate, filtered and concentrated. The resulting crystals are washed with hexane and dried under vacuum to give the product.

MS (ES+): 379=[M+H]$^+$.
$^1$H-NMR (400 MHz, DMSO-d$_6$): 8.30 (m, 1H), 8.24 (m, 1H), 8.10 (dd, 1H), 7.95 (dd, 1H), 7.40 (s, 1H), 7.35-7.20 (m, 5H), 6.0-5.8 (m, 1H), 5.18-5.12 (m, 4H), 4.38 (d, 2H).

Building block A4:
5-Allyloxy-N,N-dimethyl-isophtalamic acid a) 5-Allyloxy-isophthalic acid monomethyl ester The product is obtained as described by Fang et al., J. Am. Chem. Soc., 1998, 8543-8544.

b) 5-Allyloxy-N,N-dimethyl-isophthalmic acid methyl ester

A solution of 2.17 g (9.18 mmol) of 5-allyloxy-isophthalic acid monomethyl ester in 9.2 ml of thionyl chloride is heated to reflux for 1 h. Excess thionyl chloride is removed under reduced pressure to yield 3-allyloxy-5-chlorocarbonyl-benzoic acid methyl ester in the form of a color-less oil, which is used without further purification. To a solution of 2.36 g (9.18 mmol) of 3-allyloxy-5-chlorocarbonyl-benzoic acid methyl ester in 9 ml of DCM 27.6 ml of a 1 M solution of dimethylamine in THF (3 eq.) are added at 0° C. The mixture is stirred at rt for 2 h. 100 ml of a half-saturated aq ammonium chloride solution are added. The mixture is extracted with TBME (2×75 ml), and the combined organic layers are washed with 50 ml of water, dried over sodium sulfate and evaporated. The residue is purified by chromatography on silica gel (EtOAc) to give the product as a colorless oil.

Rf (EtOAc): 0.48.
MS (ES+): 364=[M+H]$^+$.
$^1$H-NMR (400 MHz, DMSO-d$_6$): 7.49-7.46 (m, 2H), 7.24-7.20 (m, 1H), 6.08-5.97 (m, 1H), 5.40 (dd, 1H), 5.27 (dd, 1H), 4.68 (d, 1H), 3.85 (s, 3H), 2.99 (br s, 3H), 2.88 (br s, 3H).

c) 5-Allyloxy-N,N-dimethyl-isophthalamic acid

To a solution of 2 g (7.6 mmol) of 5-allyloxy-N,N-dimethyl-isophthalamic acid methyl ester in 16.8 ml of THF/MeOH (1:1) 8.4 ml of 1 M KOH (1.1 eq.) are added at 0° C. The mixture is stirred at rt for 3 h. The organic solvents are removed under reduced pressure, and the aqueous phase is acidified with HCl to pH 2 and extracted with DCM/EtOH (80:20) (2×38 ml). The combined organic layers are washed with 8 ml of water, dried over sodium sulfate and evaporated to give the product in the form of a colorless solid (m.p.: 93-95° C.).

MS (ES+): 250=[M+H]$^+$
$^1$H-NMR (400 MHz, DMSO-d$_6$): 13.28 (br s, 1H), 7.48-7.43 (m, 2H), 7.18-7.13 (m, 1H), 6.09-5.98 (m, 1H), 5.39 (dd, 1H), 5.26 (dd, 1H), 4.64 (d, 1H), 2.97 (br s, 3H), 2.88 (br s, 3H).

Building block A5:
3-Acetyl-5-(allyl-benzyloxycarbonyl-amino)-benzoic acid a) 5-Benzyloxycarbonylamino-isophthalic acid monomethyl ester Monomethyl-5-nitroisophthalate (50 g, 220 mmol, 1 eq) is dissolved in a mixture of 650 ml of MeOH and 350 ml of THF.

3 g of Pd/C are added, and the reaction mixture is hydrogenated overnight under 1 bar of $H_2$ and then filtered. The filtrate is concentrated, and the residue is dissolved in a mixture of THF (200 ml) and aq $NaHCO_3$ (400 ml). CbzCl (62 ml, 50% in toluene, 184 mmol, 0.9 eq) is added, the reaction mixture is stirred for 1 h, CbzCl (31 ml, 50% in toluene, 92 mmol, 0.45 eq) is added, and the reaction mixture is stirred overnight. The white solid formed is washed with water and diethyl ether to give the product.

MS (ES−): 328=[M−H]⁻.

HPLC (Nucleosil C18HD, 4×70 mm, 3 μm, 20-100% MeCN (6 min), 100% MeCN (1.5 min)) retention time: 4.36 min.

¹H-NMR (400 MHz, DMSO-$d_6$): 8.40 (s, 1H), 8.38 (s, 1H), 8.17 (s, 1H), 7.50-7.37 (m, 5H), 5.21 (s, 2H), 3.92 (s, 3H).

b) 5-Benzyloxycarbonylamino-5-hydroxymethyl-benzoic acid methyl ester

5-Benzyloxycarbonylamino-isophthalic acid monomethyl ester (10 g, 30.1 mmol, 1 eq) and $Et_3N$ (5 ml, 36.1 mmol, 1.2 eq) are suspended in a mixture of THF (200 ml) and N-methylpyrrolidone (200 ml). Isopropylchloroformate (42 ml, 1 N in toluene, 42 mmol, 1.4 eq) is added, and the reaction mixture is stirred for 30 min at 0° C. and then diluted with diethyl ether and water. The organic layer is washed with 0.1 N HCl and brine. $NaBH_4$ (3.82 g, 101 mmol, 3.36 eq) is dissolved in $H_2O$ (100 ml), and the solution is added to the reaction mixture, which is then stirred for 1 h. Diethyl ether and $H_2O$ are added, and the organic layer is separated, washed with brine, dried over sodium sulfate, filtered and concentrated. The residue is purified by column chromatography using EtOAc/hexane in a ratio of 1 to 2 to give the product.

MS (ES+): 333=[M+$NH_4$]⁺.

¹H-NMR (400 MHz, DMSO-$d_6$): 8.07 (s, 1H), 7.68 (s, 1H), 7.60 (s, 1H), 7.50-7.37 (m, 5H), 5.39 (t, 1H), 5.20 (s, 2H), 4.54 (d, 2H), 3.86 (s, 3H).

c) 3-Benzyloxycarbonylamino-5-(tert-butyl-dimethyl-silanyloxymethyl)-benzoic acid methyl ester 5-Benzyloxycarbonylamino-5-hydroxymethyl-benzoic acid methyl ester (14.3 g, 45.4 mmol, 1 eq) is dissolved in DMF (40 ml). Tert-butylchlorodimethylsilane (8.3 g, 54.9 mmol, 1.21 eq), imidazole (3.1 g, 45.8 mmol, 1.01 eq) and 4-dimethylaminopyridine (279 mg, 2.28 mmol, 0.05 eq) are added. The reaction mixture is stirred for 8 h at rt and then diluted with diethyl ether and aq $NaHCO_3$. The organic layer is separated, dried over $MgSO_4$, filtered and concentrated. The residue is dissolved in diethyl ether, and hexane is added to precipitate the product, which is filtered off and dried under vacuum.

MS (ES+): 447=[M+$NH_4$]⁺.

HPLC (Nucleosil C18HD, 4×70 mm, 3 μm, 20-100% MeCN (6 min), 100% MeCN (1.5 min)) retention time: 7.09 min.

¹H-NMR (400 MHz, $CDCl_3$): 7.96 (s, 1H), 7.76 (s, 1H), 7.67 (s, 1H), 7.47-7.37 (m, 5H), 6.82 (s, 1H), 5.26 (s, 2H), 4.80 (s, 2H), 3.93 (s, 3H), 0.99 (s, 9H), 0.18 (s, 6H).

d) 3-(Allyl-benzyloxycarbonyl-amino)-5-(tert-butyl-dimethyl-silanyloxymethyl)-benzoic acid methyl ester 3-Benzyloxycarbonylamino-5-(tert-butyl-dimethyl-silanyloxymethyl)-benzoic acid methyl ester (14.0 g, 29.8 mmol, 1 eq) is dissolved in 200 ml of DMF. NaH (1.63 g, 55%, 37.3 mmol, 1.25 eq) is added at 0° C., and the reaction mixture is stirred for 1 h at 0° C. Allyl bromide (3.30 ml, 37.3 mmol, 1.25 eq) is added, and the reaction mixture is stirred for 30 min at rt, poured onto ice water and diluted with EtOAc. The organic layer is separated, dried over $MgSO_4$, filtered and concentrated to give the product.

MS (ES+): 487=[M+$NH_4$]⁺.

HPLC (Nucleosil C18HD, 4×70 mm, 3 μm, 20-100% MeCN (6 min), 100% MeCN (1.5 min)) retention time: 7.43 min.

¹H-NMR (400 MHz, $CDCl_3$): 7.86 (s, 1H), 7.82 (s, 1H), 7.49 (s, 1H), 7.40-7.30 (m, 5H), 6.00-5.88 (m, 1H), 5.26-5.17 (s, 4H), 4.80 (s, 2H), 4.38 (d, 2H), 3.93 (s, 3H), 0.99 (s, 9H), 0.18 (s, 6H).

e) 3-Allyl-benzyloxycarbonyl-amino)-5-hydroxymethyl-benzoic acid methyl ester 3-(Allyl-benzyloxycarbonyl-amino)-5-(tert-butyl-dimethyl-silanyloxymethyl)-benzoic acid methyl ester (19.8 g, 37.2 mmol, 1 eq) is dissolved in THF (220 ml). TBAF in THF (100 ml, 1 N in THF, 100 mmol, 2.68 eq) is added, and the reaction mixture is stirred for 16 h at rt and then concentrated. The residue is purified by column chromatography using hexane/EtOAc in a ratio of 7 to 3 to give the product.

MS (ES+): 373=[M+$NH_4$]⁺.

HPLC (Nucleosil C18HD, 4×70 mm, 3 μm, 20-100% MeCN (6 min), 100% MeCN (1.5 min)) retention time: 4.63 min.

¹H-NMR (400 MHz, $CDCl_3$): 7.92 (s, 1H), 7.86 (s, 1H), 7.49 (s, 1H), 7.40-7.30 (m, 5H), 6.00-5.88 (m, 1H), 5.26-5.17 (s, 4H), 4.76 (s, 2H), 4.38 (d, 2H), 3.92 (s, 3H).

f) 3-(Allyl-benzyloxycarbonyl-amino)-5-formyl-benzoic acid methyl ester 3-(Allyl-benzyloxycarbonyl-amino)-5-hydroxymethyl-benzoic acid methyl ester (1.4 g, 2.84 mmol, 1 eq) is dissolved in DCM. Dess-Martin reagent (1.49 g, 3.40 mmol, 1.2 eq) is added, and the reaction mixture is stirred for 1 h at rt. The organic layer is washed with 1 N HCl, water and brine, dried over $MgSO_4$, filtered and concentrated. The residue is purified by column chromatography using EtOAc/hexane in a ratio of 1 to 4 to give the product.

MS (ES+): 371=[M+$NH_4$]⁺.

HPLC (Nucleosil C18HD, 4×70 mm, 3 μm, 20-100% MeCN (6 min), 100% MeCN (1.5 min)) retention time: 5.36 min.

g) 3-(Allyl-benzyloxycarbonyl-amino)-5-(1-hydroxy-ethyl)-benzoic acid methyl ester 3-(Allyl-benzyloxycarbonyl-amino)-5-formyl-benzoic acid methyl ester (900 mg, 2.55 mmol, 1 eq) is dissolved in THF (12 ml). Methylmagnesium chloride (1.50 ml, 22% in THF, 3.80 mmol, 1.5 eq) is added at −78° C., and the reaction mixture is stirred at −78° C. for 1 h, quenched with aq $NH_4Cl$ (20 ml), warmed to rt, diluted with $H_2O$ and extracted with EtOAc. The organic layer is washed with water and brine, dried over sodium sulfate, filtered and concentrated. The residue is purified by column chromatography using EtOAc/hexane in a ratio of 2 to 3 to give the product.

MS (ES+): 387=[M+NH$_4$]$^+$.
HPLC (Nucleosil C18HD, 4×70 mm, 3 μm, 20-100% MeCN (6 min), 100% MeCN (1.5 min)) retention time: 4.85 min.

h) 3-Acetyl-5-(allyl-benzyloxycarbonyl-amino)-benzoic acid methyl ester 3-(Allyl-benzyloxycarbonyl-amino)-5-(1-hydroxy-ethyl)-benzoic acid methyl ester (661 mg, 1.70 mmol, 1 eq) is dissolved in DCM. Dess-Martin reagent (1.49 g, 3.40 mmol, 1.2 eq) is added, and the reaction mixture is stirred for 1 h at rt. The organic layer is washed with 1 N HCl, water and brine, dried over MgSO$_4$, filtered and concentrated. The residue is purified by column chromatography using EtOAc/hexane in a ratio of 1 to 4 to give the product.
MS (ES+): 385=[M+NH$_4$]$^+$.
HPLC (Nucleosil C18HD, 4×70 mm, 3 μm, 20-100% MeCN (6 min), 100% MeCN (1.5 min)) retention time: 5.38 min.

i) 3-Acetyl-5-(allyl-benzyloxycarbonyl-amino)-benzoic acid

3-Acetyl-5-(allyl-benzyloxycarbonyl-amino)-benzoic acid methyl ester (572 mg, 1.56 mmol, 1 eq) is dissolved in MeOH (20 ml). 3.1 ml of aq LiOH (1 N in H$_2$O) are added, and the reaction mixture is stirred for 1 h at rt and diluted with DCM and 2 N HCl in H$_2$O. The organic layer is separated, dried over sodium sulfate, filtered and concentrated to give the product.
MS (ES−): 352=[M−H]$^−$.
HPLC (Nucleosil C18HD, 4×70 mm, 3 μm, 20-100% MeCN (6 min), 100% MeCN (1.5 min)) retention time: 4.50 min.
$^1$H-NMR (400 MHz, CDCl$_3$): 8.53 (s, 1H), 8.25 (s, 1H), 8.17 (s, 1H), 7.43-7.30 (m, 5H), 6.01-5.91 (m, 1H), 5.28-5.19 (m, 4H), 4.41 (d, 2H), 2.67 (s, 3H).

Building block A6: 3-Acetyl-5-allyloxy-benzoic acid a) 3-Allyloxy-5-hydroxymethyl-benzoic acid methyl ester The product is obtained using the reaction procedure described by Fang et al., J. Am. Chem. Soc., 1998, 8543-8544.

b) 3-Allyloxy-5-formyl-benzoic acid methyl ester

3-Allyloxy-5-hydroxymethyl-benzoic acid methyl ester (1 g, 4.45 mmol, 1 eq) is dissolved in DCM (40 ml). Dess-Martin reagent (2.34 g, 5.35 mmol, 1.2 eq) is added, and the reaction mixture is stirred for 1 h at rt and then diluted with ether and water. The organic layer is washed with aq Na$_2$CO$_3$, dried over sodium sulfate, filtered and concentrated to give the product.
HPLC (Nucleosil C18HD, 4×70 mm, 3 μm, 20-100% MeCN (6 min), 100% MeCN (1.5 min)) retention time: 4.72 min.
$^1$H-NMR (400 MHz, CDCl$_3$): 10.0 (s, 1H), 8.17 (s, 1H), 7.86 (dd, 2H), 7.62 (dd, 1H), 7.40-7.20 (m, 5H), 6.16-6.02 (m, 1H), 5.50-5.32 (m, 2H), 4.72 (d, 2H), 3.99 (s, 3H).

c) 3-Allyloxy-5-(1-hydroxy-ethyl)-benzoic acid methyl ester

3-Allyloxy-5-formyl-benzoic acid methyl ester (800 mg, 3.63 mmol, 1 eq) is dissolved in THF. MeMgCl (1.85 ml, 22% in THF, 5.45 mmol, 1.5 eq) is added at −78° C., and the reaction mixture is stirred at −78° C. for 1 h, quenched with aq NH$_4$Cl, warmed to rt and diluted with H$_2$O and EtOAc. The organic layer is separated, washed with brine, dried over sodium sulfate, filtered and concentrated. The residue is purified by column chromatography using EtOAc/hexane in a ratio of 1 to 9 to give the product.
MS (ES+): 254=[M+NH$_4$]$^+$.
HPLC (Nucleosil C18HD, 4×70 mm, 3 μm, 20-100% MeCN (6 min), 100% MeCN (1.5 min)) retention time: 4.07 min.
$^1$H-NMR (400 MHz, CDCl$_3$): 7.66 (s, 1H), 7.50 (dd, 1H), 7.20 (dd, 1H), 6.17-6.02 (m, 1H), 5.50-5.33 (m, 2H), 4.94 (q, 1H), 4.62 (d, 2H), 3.94 (s, 3H), 1.93 (s, 1H), 1.55 (d, 3H).

d) 3-Acetyl-5-allyloxy-benzoic acid methyl ester

3-Allyloxy-5-(1-hydroxy-ethyl)-benzoic acid methyl ester (570 mg, 2.41 mmol, 1 eq) is dissolved in DCM (20 ml). Dess-Martin reagent (1.23 g, 2.89 mmol, 1.2 eq) is added, and the reaction mixture is stirred for 1 h at rt and washed with 1 N HCl in H$_2$O and then brine. The organic layer is dried over sodium sulfate, filtered and concentrated. The residue is purified by column chromatography using EtOAc/hexane in a ratio of 1 to 4 to give the product.
MS (ES+): 252=[M+NH$_4$]$^+$.
HPLC (Nucleosil C18HD, 4×70 mm, 3 μm, 20-100% MeCN (6 min), 100% MeCN (1.5 min)) retention time: 4.78 min.
$^1$H-NMR (400 MHz, CDCl$_3$): 8.20 (s, 1H), 7.80 (dd, 1H), 7.69 (dd, 1H), 6.13-6.03 (m, 1H), 5.50-5.34 (m, 2H), 4.63 (d, 2H), 3.95 (s, 3H), 2.62 (s, 3H).

e) 3-Acetyl-5-allyloxy-benzoic acid

The product can be obtained by an analogous hydrolysis reaction as for building block A3, starting from 3-acetyl-5-allyloxy-benzoic acid methyl ester.
MS (ES+): 238=[M+NH$_4$]$^+$.
HPLC (Nucleosil C18HD, 4×70 mm, 3 μm, 20-100% MeCN (6 min), 100% MeCN (1.5 min)) retention time: 3.74 min.
$^1$H-NMR (400 MHz, CDCl$_3$): 8.04 (s, 1H), 7.72-7.67 (m, 2H), 6.13-6.02 (m, 1H), 5.45-5.29 (m, 2H), 4.73 (d, 2H), 2.62 (s, 3H).

Building block A7: 3-(Allyl-benzyloxycarbonyl-amino)-5-methoxymethyl-benzoic acid a) 3-Hydroxymethyl-5-nitro-benzoic acid methyl ester Monomethyl-5-nitroisophthalate (22.5 g, 100 mmol, 1 eq) and Et$_3$N (16.7 ml, 120 mmol, 1.2 eq) are dissolved in THF (200 ml). The solution is stirred at 0° C., and isopropylchloroformate in toluene (140 ml, 1 N in toluene, 140 mmol, 1.4 eq) is added within 30 min. After stirring for 90 min at 0° C., the reaction mixture is poured on ice and 50 ml of 0.1 N aq HCl and then diluted with TBME. The organic layer is separated, dried over sodium sulfate, filtered and concentrated. The residue is dissolved in 300 ml of THF, and the solution is stirred at rt. A solution of NaBH$_4$ (12.5 g, 330 mmol, 3.3 eq) in 100 ml of ice water is added within 15 min. The reaction mixture is stirred for 1 h at rt and then diluted with TBME and H$_2$O. The organic layer is washed with brine, dried over sodium sulfate, filtered and concentrated giving the product.

HPLC (Nucleosil C18HD, 4×70 mm, 3 μm, 20-100% MeCN (6 min), 100% MeCN (1.5 min)) retention time: 3.20 min.

¹H-NMR (400 MHz, CDCl₃): 8.80 (s, 1H), 8.48 (s, 1H), 8.39 (s, 1H), 4.93 (s, 2H), 4.01s, 3H).

b) 3-Methoxymethyl-5-nitro-benzoic acid methyl ester

3-Hydroxymethyl-5-nitro-benzoic acid methyl ester (8.0 g, 37.9 mmol, 1 eq) is dissolved in 80 ml of DMF. NaH (2.15 g, 49.3 mmol, 1.3 eq) is added at 0° C. The suspension is stirred for 30 min at rt, then methyl iodide (4.57 ml, 49.3 mmol, 1.3 eq) is added. The reaction mixture is stirred for 3 h at rt and then quenched with 1N HCl and TBME. The organic layer is dried over sodium sulfate, filtered and concentrated. The residue is purified by column chromatography using EtOAc/hexane in a ratio of 1 to 3 to give the product.

HPLC (Nucleosil C18HD, 4×70 mm, 3 μm, 20-100% MeCN (6 min), 100% MeCN (1.5 min)) retention time: 4.45 min.

¹H-NMR (400 MHz, CDCl₃): 8.80 (s, 1H), 8.43 (s, 1H), 8.38 (s, 1H), 4.61 (s, 2H), 4.00 (s, 3H), 3.52 (s, 3H).

c) 3-Benzyloxycarbonylamino-5-methoxymethyl-benzoic acid methyl ester

3-Methoxymethyl-5-nitro-benzoic acid methyl ester (3.80 g, 16.9 mmol, 1 eq) is dissolved in EtOH (80 ml). SnCl₂*2H₂O (1.58 g, 7 mmol, 7 eq) is added, and the reaction mixture is heated to 75° C. for 90 min and then diluted with EtOAc and aq NaHCO₃. The organic layer is dried over sodium sulfate, filtered and concentrated. The residue is dissolved in THF, and CbzCl (0.4 ml, 1.30 mmol, 1.2 eq) is added to the solution, followed by aq NaHCO₃. The reaction mixture is stirred for 1 h at rt and then diluted with EtOAc. The organic layer is dried over sodium sulfate, filtered and concentrated. The residue is purified by column chromatography using EtOAc/hexane in a ratio of 1 to 4 to give the product.

MS (ES−): 328=[M−H]⁻.

HPLC (Nucleosil C18HD, 4×70 mm, 3 μm, 20-100% MeCN (6 min), 100% MeCN (1.5 min)) retention time: 5.04 min.

¹H-NMR (400 MHz, CDCl₃): 7.94 (s, 1H), 7.84-7.70 (m, 2H), 7.46-7.38 (m, 5H), 6.82 (s, 1H), 5.25 (s, 2H), 4.52 (s, 2H), 3.93 (s, 3H), 3.42 (s, 3H).

d) 3-(Allyl-benzyloxycarbonyl-amino)-5-methoxymethyl-benzoic acid methyl ester

3-Benzyloxycarbonylamino-5-methoxymethyl-benzoic acid methyl ester (1.98 g, 6 mmol, 1 eq) is dissolved in 25 ml of DMF. NaH (327 mg, 55%, 7.5 mmol, 1.25 eq) is added, and the reaction mixture is stirred for 40 min at 0° C. Allyl bromide (653 μl, 7.5 mmol, 1.25 eq) is added, and the reaction mixture is stirred for 30 min at rt, then poured on ice water and extracted with EtOAc. The organic layer is separated, dried over sodium sulfate, filtered and concentrated. The residue is purified by column chromatography using EtOAc/hexane in a ratio of 1 to 4 to give the product.

MS (ES+): 387=[M+NH₄]⁺.

HPLC (Nucleosil C18HD, 4×70 mm, 3 μm, 20-100% MeCN (6 min), 100% MeCN (1.5 min)) retention time: 5.55 min.

¹H-NMR (400 MHz, CDCl₃): 7.92-7.88 (m, 2H), 7.48 (s, 1H), 7.40-7.30 (m, 5H), 6.00-5.87 (m, 1H), 5.20-5.17 (m, 4H), 4.50 (s, 2H), 4.34 (d, 2H), 3.94 (s, 3H), 3.40 (s, 3H).

e) 3-(Allyl-benzyloxycarbonyl-amino)-5-methoxymethyl-benzoic acid

The product can be obtained by an analogous hydrolysis reaction as for building block A3, starting from 3-allyl-benzyloxycarbonyl-amino)-5-methoxymethyl-benzoic acid methyl ester.

MS (ES−): 354=[M−H]⁻.

HPLC (Nucleosil C18HD, 4×70 mm, 3 μm, 20-100% MeCN (6 min), 100% MeCN (1.5 min)) retention time: 4.64 min.

¹H-NMR (400 MHz, CDCl₃): 7.94 (s, 2H), 7.55 (s, 1H), 7.40-7.20 (m, 5H), 6.00-5.88 (m, 1H), 5.22-5.18 (m, 4H), 4.53 (s, 2H), 4.37 (d, 2H), 3.40 (s, 3H).

Building block A8:
2-Allylamino-6-methyl-isonicotinic acid hydrochloride a) 2-Chloro-6-methyl-isonicotinic acid tert-butyl ester A solution of 5.0 g (29 mmol) of 2-chloro-6-methyl-isonicotinic acid in 50 ml of chloroform is heated to reflux. 14 ml (58 mmol, 2 eq) of di-tert-butoxymethyl-dimethyl-amine are added dropwise over 30 min. After a reaction time of 1.5 h and 3.5 h, further portions of di-tert-butoxymethyl-dimethyl-amine (each time 14 ml, 58 mmol, 2 eq) are added. After a reaction time of 4.5 h, the reaction mixture is cooled to rt and diluted with EtOAc. The organic layer is washed with aq sodium bicarbonate and then brine, dried over magnesium sulfate, filtered and concentrated. The residue is purified by chromatography on silica (flashmaster, hexane to hexane/EtOAc 95/5) to give the product in the form of a white solid.

Rf (DCM/methanol=95:5): 0.36.

MS (LC/MS): 172/174=[M+H-tert-butyl]⁺.

¹H-NMR (400 MHz, CDCl₃): 7.65 (s, 1H), 7.60 (s, 1H), 2.63 (s, 3H), 1.63 (s, 9H).

b) 2-Allylamino-4-methyl-isonicotinic acid tert-butyl ester

A mixture of 1.87 ml (24 mmol, 1.1 eq) of allylamine, 0.254 g (0.05 eq) of Pd(OAc)₂, 0.705 g (0.05 eq) of BINAP and 4.78 g (48 mmol, 2.2 eq) of sodium tert-butylate in 110 ml of toluene is heated to 60° C. under an atmosphere of nitrogen. A solution of 5.0 g (22 mmol) of 2-chloro-6-methyl-isonicotinic acid tert-butyl ester in 40 ml of toluene is added dropwise over 30 min, and the reaction mixture is stirred at 60° C. for 2.5 h and, after cooling to rt, diluted with EtOAc. The organic layer is washed with aq sodium bicarbonate and then brine, dried over sodium sulfate and concentrated at reduced pressure. The residue is purified by chromatography on silica (flashmaster, hexane to hexane/EtOAc 80/20) to give the product.

Rf (hexane/EtOAc=70/30): 0.38.

MS (LC/MS): 193=[M+H □ tert-butyl]⁺.

¹H-NMR (400 MHz, CDCl₃): 6.96 (s, 1H), 6.76 (s, 1H), 6.02-5.93 (m, 1H), 5.31 (d, 1H), 5.20 (d, 1H), 4.81 (br s, 1H), 4.00-3.95 (m, 2H), 2.45 (s, 3H), 1.61 (s, 9H).

c) 2-Allylamino-4-methyl-isonicotinic acid hydrochloride

A solution of 0-26 g (1.0 mmol) of 2-allylamino-6-methyl-isonicotinic acid tert-butyl ester in 9.2 ml (35 eq) of 4 N HCl in dioxane is heated for 2 h to 60° C. The evaporation of the solvent gives the product in the form of a brownish foam.

Rf (DCM/MeOH=70/30): 0.37.

MS (LC/MS): 193=[M+H]⁻.

$^1$H-NMR (400 MHz, CDCl$_3$): 8.61 (br s, 1H), 7.24 (s, 1H), 7.10 (s, 1H), 5.95-5.86 (m, 1H), 5.39 (d, 1H), 5.33 (d, 1H), 4.07 (br s, 2H), 2.68 (s, 3H).

Building block A9: 3-Allyloxy-5-[methoxy-(propane-1-sulfonyl)-amino]-benzoic acid allyl ester a) 3-Allyloxy-5-nitro-benzoic acid allyl ester 3-Nitro-5-hydroxy-benzoic acid (500 mg, 2.73 mmol, 1 eq) is dissolved in acetone (7 ml). Potassium carbonate (877 mg, 6.28 mmol, 2.3 eq), allyl bromide (1.21 ml, 13.92 mmol, 5.1 eq) and potassium iodide (907 mg, 5.46 mmol, 2 eq) are added to the reaction mixture. The reaction mixture is heated for 40 h at reflux temperature and then diluted with water and EtOAc. The organic layer is separated, washed with brine, dried over sodium sulfate, filtered and concentrated. The product is purified by chromatography on silica (EtOAc/hexane 1/9).

MS (ES+): 281 [M+NH$_4$]$_+$

HPLC (Nucleosil C18HD, 4×70 mm, 3 μm, 20-100% MeCN (6 min), 100% MeCN (1.5 min)) retention time=5.85 min b) 3-Allyloxy-5-amino-benzoic acid allyl ester 3-Allyloxy-5-nitro-benzoic acid allyl ester (540 mg, 2.05 mmol, 1 eq) is dissolved in EtOH (15 ml). SnCl$_2$*2H$_2$O (3.31 g, 14.4 mmol, 7 eq) is added and the reaction is heated at 75° C. for 1.5 h. The reaction mixture is cooled to rt and diluted with 2N aq hydrochloric acid and EtOAc. The organic layer is separated, washed with brine, dried over magnesium sulfate, filtered, and concentrated. The product is purified by chromatography on silica (EtOAc/hexane/NH$_3$ 30/70/0.2).

MS (ES+): 234 [M+H]$^+$

HPLC (Nucleosil C18HD, 4×70 mm, 3 μm, 20-100% MeCN (6 min), 100% MeCN (1.5 min)) retention time=3.87 min c) 3-Allyloxy-5-(propane-1-sulfonylamino)-benzoic acid allyl ester 3-Allyloxy-5-amino-benzoic acid allyl ester (300 mg, 1.29 mmol, 1 eq) is dissolved in DCM (25 ml). Pyridine (737 μl, 10.3 mmol, 8 eq) and propane sulfonyl chloride (634 μl, 5.66 mmol, 4.4 eq) are added and the mixture is stirred for 4 h at rt. The reaction is diluted with 1N aq hydrochloric acid and EtOAc. The organic layer is separated, washed with brine, dried over sodium sulfate, filtered and concentrated. The product is purified by chromatography on silica (EtOAc/hexane 3/7).

MS (ES+): 357 [M+NH$_4$]$^+$

HPLC (Nucleosil C18HD, 4×70 mm, 3 μm, 20-100% MeCN (6 min), 100% MeCN (1.5 min)) retention time=5.24 min d) 3-Allyloxy-5-[methyl-(propane-1-sulfonyl)-amino]-benzoic acid allyl ester Potassium carbonate (188 mg, 1.35 mmol, 2.2 eq) and methyl iodide (85 μl, 1.35 mmol, 2.2 eq) are added to the solution of 3-allyloxy-5-(propane-1-sulfonylamino)-benzoic acid allyl ester (260 mg, 0.613 mmol, 1 eq) in 12 ml of acetonitrile. The reaction is stirred for 18 h at rt. The mixture is filtered and concentrated. The product is purified by chromatography on silica (EtOAc/hexane 1/4).

MS (ES+): 371 [M+NH$_4$]$^+$

HPLC (Nucleosil C18HD, 4×70 mm, 3 μm, 20-100% MeCN (6 min), 100% MeCN (1.5 min)) retention time=5.62 min e) 3-Allyloxy-5-[methyl-(propane-1-sulfonyl)-amino]-benzoic acid 3-Allyloxy-5-[methyl-(propane-1-sulfonyl)-amino]-benzoic acid allyl ester (174 mg, 0.492 mmol, 1 eq) is dissolved in 7 ml MeOH and 0.5 ml 4N aq sodium hydroxide. After stirring for 3 h at rt the reaction mixture is diluted with 2N aq hydrochloric acid and EtOAc. The organic layer is separated, dried over magnesium sulfate, filtered and concentrated to give the product.

MS (ES−): 312 [M−H]⁻

HPLC (Nucleosil C18HD, 4×70 mm, 3 μm, 20-100% MeCN (6 min), 100% MeCN (1.5 min)) retention time=4.22 min Building block A10: 3-(3-Methanesulfonyloxy-propoxy)-5-methoxymethyl-benzoic acid methyl ester a) 3-Allyloxy-5-hydroxymethyl-benzoic acid methyl ester 5-Allyloxy-isophtalic acid monomethyl ester (Fang et al., J. Am. Chem. Soc. 1998, 8543-8544) (6.14 g, 26 mmol, 1 eq) is dissolved in 200 ml THF. Et$_3$N (4.4 ml, 31.2 mmol, 1.2 eq) is added, and the reaction mixture is cooled to 0° C. After addition of isopropyl chloroformate (1N in toluene, 36.4 ml, 36 mmol, 1.4 eq) the reaction is stirred for 1 h at 0° C. Water (50 ml) and TBME (300 ml) are added. The organic layer is separated, washed with aq bicarbonate and brine, dried over sodium sulfate, filtered, and concentrated. The residue is dissolved in THF (200 ml) at 0° C. and NaBH$_4$ (3.25 g, 85.9 mmol, 3.31 eq) in 25 ml of ice water is added within 10 min. The reaction is stirred for 1 h at 0° C. 100 ml of water and 300 ml of TBME are added, and the organic layer is separated, washed with aq bicarbonate and brine, dried over sodium sulfate, filtered, and concentrated. The product is used in the next step without further purification.

HPLC (Nucleosil C18HD, 4×70 mm, 3 μm, 20-100% MeCN (6 min), 100% MeCN (1.5 min)) retention time=3.76 min $^1$H-NMR (400 MHz, CDCl$_3$): 7.58 (s, 1H), 7.42 (s, 1H), 7.10 (s, 1H), 6.05-5.92 (m, 1H), 5.41-5.22 (m, 2H), 4.66 (s, 2H), 4.53 (d, 2H), 3.86 (s, 3H).

b) 3-Allyloxy-5-methoxymethyl-benzoic acid methyl ester

NaH (1.19 g, 29.8 mmol, 1.25 eq) is added to the solution of 3-allyloxy-5-hydroxymethyl-benzoic acid methyl ester (5.3 g, 23.8 mmol, 1 eq) in DMF (60 ml) at 0° C., and the reaction mixture is stirred for 30 min. After addition of methyl iodide (3.32 ml, 35.8 mmol, 1.5 eq) the reaction is stirred for 2 h at rt. 1N aq hydrochloric acid (20 ml) and TBME (200 ml) are added, the organic layer is separated, washed with brine, dried over sodium sulfate, filtered and concentrated. The product is used for the next step without further purification.

HPLC (Nucleosil C18HD, 4×70 mm, 3 μm, 20-100% MeCN (6 min), 100% MeCN (1.5 min)) retention time=4.99 min $^1$H-NMR (400 MHz, CDCl$_3$): 7.52 (s, 1H), 7.42 (s, 1H), 7.05 (s, 1H), 6.05-5.92 (m, 1H), 5.40-5.19 (m, 2H), 4.55 (d, 2H), 4.40 (s, 2H), 3.85 (s, 3H), 3.32 (s, 3H).

c) 3-(3-Hydroxy-propoxy)-5-methoxymethyl-benzoic acid methyl ester

9-BBN (0.5 N in THF, 48.7 ml, 24.4 mmol, 2.88 eq) is added to the solution of 3-allyloxy-5-methoxymethyl-benzoic acid methyl ester (2.00 g, 8.46 mmol, 1 eq) in THF (60 ml) at 0° C., and the reaction mixture is stirred for 20 h. After the addition of H$_2$O$_2$ (30% in water, 55 ml) and sodium carbonate (4% in water, 184 ml) the reaction is stirred for 1 h. TBME (250 ml) is added, the organic layer is separated, washed with brine, dried over sodium sulfate, filtered and concentrated. The product is purified by chromatography on silica (EtOAc/hexane 55/45).

MS (ES+): 272 [M+NH$_4$]$^+$

HPLC (Nucleosil C18HD, 4×70 mm, 3 µm, 20-100% MeCN (6 min), 100% MeCN (1.5 min)) retention time=3.38 min d) 3-(3-Methanesulfonyloxy-propoxy)-5-methoxymethyl-benzoic acid methyl ester Methansulfonyl chloride (170 µl, 2.2 mmol, 1.1 eq) and Et$_3$N (334 µl, 2.4 mmol, 1.2 eq) are added to the solution of 3-(3-hydroxy-propoxy)-5-methoxymethyl-benzoic acid methyl ester (508 mg, 2.00 mmol, 1 eq) in THF (10 ml) and the reaction is stirred for 22 h. Aqueous sodium bicarbonate (10 ml) and EtOAc (20 ml) are added, the organic layer is separated, washed with brine, dried over sodium sulfate, filtered and concentrated. The product is purified by chromatography on silica (EtOAc/hexane 1/1).

MS (ES+): 350 [M+NH$_4$]$^+$

HPLC (Nucleosil C18HD, 4×70 mm, 3 µm, 20-100% MeCN (6 min), 100% MeCN (1.5 min)) retention time=4.26 min

Building block A11: 2-Allyloxy-6-methoxymethyl-isonicotinic acid

2-Chloro-6-methoxymethyl-isonicotinic acid (building block A1b, 403 mg, 2 mmol, 1 eq) is dissolved in DMSO (3.4 ml) and allyl alcohol (1.7 ml). Sodium hydride (320 mg, 8 mmol, 4 eq) is added, and the suspension is heated to 100° C. for 3 h. The reaction mixture is cooled to rt and the pH is adjusted with 1N hydrochloric acid to pH=3. The mixture is concentrated, and the product is purified by chromatography on silica (DCM/MeOH 96/4).

MS (ES+): 224=[M+H]$^+$

HPLC (Nucleosil C18HD, 4×70 mm, 3 µm, 5-100% MeCN (6 min), 100% MeCN (1.5 min)) retention time=4.63 min

Building block A12: 3-Allyl-benzyloxycarbonyl-amino)-5-(2-oxo-propoxy)-benzoic acid The title compound is obtained following a published procedure (WO2006074950).

MS (ES+): 401 [M+NH$_4$]$^+$

HPLC (Nucleosil C18HD, 4×70 mm, 3 µm, 20-100% MeCN (6 min), 100% MeCN (1.5 min)) retention time=4.38 min

Building block A13: 3-(Allyl-benzyloxycarbonyl-amino)-5-[methyl-(propane-1-sulfonyl)-amino]-benzoic acid a) 3-Benzyloxycarbonylamino-5-nitro-benzoic acid

To the solution of 3-amino-5-nitrobenzoic acid (25 g, 135 mmol, 1 eq) in THF (150 ml) are added benzyl chloroformate (50% in toluene, 54 ml, 162 mmol, 1.2 eq) and aq sodium carbonate (150 ml). The reaction mixture is stirred for 90 min at rt and is then diluted with EtOAc and water. The organic layer is separated, washed with brine, dried over sodium sulfate, filtered and concentrated. The product is crystallized from diethyl ether and hexane.

MS (ES+): 334 [M+NH$_4$]$^+$

HPLC (Nucleosil C18HD, 4×70 mm, 3 µm, 20-100% MeCN (6 min), 100% MeCN (1.5 min)) retention time=2.67 min b) 3-(Allyl-benzyloxycarbonylamino)-5-nitro-benzoic acid allyl ester

To the solution of 3-benzyloxycarbonylamino-5-nitro-benzoic acid (34.5 g, 106 mmol, 1 eq) in DMF (500 ml) at 0° C. is added sodium hydride (7.6 g, 60%,190 mmol, 1.8 eq), followed by TBAI (3.91 g, 10.6 mmol, 0.1 eq) and allyl bromide (16.9 ml, 190 mmol, 1.8 eq). The reaction is stirred for 2 h at rt and then poured on ice cold 0.5 N aq hydrochloric acid. The mixture is extracted with diethyl ether. The combined organic layers are dried over sodium sulfate, filtered, and concentrated. The product is purified by chromatography on silica (EtOAc/hexane 1/4).

MS (ES−): 355 [M−H]$^-$

HPLC (Nucleosil C18HD, 4×70 mm, 3 µm, 20-100% MeCN (6 min), 100% MeCN (1.5 min)) retention time=4.49 min c) 3-(Allyl-benzyloxycarbonyl-amino)-5-amino-benzoic acid allyl ester

To the solution of 3-(allyl-benzyloxycarbonylamino)-5-nitro-benzoic acid allyl ester (8.8 g, 22.2 mmol, 1 eq) in EtOH (180 ml) is added SnCl$_2$*2H$_2$O (35.8 g, 155 mmol, 7 eq). The reaction is heated at 75° C. for 90 min and then cooled to rt. The mixture is acidified with 2N aq hydrochloric acid and diluted with EtOAc. The organic layer is washed with brine, dried over sodium sulfate, filtered and concentrated. The product is purified by chromatography on silica (hexane/EtOAc/NH$_3$ 70/30/0.2

MS (ES+): 367 [M+H]$^+$

HPLC (Nucleosil C18HD, 4×70 mm, 3 µm, 20-100% MeCN (6 min), 100% MeCN (1.5 min)) retention time=5.04 min d) 3-(Allyl-benzyloxycarbonyl-amino)-5-(propane-1-sulfonylamino)-benzoic acid allyl ester To the solution of 3-(allyl-benzyloxycarbonyl-amino)-5-amino-benzoic acid allyl ester (8.4 g, 20.8 mmol, 1 eq) in DCM (250 ml) are added pyridine (12 ml, 167 mmol, 8 eq) and propane sulfonyl chloride (13.1 g, 91.7 mmol, 4.4 eq). After stirring 4 h at rt the reaction mixture is diluted with 1 N aq hydrochloric acid and EtOAc. The organic layer is separated, dried over magnesium sulfate, filtered and concentrated. The product is purified by chromatography on silica (EtOAc/hexane 1/4).

MS (ES+): 490 [M+NH$_4$]$^+$

HPLC (Nucleosil C18HD, 4×70 mm, 3 µm, 20-100% MeCN (6 min), 100% MeCN (1.5 min)) retention time=5.67 min e) 3-(Allyl-benzyloxycarbonyl-amino)-5-[methyl-(propane-1-sulfonyl)-amino]-benzoic acid allyl ester To the solution of 3-(allyl-benzyloxycarbonyl-amino)-5-(propane-1-sulfonylamino)-benzoic acid allyl ester (1.00 g, 1.69 mmol, 1 eq) in acetonitrile (35 ml) are added potassium carbonate (520 mg, 3.72 mmol, 2.2 eq) and methyl iodide (234 µl, 3.72 mmol, 2.2 eq). After stirring 18 h at rt the reaction mixture is filtered and concentrated. The product is purified by chromatography on silica (EtOAc/hexane 1/4).

MS (ES+): 504 [M+NH$_4$]$^+$

HPLC (Nucleosil C18HD, 4×70 mm, 3 µm, 20-100% MeCN (6 min), 100% MeCN (1.5 min)) retention time=5.99 min f) 3-(Allyl-benzyloxycarbonyl-amino)-5-[methyl-(propane-1-sulfonyl)-amino]-benzoic acid The solution of 3-(allyl-benzyloxycarbonylamino)-5-[methyl-(propane-1-sulfonyl)-amino]-benzoic acid allyl ester (550 mg, 0.90 mmol, 1 eq) in MeOH (15 ml) and 4 N aq sodium hydroxide (0.9 ml, 3.62 mmol, 4 eq) is stirred for 3 h at rt. The reaction mixture is diluted with EtOAc and 2N aq hydrochloric acid. The organic layer is separated, washed with brine, dried over sodium sulfate, filtered and concentrated to give the product.

MS (ES−): 445 [M−H]$^-$

HPLC (Nucleosil C18HD, 4×70 mm, 3 µm, 20-100% MeCN 6 min), 100% MeCN (1.5 min)) retention time=4.84 min Building block A14: 3-(Allyl-benzyloxycarbonyl-amino)-5-methoxy-benzoic acid a) 3-Allyl-benzyloxycarbonyl-amino)-5-methoxy-benzoic acid methyl ester To a solution of 4.18 g (12 mmol) 3-(allyl-benzyloxycarbonyl-amino)-5-methoxy-benzoic acid methyl ester [obtained following a published procedure (WO2006074950)] in 18 ml DMF are added 2.51 g (18 mmol) powdered potassium carbonate. To this mixture are added 978 µl (15.6 mmol) iodomethane at 0° C. The mixture is allowed to warm to rt and stirred for 16 h. The reaction mixture is diluted with 60 ml water and extracted with toluene. The combined organic layers are washed with water, dried over sodium sulfate and evaporated to give the product as colorless oil.

Rf (acetone/cyclohexane=50/50): 0.63.

MS (ES+): 356=[M+H]$^+$.

$^1$H-NMR (400 MHz, DMSO-d$_6$): 7.44 (s, 1H), 7.36-7.27 (m, 6H), 7.17 (t, 1H), 5.91-5.81 (m, 1H), 5.14-5.09 (m, 4H), 4.30 (d, 2H), 3.84 (s, 3H), 3.79 (s, 3H).

b) 3-(Allyl-benzyloxycarbonyl-amino)-5-methoxy-benzoic acid

To a solution of 4.09 g (11.5 mmol) 3-(allyl-benzyloxycarbonyl-amino)-5-methoxy-benzoic acid methyl ester in 27.6 ml THF/MeOH (50/50) are added at 0° C. 13.8 ml (13.8 mmol) 1M aq sodium hydroxide. The mixture is allowed to warm to rt and stirred for 16 h. The reaction mixture is acidified to pH 3 by addition of 10 ml 1M aq hydrochloric acid. The organic solvents are evaporated and the aqueous solution is extracted with DCM. The combined organic layers are washed with half saturated brine, dried over sodium sulfate and evaporated to give the product as yellowish solid.

m.p. 98-99° C.

Rf (DCM/MeOH/NH$_3$=95/4.5/0.5): 0.30.

MS (ES+): 342.1=[M+H]$^+$.

$^1$H-NMR (400 MHz, DMSO-d$_6$): 13.10 (br s, 1H), 7.42 (t, 1H), 7.35-7.26 (m, 6H), 7.12 (t, 1H), 5.91-5.81 (m, 1H), 5.14-5.09 (m, 4H), 4.29 (d, 2H), 3.77 (s, 3H).

Building block A15: 5-(Allyl-benzyloxycarbonyl-amino)-N,N-dimethyl-isophthalamic acid a) 5-Benzyloxycarbonylamino-N,N-dimethyl-isophthalamic acid methyl ester A solution of 5-benzyloxycarbonylamino-isophthalic acid monomethyl ester (3.29 g, 10 mmol) [obtained according to literature procedure as described in WO2006074950] in thionylchloride (10 ml, 140 mmol) is heated at reflux temperature for 1 h. Excess thionylchloride is evaporated and the residue dissolved in 20 ml DCM. At 0° C. a solution of dimethylamine in THF (1.36 g, 30 mmol) is added and the mixture is stirred at rt for 1 h. The reaction mixture is diluted with 80 ml DCM and 100 ml half-saturated aq ammonium chloride. The layers are separated, the aqueous phase is extracted with DCM, the combined organic layers are washed with water, dried over sodium sulfate and evaporated. The residue is purified by chromatography on silica gel (cyclohexane/EtOAc 80/20 to EtOAc) to the product as off-white solid m.p.: 155-158° C.

Rf (EtOAc/acetone=80/20): 0.59.

MS (ES+): 357=[M+H]$^+$.

$^1$H-NMR (400 MHz, DMSO-d$_6$): 10.13 (s, 1H), 8.16 (s, 1H), 7.69 (t, 1H), 7.52 (t, 1H), 7.42-7.30 (m, 5H), 5.16 (s, 2H), 3.84 (s, 3H), 2.97 (s, 3H), 2.86 (s, 3H).

b) 5-(Allyl-benzyloxycarbonyl-amino)-N,N-dimethyl-isophthalamic acid methyl ester To a solution of 5-benzyloxycarbonylamino-N,N-dimethyl-isophthalamic acid methyl ester (803 mg, 2.25 mmol) in 4.5 ml DMF at 0° C. are added sodium hydride (177 mg, 4.06 mmol, 60% in mineral oil) and allylbromide (289 µl, 3.38 mmol) and the mixture is stirred at rt for 4 h. The reaction mixture is diluted with 45 ml toluene and 45 ml saturated ammonium chloride solution. The layers are separated, the aqueous phase is extracted with toluene, the combined organic layers are washed with water, dried over sodium sulfate and evaporated. The residue is purified by chromatography on silica gel (cyclohexane/EtOAc 90/10 to 50/50) which gives the product as colorless resin.

Rf (cyclohexane/EtOAc=20/80): 0.39.

MS (ES+): 397=[M+H]$^+$.

$^1$H-NMR (400 MHz, DMSO-d$_6$): 7.89 (s, 1H), 7.73 (t, 1H), 7.59 (t, 1H), 7.34-7.26 (m, 5H), 5.91-5.81 (m, 1H), 5.12-5.08 (m, 4H), 4.33 (d, 2H), 3.85 (s, 3H), 2.96 (s, 3H), 2.80 (s, 3H).

c) 5-(Allyl-benzyloxycarbonyl-amino)-N,N-dimethyl-isophthalamic acid

To a solution of 5-(allyl-benzyloxycarbonyl-amino)-N,N-dimethyl-isophthalamic acid methyl ester (712 mg, 1.8 mmol) in 7.2 ml THF/MeOH (50/50) are added at 0° C. 3.6 ml 1M sodium hydroxide. The solution is allowed to warm to rt and is stirred for 3 h. The reaction mixture is acidified to pH 3 by addition of 6 ml 0.5M aq hydrochloric acid and the organic solvents are evaporated. The aqueous solution is extracted with DCM, the combined organic layers are washed with water, dried over sodium sulfate and evaporated to give a colorless foam.

Rf (DCM/MeOH/NH$_3$=90/9/1): 0.12.
MS (ES+): 405=[M+Na]$^+$.
$^1$H-NMR (400 MHz, DMSO-d$_6$): 13.27 (br s, 1H), 7.86 (t, 1H), 7.72 (t, 1H), 7.55 (t, 1H), 7.33-7.26 (m, 5H), 5.91-5.81 (m, 1H), 5.13-5.08 (m, 4H), 4.32 (d, 2H), 2.96 (s, 3H), 2.81 (s, 3H).

Building block A16:
2-(Acetyl-allyl-amino)-6-chloro-isonicotinic acid a) 2-Acetylamino-6-chloro-isonicotinic acid ethyl ester A mixture of 14 g 2-amino-6-chloro-isonicotinic acid ethyl ester (Temple et al. J. Heterocycl. Chem. 1970, 7, 451) (70 mmol) in 150 ml acetic anhydride (large excess) and 150 ml pyridine (large excess) is stirred at 60° C. in the presence of 244 mg (2 mmol) DMAP for 16 h. The mixture is concentrated in vacuo, taken up in EtOAc and washed with 1N HCl, brine and 10% aq Na$_2$CO$_3$ to yield the title compound in the form of yellowish crystals (EtOH).

Rf: (hexane/EtOAc=2/1): 0.46
HPLC (Nucleosil C-18HD, 4×70 mm, 3 μm, 40-100% MeCN (6 min), 100% MeCN (1.5 min)): 3.619 min
MS(ES) [M+H]$^+$=243, 245
$^1$H-NMR (400 MHz, CDCl$_3$): 8-65 (s, 1H), 7.97 (br s, 2H), 7.65 (s, 1H), 4.45 (q, 2H), 2.26 (s, 3H), 1.44 (t, 3H).

b) 2-(Acetyl-allyl-amino)-6-chloro-isonicotinic acid ethyl ester

A mixture of 6.0 g (25 mmol) 2-acetylamino-6-chloro-isonicotinic acid ethyl ester, 10.36 g (75 mmol) potassium carbonate and 4.23 ml (50 mmol) allyl bromide in 25 ml DMF is stirred at 60° C. for 24 h. The cooled mixture is diluted with water and TBME. The organic phase is washed with water, dried over Na$_2$SO$_4$ and evaporated. The product is purified by chromatography on silica gel (hexane/EtOAc 9/1) to yield the title compound as a yellowish oil.

Rf: (hexane/EtOAc=2/1): 0.46
HPLC (Nucleosil C-18HD, 4×70 mm, 3 μm, 40-100% MeCN (6 min), 100% MeCN (1.5 min)): 3.619 min
MS(ES) [M+H]$^+$=283, 285; [MNa]$^+$=305, 307.
$^1$H-NMR (400 MHz, CDCl$_3$): 7.96 (br s, 1H), 7.74 (s, 1H), 5.98-5.88 (m, 1H), 5.22-5.17 (m, 2H), 4.59 (d, 2H), 4.45 (q, 2H), 2.26 (s, 3H), 1.44 (t, 3H).

c) 2-(Acetyl-allyl-amino)-6-chloro-isonicotinic acid

A solution of 1.08 g 2-(acetyl-allyl-amino)-6-chloro-isonicotinic acid ethyl ester (3.82 mmol) in 15 ml MeOH is treated with 5.5 ml 1N NaOH (5.5 mmol) and stirred at 25° C. for 30 min. The reaction is quenched with 6 ml 1 N HCl and with EtOAc extracted. Crystallization from a small amount of EtOAc gives the title compound as yellow crystals.

Rf: (EtOAc/2% AcOH): 0.60
HPLC (Nucleosil C-18HD, 4×70 mm, 3 μm, 20-100% MeCN (6 min), 100% MeCN (1.5 min)): 3.475 min
MS(ES) [M+H]$^+$=255, 257; [M+Na]$^+$=277, 279

$^1$H-NMR (400 MHz, CDCl$_3$): 8.04 (br s, 1H), 7.79 (s, 1H), 6.00-5.92 (m, 1H), 5.26-5.19 (m, 2H), 4.60 (d, 2H), 2.32 (s, 3H).

Building block A17:
2-(Acetyl-allyl-amino)-6-methyl-isonicotinic acid a) 2-(N'-Isopropylidene-hydrazino)-6-methyl-isonicotinic acid ethyl ester A mixture of 7.35 g 42.86 mmol) 2-chloro-6-methyl-isonicotinic acid, 10.75 g (250 mmol) hydrazine hydrate and 10.7 ml 4N NaOH is stirred at 125° C. for 24 h. The mixture is evaporated to dryness, taken up in 35 ml water, 35 ml ethanol and 50 ml acetone and stirred for 1 h. The mixture is concentrated once more and refluxed in a solution of 20 ml thionyl chloride in 200 ml ethanol. After 1.5 h the mixture is cooled down and filtered. The filtrate is diluted with ethyl acetate and washed with 10% aq NaHCO$_3$ solution. The aquous phase is extracted with EtOAc/acetone (4:1) three times. The combined organic layers are dried over sodium sulfate and chromatographed on silica gel ((EtOAc/hexanes=1:2) to give a brownish oil, which crystallizes from EtOH/water. M.p. 79-82° C.

Rf: (EtOAc/hexanes)=1/1): 0.27
HPLC (Nucleosil C-18HD, 4×70 mm, 3 μm, 5-100% MeCN (6 min), 100% MeCN (1.5 min)): 3.617 min
MS (ES+): 236=[M+H]$^+$
$^1$H-NMR (400 MHz, CDCl$_3$): 8.05 (br, 1H), 7.59 (s, 1H), 7.14 (s, 1H), 4.39 (q, 2H), 2.46 (s, 3H), 2.07 (s, 3H), 1.93 (s, 3H), 1.41 (t, 3H).

b) 2-Amino-6-methyl-isonicotinic acid ethyl ester

A solution of 8.37 g (35.6 mmol) 2-(N'-isopropylidene-hydrazino)-6-methyl-isonicotinic acid ethyl ester in 150 ml EtOH is hydrogenated for 11 h at 80° C. and 6 bar hydrogen in the presence of 25 g Raney-Ni. After cooling down the mixture is filtered over celite and evaporated. The product is crystallized from EtOH/water to give white crystals.

Rf: (EtOAc/hexanes)=1/1): 0.29
HPLC (Nucleosil C-18HD, 4×70 mm, 3 μm, 20-100% MeCN (6 min), 100% MeCN (1.5 min)): 1.355 min
MS (ES+): 181=[M+H]$^+$
$^1$H-NMR (400 MHz, CDCl$_3$): 7.08 (s, 1H), 6.93 (s, 1H), 4.61 (br, 2H), 4.19 (q, 2H), 2.46 (s, 3H), 1.41 (t, 3H).

c) 2-(Acetyl-allyl-amino)-6-methyl-isonicotinic acid

The title compound is prepared similarly to building block A16, starting from 2-amino-4-methyl-isonicotinic acid ethyl ester. The crude product is crystallized from EtOAc/hexanes to obtain a white powder.

HPLC (Zorbax SB-C18H, 3×30 mm, 1.8 μm, 10-100% MeCN (3.25 min), 100% MeCN (0.75 min), 100-10% MeCN (0.25 min)): 2.354 min
MS (ES+): 235=[M+H]$^+$
$^1$H-NMR (400 MHz, d6-DMSO): 7.73 (s, 1H), 7.59 (s, 1H), 5.93-5.82 (m, 1H), 5.16-5.07 (m, 2H), 4.52-4.46 (m, 2H), 2.53 (s, 3H), 2.07 (s, 3H).

Building block A18:
2-Allylamino-6-methoxy-isonicotinic acid

A mixture of 3.97 ml (52 mmol, 10 eq) allylamine, 0.97 g (5.2 mmol, 1 eq) 2-chloro-6-methoxy-isonicotinic acid (see building block A3) and 1.29 g (5.2 mmol, 1 eq)-copper(II)

sulfate pentahydrate in 10 ml water is heated in a closed vessel during 2.5 h at a bath temperature of 160° C. After cooling to rt the mixture is diluted with 400 ml aq 10% citric acid and extracted with EtOAc. The extracts are washed with water and brine, dried over sodium sulfate and the solvents are evaporated at reduced pressure. The residue is dissolved in about 20 ml hot DCM/MeOH (2/1). On addition of about 25 ml of hexane, partial evaporation of the solvents to a volume of about 20 ml and keeping at 4° C. for 4 h the product precipitates and is filtered off and dried in vacuum.

MS (LC/MS): 209=[M+H]$^+$ $^1$H-NMR (400 M Hz, DMSO-d$_6$): 7.04 (t, 1H), 6.55 (s, 1H), 6.26 (s, 1H), 5.97-5.88 (m, 1H), 5.21 (d, 1H), 5.09 (d, 1H), 3.92 (d, 2H), 3.80 (s, 3H).

Building block A19: 3-(Allyl-benzyloxycarbonyl-amino)-5-(2-oxo-pyrrolidin-1-yl)-benzoic acid a) 3-Benzyloxycarbonylamino-5-(2-oxo-pyrrolidin-1-yl)-benzoic acid methyl ester To a stirred mixture of 3.74 g (16.0 mmol) 3-amino-5-(2-oxo-pyrrolidin-1-yl)-benzoic acid methyl ester and 4.02 g (48 mmol) sodium bicarbonate in 15 ml MeCN is added dropwise 8.0 ml (23.9 mmol) benzyl chloroformate (50% in toluene). After 18 h the mixture is diluted with water and DCM. A part of the sparingly soluble product is filtered off. The organic layer is dried over sodium sulfate and evaporated. The crude product is crystallized from chloroform/MeOH/DMF/hexanes to yield a grey solid.

Rf: (EtOAc/hexane 2:1): 0.60

HPLC (Zorbax SB-C18, 3×30 mm, 1.8 μm, 10-100% MeCN (3.25 min), 100% MeCN (0.75 min)): 3.389 min

MS (ES+): 369=[M+H]$^+$ $^1$H-NMR (400 MHz, DMSO-d$_6$): 10.12 (s, NH), 8.01 (s, 1H), 7.97 (s, 1H), 7.95 (s, 1H), 5.19 (s, 2H), 3.85 (s, 3H), 3.82 (t, 2H), 2.14-2.05 (m, 2H)

b) 3-(Allyl-benzyloxycarbonyl-amino)-5-(2-oxo-pyrrolidin-1-yl)-benzoic acid methyl ester A suspension of 3.69 g (8.1 mmol) 3-benzyloxycarbonylamino-5-(2-oxo-pyrrolidin-1-yl)-benzoic acid methyl ester, 1.37 ml (16.2 mmol) allyl bromide, 2.24 g (16.2 mmol) potassium carbonate in 8 ml DMF is stirred at 50° C. for 4 h. The mixture is diluted with water and extracted with EtOAc. The organic phase is washed with water and dried over sodium sulfate. The product is purified by chromatography on silica gel (EtOAc/hexanes 1:4, 1:2, 1:1, 2:1). The title compound is isolated as a yellow resin.

Rf: (EtOAc/hexane 2:1): 0.62

HPLC (Zorbax SB-C18, 3×30 mm, 1.8 μm, 30-100% MeCN (3.25 min), 100% MeCN (0.75 min)): 3.062 min

MS (ES+): 409=[M+H]$^+$ $^1$H-NMR (400 MHz, CDCl$_3$): 8.09 (br s, 1H), 7.96 (s, 1H), 7.75 (s, 1H), 7.40-7.29 (m, 5H), 6.00-5.88 (m, 1H), 5.23-5.17 (m, 2H), 4.37-4.34 (m, 2H), 3.95 (s, 3H), 3.86 (t, 2H), 2.65 (t, 2H), 2.24-2.17 (m, 2H).

c) 3-(Allyl-benzyloxycarbonyl-amino)-5-(2-oxo-pyrrolidin-1-yl)-benzoic acid

A solution of 1.56 g (3.82 mmol) 3-(allyl-benzyloxycarbonyl-amino)-5-(2-oxo-pyrrolidin-1-yl)-benzoic acid methyl ester in 25 ml MeOH is treated with 8 ml 1N aq sodium hydroxide. After 3 h the homogeneous mixture is acidified with 1N aq hydrochloric acid and extracted with EtOAc. The organic phase is washed with water, dried over sodium sulfate and evaporated to give a yellowish foam.

HPLC (Zorbax SB-C18, 3×30 mm, 1.8 μm, 30-100% MeCN (3.25 min), 100% MeCN (0.75 min)): 2.475 min

MS (ES+): 395=[M+H]$^+$ $^1$H-NMR (400 MHz, CDCl$_3$): 8.17 (s, 1H), 8.00 (s, 1H), 7.82 (s, 1H), 7.40-7.31 (m, 5H), 6.01-5.90 (m, 1H), 5.25-5.18 (m, 2H), 5.21 (s, 2H), 4.39-4.35 (m, 2H), 3.88 (t, 2H), 2.68 (t, 2H), 2.26-2.18 (m, 2H).

Building block A20: 3-(Allyl-benzyloxycarbonyl-amino)-5-thiazol-2-yl-benzoic acid a) 3-Benzyloxycarbonylamino-5-iodo-benzoic acid methyl ester To a stirred suspension of 4.66 g (16.8 mmol) 3-amino-5-iodo-benzoic acid methyl ester (J. Med. Chem. 1973, 16, 684) in 16 ml DCM and 16 ml 10% aq sodium bicarbonate are added drop wise 8.4 ml benzyl chloroformate (50% solution in toluene). After 3 h the phases are separated, the organic phase is dried over sodium sulfate and the solvent is evaporated. The product is crystallized from EtOAc/hexanes.

Rf: (hexane/EtOAc 3:1): 0.30

HPLC (Zorbax SB-C18, 3×30 mm, 1.8 μm, 30-100% MeCN (3.25 min), 100% MeCN (0.75 min)): 3.580 min MS (ES+): 434=[M+Na]$^+$ $^1$H-NMR (400 MHz, CDCl$_3$): 8.20 (s, 1H), 8.10 (s, 1H), 7.93 (s, 1H), 7.47-7.38 (m, 5H), 6.80 (br s, NH), 5.25 (s, 2H), 3.94 (s, 3H).

b) 3-Benzyloxycarbonylamino-5-thiazol-2-yl-benzoic acid methyl ester

A mixture of 1 g (2.4 mmol) 3-allyl-benzyloxycarbonyl-amino)-5-thiazol-2-yl-benzoic acid methyl ester, 1 g (2.67 mmol) 2-tributylstannylthiazole, 84 mg (0.12 mmol) PdCl$_2$(PPh$_3$)$_2$ and 20 mg CuI in 10 ml dioxane is refluxed until the reaction has stopped (according to TLC analysis). The mixture is diluted with MeCN and washed twice with hexane. The polar phase is concentrated and stirred vigorously with a solution of 1 g potassium fluoride in 10 ml water. The mixture is filtered over high-flow and then heated at 60° C. in the presence of 2 g sodium dithionite and 2 g charcoal. The mixture is again filtered over high-flow and further purified by chromatography on silica gel (hexane/EtOAc 8:1, 6:1, 4:1, 2:1, 1:2) to give a yellow solid.

Rf: (hexane/EtOAc 3:1): 0.18

HPLC (Zorbax SB-C18, 3×30 mm, 1.8 μm, 30-100% MeCN (3.25 min), 100% MeCN (0.75 min)): 3.254 min

MS (ES+): 369=[M+H]$^+$ $^1$H-NMR (400 MHz, CDCl$_3$): 8.36 (s, 1H), 8.35 (s, 1H), 8.18 (s, 1H), 7.94 (d, 1H), 7.49-7.40 (m, 6H), 6.95 (br s, NH), 5.28 (s, 2H), 3.98 (s, 3H).

c) 3-(Allyl-benzyloxycarbonyl-amino)-5-thiazol-2-yl-benzoic acid methyl ester

A suspension of 257 mg (0.6981 mmol) 3-benzyloxycarbonylamino-5-thiazol-2-yl-benzoic acid methyl ester, 0.12 ml (1.4 mmol) allyl bromide, and 193 mg (1.4 mmol) potassium carbonate in 4 ml DMF is stirred 4 h. The mixture is diluted with water and extracted with EtOAc. The organic phase is washed with water and dried over sodium sulfate. The product is purified by chromatography on silica gel (EtOAc/hexanes 1:6, 1:4, 1:2, 1:1) to give a resin.

Rf: (hexane/EtOAc 1:1): 0.41
HPLC (Zorbax SB-C18, 3×30 mm, 1.8 µm, 30-100% MeCN (3.25 min), 100% MeCN (0.75 min)): 2.499 min
MS (ES+): 409=[M+H]$^+$
$^1$H-NMR (400 MHz, CDCl$_3$): 8.47 (s, 1H), 8.17 (br s, 1H), 8.02 (br s, 1H), 7.93 (d, 1H), 7.43 (d, 1H), 7.39-7.30 (m, 5H), 6.01-5.91 (m, 1H), 5.23 (s, 2H), 5.24-5.19 (m2H), 4.42-4.39 (m, 2H), 3.99 (s, 3H).

d) 3-(Allyl-benzyloxycarbonyl-amino)-5-thiazol-2-yl-benzoic acid

A solution of 181 mg (0.444 mmol) 3-(allyl-benzyloxycarbonyl-amino)-5-thiazol-2-yl-benzoic acid methyl ester in 1 ml MeOH is treated with 1 ml 1N aq sodium hydroxide. After 18 h the mixture is acidified with 1N aq hydrochloric acid to pH 2-3 and extracted with EtOAc. The organic phase is washed with water, dried over sodium sulfate and evaporated to give a yellow resin.
HPLC (Zorbax SB-C18, 3×30 mm, 1.8 µm, 30-100% MeCN (3.25 min), 100% MeCN (0.75 min)): 2.916 min
MS (ES+): 395=[M+H]$^+$
$^1$H-NMR (400 MHz, CDCl$_3$): 8.62 (s, 1H), 8.20 (br s, 1H), 8.10 (s, 1H), 8.00 (d, 1H), 7.47 (d, 1H), 7.40-7.31 (m, 5H), 6.04-5.92 (m, 1H), 5.25-5.20 (m, 2H), 5.24 (s, 2H), 4.40-4.40 (m, 2H).

Building block A21: 3-(Allyl-benzyloxycarbonyl-amino)-5-[1,3]dioxolan-2-yl-benzoic acid a) 3-Nitro-5-(tetrahydro-pyran-2-yloxymethyl)-benzoic acid methyl ester

To a solution of 5.0 g (23.68 mmol) of 3-hydroxymethyl-5-nitro-benzoic acid methyl ester in 50 ml of DCM is added 2.38 ml (26.0 mmol) of 3,4-dihydro-2H-pyran and 299 mg (1.28 mmol) (±)-camphor-10-sulfonic acid and the mixture is stirred for 1 h. After the reaction is completed the mixture is washed with 5% aq sodium bicarbonate, dried over sodium sulfate, and chromatographed on silica gel (hexane/EtOAc 3:1) to give a white solid.
Rf: (hexane/EtOAc 3:1): 0.41
HPLC (Nucleosil C-18HD, 4×70 mm, 3 µm, 20-100% MeCN (6 min), 100% MeCN (1.5 min)): 5.408 min
MS (ES+): 318=[M+Na]$^+$
$^1$H-NMR (400 MHz, CDCl$_3$): 8.80 (s, 1H), 8.48 (s, 1H), 8.39 (s, 1H), 4.97 (d, 1H, J=15), 4.81-4.79 (m, 1H), 4.67 (d, 1H, J=15), 4.02 (s, 3H), 3.98-3.89 (m, 1H), 3.65-3.59 (m, 1H), 1.99-1.58 (m, 6H).

b) 3-Amino-5-(tetrahydro-pyran-2-yloxymethyl)-benzoic acid methyl ester

A solution of 6.61 g (22.38 mmol) 3-nitro-5-(tetrahydro-pyran-2-yloxymethyl)-benzoic acid methyl ester is hydrogenated in THF in the presence of 0.66 g 5% PVC (Engelhard 4709) for 5 h. The mixture is filtered over high-flow and concentrated to yield a yellow that is used for the next step without further purification.
Rf: (EtOAc/hexane 1/3): 0.12
HPLC (Nucleosil C-18HD, 4×70 mm, 3 µm, 20-100% MeCN (6 min), 100% MeCN (1.5 min)): 3.012 min
MS (ES+): 266=[M+H]$^+$ c) 3-Benzyloxycarbonylamino-5-(tetrahydro-pyran-2-yloxymethyl)-benzoic acid methyl ester To a stirred mixture of 5.93 g (22.35 mmol) of 3-amino-5-(tetrahydro-pyran-2-yloxymethyl)-benzoic acid methyl ester and 30 ml 10% aq sodium bicarbonate in 30 ml THF are added dropwise 8.96 ml of benzyl chloroformate (50% in toluene). After 2 h the mixture is extracted with EtOAc. The organic phase is washed with water, dried over sodium sulfate and the product is crystallized from EtOAc/hexane to give white crystals.
Rf: (EtOAc/hexane 1/2): 0.47
HPLC (Nucleosil C-18HD, 4×70 mm, 3 µm, 20-100% MeCN (6 min), 100% MeCN (1.5 min)): 5.758 min
MS (ES+): 422=[M+N]$^+$
$^1$H-NMR (400 MHz, CDCl$_3$): 7.99 (s, 1H), 7.79 (s, 11H), 7.72 (s, 1H), 7.48-7.36 (m, 5H), 6.81 (br s, NH), 5.25 (s, 2H), 4.84 (d, 1H, J=15), 4.76-4.73 (m, 1H), 4.54 (d, 1H, J=15), 3.99-3.90 (m, 1H), 3.94 (s, 3H), 3.62-3.53 (m, 1H), 1.95-1.58 (m, 6H).

d) 3-Benzyloxycarbonylamino-5-hydroxymethyl-benzoic acid methyl ester

A suspension of 4 g (10 mmol) 3-benzyloxycarbonylamino-5-(tetrahydro-pyran-2-yloxymethyl)-benzoic acid methyl ester and 200 mg (0.86 mmol) (±)-camphor-10-sulfonic acid in 50 ml MeOH and 5 ml THF is stirred for 18 h. The homogeneous solution is quenched with 10% aq sodium bicarbonate and extracted with EtOAc. The organic phase is washed with brine, dried over sodium sulfate, and concentrated to give a white crystalline solid.
Rf: (EtOAc/hexane 1/2): 0.16
HPLC (Zorbax SB-C18, 3×30 mm, 1.8 µm, 30-100% MeCN (3.25 min), 100% MeCN (0.75 min)): 2.315 min
MS (ES+): 298=[M−OH]$^+$; 338=[M+Na]$^+$
$^1$H-NMR (400 MHz, CDCl$_3$): 7.94 (s, 1H), 7.79 (s, 1H), 7.77 (s, 1H), 7.47-7.36 (m, 5H), 7.05 (br s, NH), 5.24 (s, 2H), 4.75 (s, 2H), 3.92 (s, 3H).

e) 3-Benzyloxycarbonylamino-5-formyl-benzoic acid methyl ester

A suspension of 3.16 g (10 mmol) 3-benzyloxycarbonylamino-5-hydroxymethyl-benzoic acid methyl ester and 8.71 g (100 mmol) manganese(IV) oxide is stirred at 55° C. for 3 h. After cooling the mixture is filtered over high-flow and evaporated to provide a crystalline solid that is used for the next step without further purification.
Rf: (EtOAc/hexane 1/2): 0.47
HPLC (Zorbax SB-C18, 3×30 mm, 1.8 µm, 30-100% MeCN (3.25 min), 100% MeCN (0.75 min)): 2.950 min
MS (ES+): 298=[M−H]$^+$; 338=[M+Na]$^+$
$^1$H-NMR (400 MHz, CDCl$_3$): 10.09 (s, 1H), 8.32 (s, 1H), 8.27 (s, 1H), 8.27 (s, 1H), 7.77 (s, 1H), 7.48-7.39 (m, 5H), 7.05 (br s, NH), 5.28 (s, 2H), 3.98 (s, 3H).

f) 3-Benzyloxycarbonylamino-5-[1,3]dioxolan-2-yl-benzoic acid methyl ester

A solution of 2.72 g (8.68 mmol) 3-benzyloxycarbonylamino-5-formyl-benzoic acid methyl ester and 0.58 ml ethylene glycol in 40 ml toluene and 40 ml cyclolhexane is heated at reflux temperature in the presence of 54 mg (±)-camphor-10-sulfonic acid under continuous removal of water. After the reaction is completed the mixture is diluted with TBME and washed with 10% aq sodium bicarbonate. The organic phase is washed with water, dried over sodium sulfate and evaporated. The product is used for the next step without further purification.

HPLC (Nucleosil C-18HD, 4×70 mm, 3 µm, 20-100% MeCN (6 min), 100% MeCN (1.5 min)): 5.040 min

MS (ES+): 358=[M+H]$^+$ $^1$H-NMR (400 MHz, CDCl$_3$): 8.05 (s, 1H), 7.88 (s, 1H), 7.86 (s, 1H), 7.48-7.38 (m, 5H), 6.94 (br s, NH), 5.87 (s, 1H), 5.25 (s, 2H), 4.19-4.05 (m, 4H), 3.93 (s, 3H).

g) 3-(Allyl-benzyloxycarbonyl-amino)-5-[1,3]dioxolan-2-yl-benzoic acid methyl ester A suspension of 3.25 g (9.09 mmol) 3-benzyloxycarbonylamino-5-[1,3]dioxolan-2-yl-benzoic acid methyl ester, 1.54 ml (18.19 mmol) allyl bromide and 2.51 g (18.19 mmol) potassium carbonate in 7 ml DMF is stirred at 50° C. for 4 h. The mixture is diluted with water and extracted with EtOAc. The organic phase is washed three times with water and dried dried over sodium sulfate. The product is purified by chromatography on silica gel (EtOAc/hexanes 1:3, 1:2, 1:1) to give a yellow oil.

Rf: (EtOAc/hexane 1/3): 0.24

HPLC (Zorbax SB-C18, 3×30 mm, 1.8 µm, 30-100% MeCN (3.25 min), 100% MeCN (0.75 min)): 2.950 min MS (ES+): 298=[M−OH]$^+$; 338=[M+Na]$^+$ $^1$H-NMR (400 MHz, CDCl$_3$): 10.09 (s, 1H), 8.32 (s, 1H), 8.27 (s, 1H), 8.27 (s, 1H), 7.77 (s, 1H), 7.48-7.39 (m, 5H), 7.05 (br s, NH), 5.28 (s, 2H), 3.98 (s, 3H).

h) 3-(Allyl-benzyloxycarbonyl-amino)-5-[1,3]dioxolan-2-yl-benzoic acid

A solution of 3.22 g (8.1 mmol) 3-(allyl-benzyloxycarbonyl-amino)-5-[1,3]dioxolan-2-yl-benzoic acid methyl ester in 15 ml MeOH is treated with 20 ml 1N aq sodium hydroxide. After some time the reaction mixture becomes homogeneous. After 2 h the mixture is acidified with 1N HCl and extracted with EtOAc. The organic phase is washed with water, dried over sodium sulfate and evaporated to give a yellowish oil.

HPLC (Zorbax SB-C18, 3×30 mm, 1.8 µm, 30-100% MeCN (3.25 min), 100% MeCN (0.75 min)): 2.674 min

MS (ES+): 384=[M+H]$^+$ $^1$H-NMR (400 MHz, CDCl$_3$): 8.13 (s, 1H), 8.02 (s, 1H), 7.66 (s, 1H), 7.40-7.31 (m, 5H), 6.01-5.89 (m, 1H), 5.89 (s, 1H), 5.27-5.18 (m, 2H), 5.22 (s, 2H), 4.40-4.34 (m, 2H), 4.20-4.05 (m, 4H).

Building block A22: 3-Allyloxy-5-(2-oxo-pyrrolidin-1-yl)-benzoic acid a) 3-Bromo-5-nitro-benzoic acid

To the solution of 7.92 g (43 mmol) 3-amino-5-nitro-benzoic acid in 4 ml water in an ice bath 48.8 ml (434 mmol, 10 eq) of aq 48% HBr are added. A saturated aqueous solution of 4.05 g (59 mmol, 1.35 eq) sodium nitrit is added over 10 min. The obtained solution is added to the solution of 9.36 g (65 mmol, 1.5 eq) cupper bromide in 48.8 ml (434 mmol, 10 eq) of aq 48% HBr at 70° C. The mixture is heated for 45 min at 70° C. After cooling to rt diethylether is added and the organic layer is washed with water until neutral pH is reached. Drying over sodium sulfate and evaporation of the solvent at reduced pressure to give the product as yellow solid.

MS (ES−): 245/247=[M+H]$^+$ $^1$H-NMR (400 MHz, d6-DMSO): 8.65 (s, 1H), 8.57 (s, 1H), 8.44 (s, 1H).

b) 3-Nitro-5-(2-oxo-pyrrolidin-1-yl)-benzoic acid

The mixture of 3.37 g (13.7 mmol) 3-bromo-5-nitro-benzoic acid, 1.74 g (27.4 mmol, 2 eq) cuper powder, 3.18 ml (41 mmol, 3 eq) 2-pyrrolidinone and 1.89 g (13.7 mmol, 1 eq) potassium carbonate is stirred at 150° C. for 16 h. Another 10 ml 2-pyrrolidinone, 1.74 g (27.4 mmol, 2 eq) copper powder and 1.89 g (13.7 mmol, 1 eq) potassium carbonate are added and the mixture is again stirred vigorously for 5.5 h at 150° C. After cooling to rt the reaction is diluted with DCM and 5% aq potassium carbonate. Solids are filtered off and the aqueous layer is acidified with 10% aq potassium hydrogensulfate solution. Extraction with DCM, drying over sodium sulfate, and evaporation of the solvent at reduced pressure gives some product. On standing more product precipitates from the aqueous layer, is filtered off and dried in vacuum.

MS (LC/MS): 273=[M+H+Na]$^+$ $^1$H-NMR (400 MHz, d6-DMSO): 8.83 (s, 1H), 8.52 (s, 1H), 8.37 (s, 1H). 3.98 (t, 2H), 2.60 (t, 2H), 2.16-2.08 (m, 2H).

c) 3-Amino-5-(2-oxo-pyrrolidin-1-yl)-benzoic acid

To the solution of 2.19 g (8.75 mmol) 3-nitro-5-(2-oxo-pyrrolidin-1-yl)-benzoic acid in 50 ml MeOH/THF 3/2 are added 0.2 g Pd/C (10% Engelhard 4505) and the reaction is stirred at rt under hydrogen (1 atm) for 18 h. After filtration through celite the solvent is evaporated at reduced pressure to give the product.

MS (ES−): 219=[M−H]$_-$ $^1$H-NMR (400 MHz, d6-DMSO): 7.34 (s, 1H), 7.18 (s, 1H), 6.98 (s, 1H). 5.46 (br s, 2H), 3.79 (t, 2H), 2.49 (t, 2H), 2.10-1.99 (m, 2H).

d) 3-Hydroxy-5-(2-oxo-pyrrolidin-1-yl)-benzoic acid

To the solution of 1.33 g (6.0 mmol) 3-amino-5-(2-oxo-pyrrolidin-1-yl)-benzoic acid in 15 ml water and 0.75 ml (13.3 mmol, 2.2 eq) concentrated sulfuric at 0° C. are added 0.56 g (8.2 mmol, 1.35 eq) sodium nitrit. After addition of 10 ml water the reaction is heated to 90° C. After cooling to rt the reaction is extracted with EtOAc, the organic layer is dried over sodium sulfate and the solvent is evaporated at reduced pressure to give the product.

MS (ES−): 220=[M−H]$^−$ $^1$H-NMR (400 MHz, d6-DMSO): 9.86 (s, 1H), 7.63 (s, 1H), 7.45 (s, 1H), 7.13 (s, 1H), 3.83 (t, 2H), 2.51 (t, 2H), 2.10-2.02 (m, 2H).

e) 3-Allyloxy-5-(2-oxo-pyrrolidin-1-yl)-benzoic acid

To the solution of 1.57 g (7.1 mmol) 3-hydroxy-5-(2-oxo-pyrrolidin-1-yl)-benzoic acid in 5 ml DMF are added 1.02 g (21.3 mmol, 3 eq) 50% sodium hydride in oil. After gas evolution stops 2.53 ml (28.4 mmol, 4 eq) allylbromide are added and the reaction mixture is stirred 4 days at 60° C. The reaction is diluted with water and extracted with EtOAc. The organic layer is dried over sodium sulfate and the solvent is evaporated at reduced pressure. The resulting ester is redissolved in 40 ml MeOH and 0.347 g (8.2 mmol, 1.2 eq) lithiumhydroxide monohydrate are added. The reaction is stirred at rt for 48 h. After evaporation of part of the solvent at reduced pressure the reaction is taken into water and washed with EtOAc. The aqueous layer is acidified with potassium hydrogensulfate and extracted with EtOAc. Drying over sodium sulfate and evaporation of the solvent at reduced pressure gives the product.

MS (LC/MS): 284=[M+H+Na]⁺
¹H-NMR (400 MHz, CDCl₃): 7.91 (s, 1H), 7.72 (s, 1H), 7.47 (s, 1H), 6.14-4.05 (m, 1H), 5.49 (d, 1H), 5.35 (d, 1H), 4.65 (d, 2H), 3.95 (t, 2H), 2.69 (t, 2H), 2.26-2.17 (m, 2H).

Building block A23: 2-(Allyl-benzyloxycarbonyl-amino)-6-methyl-isonicotinic acid The title compound is obtained by an analogous reaction sequence as described for building block A3 (steps e-g) starting from 2-amino-6-methyl-isonicotinic acid ethyl ester (building block A17b).

HPLC (Nucleosil C-18HD, 4×70 mm, 3 μm, 20-100% MeCN (6 min), 100% MeCN (1.5 min)) retention time: 5.04 min
MS (LC/MS, ES+): 327=[M+H]⁺.
¹H-NMR (400 MHz, CDCl₃): 8.15 (s, 1H), 7.54 (s, 1H), 7.44-7.30 (m, 5H), 6.03-5.93 (m, 1H), 5.30 (s, 2H), 5.20 (d, 1H), 5.14 (d, 1H), 4.71 (d, 2H), 2.61 (s, 3H).

Building block C1: (S)-3-(3-Benzyloxy-phenyl)-2-tert-butoxycarbonylamino-propionic acid methyl ester The non-natural amino acid building block C1 is prepared, for example, as disclosed in Tetrahedron, 2002, 58, 6951-6963, or J. Am. Chem. Soc., 1993,115, 10125-10138 (m.p.: 80-81° C.).
$[\alpha]_D^{22}$: +39.1° (c=1.29, CHCl₃).
Rf (DCM/EtOAc=90/10): 0.69.
MS (ES+): 408=[M+Na]⁺.
¹H-NMR (400 MHz, DMSO-d₆): 7.45-7.29 (m, 5H), 7.27 (d, 1H), 7.18 (t, 1H), 6.89 (s, 1H), 6.87-6.81 (m, 1H), 6.79 (d, 1H), 5.06 (s, 2H), 4.21-4.14 (m, 1H), 3.60 (s, 3H), 2.99-2.92 (m, 1H), 2.84-2.77 (m, 1H), 1.33 (s, 9H).

Building block C2: (S)-3-(3-Bromo-phenyl)-2-tert-butoxycarbonylamino-propionic acid methyl ester The product is prepared analogously to building block C1, using 3-bromo-benzaldehyde instead of 3-benzyloxy-benzaldehyde (m.p.: 60-61° C.).
$[\alpha]_D^{22}$: +50.8° (c=1.00, CHCl₃).
Rf (DCM/EtOAc=90/10): 0.54.
MS (ES+): 380=[M+Na]⁺.
¹H-NMR (400 MHz, DMSO-d₆): 7.44 (s, 1H), 7.41-7.36 (m, 1H), 7.30 (d, 1H), 7.23 (d, 2H), 4.23-4.15 (m, 1H), 3.62 (s, 3H), 3.04-2.98 (m, 1H), 2.87-2.79 (m, 1H), 1.32 (s, 9H).

Building block C3: (S)-3-(3-Allyloxy-phenyl)-2-tert-butoxycarbonylamino-propionic acid methyl ester a) (S)-2-tert-Butoxycarbonylamino-3-(3-hydroxy-phenyl)-propionic acid methyl ester A solution of 5.81 g (15 mmol) of building block C1 in 150 ml of EtOH is stirred at rt in the presence of 1.5 g of Pd/C (10%) under a hydrogen atmosphere for 2 h. The catalyst is filtered off, and the filtrate is evaporated to give the product in the form of a colorless solid (m.p.: 61-65° C.).
Rf (DCM/EtOAc=80/20): 0.34.
MS (ES+): 318=[M+Na]⁺.

¹H-NMR (400 MHz, DMSO-d₆): 9.27 (s, 1H), 7.22 (d, 1H), 7.04 (t, 1H), 6.63-6.56 (m, 3H), 4.15-4.07 (m, 1H), 3.60 (s, 3H), 2.91-2.84 (m, 1H), 2.79-2.71 (m, 1H), 1.33 (s, 9H).

b) (S)-3-(3-Allyloxy-phenyl)-2-tert-butoxycarbonyl-lamino-propionic acid methyl ester To a solution of 2.34 g (7.5 mmol) of (S)-2-tert-butoxycarbonylamino-3-(3-hydroxy-phenyl)-propionic acid methyl ester in 15 ml of acetone 1.25 g (9.75 mmol) of powdered K₂CO₃ and 0.76 ml (9 mmol) of allylbromide are added. The reaction mixture is stirred for 16 h at 80° C., diluted with 15 ml of water and extracted with DCM (2×15 ml). The combined organic layers are washed with 7.5 ml of 1 M sodium hydroxide and then 7.5 ml of halfsaturated sodium chloride, dried over sodium sulfate and evaporated to give the product in the form of a colorless solid (m.p.: 50-51° C.).
$[\alpha]_D^{22}$: +40.9° (c=1.18, CHCl₃).
Rf (DCM/EtOAc=80/20): 0.70.
MS (ES+): 358=[M+Na]⁺.
¹H-NMR (400 MHz, DMSO-d₆): 7.25 (d, 1H), 7.17 (t, 1H), 6.83-6.75 (m, 3H), 6.08-5.97 (m, 1H), 5.40-5.34 (m, 1H), 5.26-5.21 (m, 1H), 4.52 (d, 2H), 4.19-4.12 (m, 1H), 3.61 (s, 3H), 2.98-2.92 (m, 1H), 2.84-2.77 (m, 1H), 1.33 (s, 9H).

Building block C4: (S)-3-(3-Allyl-phenyl)-2-tert-butoxycarbonylamino-propionic acid methyl ester A solution of 4.21 g (11.75 mmol) of building block C2, 5.58 ml (17.6 mmol) of allyltributyltin and 1.51 g (35.3. mmol) of lithium chloride in 118 ml of N,N-dimethylacetamide is degassed. Under an argon atmosphere 367 mg (0.59 mmol) of SK-CC02-A are added, and the reaction mixture is heated to 100° C. for 17 h. After the addition of 41 ml of saturated potassium fluoride solution at 0° C., the reaction mixture is stirred at rt for 30 min and then filtered and washed with EtOAc (3×59 ml). The layers of the filtrate are separated, the aqueous phase is extracted with 179 ml of EtOAc, and the combined organic layers are washed with water, dried over sodium sulfate and evaporated. The residue is purified by chromatography on silica gel (cyclohexane/EtOAc 90/10), which gives the product in the form of a yellow oil.
Rf (cyclohexane/EtOAc=80/20): 0.31.
MS (ES+): 342.1=[M+Na]⁺.
¹H-NMR (400 MHz, DMSO-d₆): 7.26 (d, 1H), 7.19 (t, 1H), 7.06-6.99 (m, 3H), 5.98-5.87 (m, 1H), 5.18-5.00 (m, 2H), 4.18-4.10 (m, 1H), 3.59 (s, 3H), 3.32 (d, 2H), 2.98-2.91 (m, 1H), 2.87-2.79 (m, 1H), 1.32 (s, 9H).

Building block C5: ((1S,2R)-1-(3-Allyl-benzyl)-3-{benzyloxycarbonyl-[1-(3-isopropyl-phenyl)-cyclopropyl]-amino}-2-hydroxy-propyl)-carbamic acid tert-butyl ester a) [(S)-1-(3-Allyl-benzyl)-3-chloro-2-oxo-propyl]-carbamic acid tert-butyl ester A solution of 1.95 g (6.1 mmol) of building block C4 in 61 ml of THF is cooled to −78° C., and 1.8 ml (24.4 mmol) of chloroiodomethane are added. 20.8 ml (30.5 mmol) of a 1.47 M solution of lithium diisopropylamide in THF are added dropwise, while the temperature of the reaction mixture is maintained below −73° C. The reaction mixture is stirred for 30 min and then carefully quenched with 9.1 ml (159 mmol) of glacial acetic acid, while the temperature is maintained below −65° C. After stirring for 15 min at −78° C., the reaction mixture is allowed to warm to 0° C., diluted with 92 ml of half-saturated aq sodium chloride and extracted with TBME (2×92 ml). The combined organic layers are washed with 92 ml of 1 M sodium sulfite and then 92 ml of water, dried over sodium sulfate and evaporated to give the product.

Rf (cyclohexane/EtOAc=80/20): 0.34.
MS (LC/MS): 359.8=[M+Na]$^+$.

b) [(1S,2S)-1-(3-Allyl-benzyl)-3-chloro-2-hydroxy-propyl]-carbamic acid tert-butyl ester A solution of 471 mg (12.2 mmol) of sodium borohydride in 44 ml of EtOH is cooled to −78° C., and a solution of 3.2 g (6.1 mmol) of [(S)-1-(3-allyl-benzyl)-3-chloro-2-oxo-propyl]-carbamic acid tert-butyl ester in 90 ml of ethanol is added dropwise, while the temperature of the reaction mixture is maintained below −75° C. The reaction mixture is stirred at −78° C. for 1 h and then allowed to warm to rt within 17 h. At −78° C., 31 ml of 1 M HCl are added dropwise. The reaction mixture is allowed to warm to rt, the ethanol is evaporated, and the residual aqueous solution is extracted with EtOAc (2×61 ml). The combined organic layers are washed with 61 ml of half-saturated sodium chloride solution, dried over sodium sulfate and evaporated. The residue is purified by chromatography on silica gel (cyclohexane/EtOAc 90/10 to 80/20) and gives the product in the form of a pale brown solid (m.p.: 123-126° C.).

Rf (cyclohexane/EtOAc=80/20): 0.19.
MS (ES+): 362.2=[M+H]$^+$.
$^1$H-NMR (400 MHz, DMSO-d$_6$): 7.15 (t, 1H), 7.04-4.94 (m, 3H), 6.67 (d, 1H), 5.97-5.87 (m, 1H), 5.40 (d, 1H), 5.09-4.99 (m, 2H), 3.68-3.52 (m, 3H), 3.49-3.43 (m, 1H), 3.00-2.94 (m, 1H), 2.58-2.52 (m, 1H), 1.28 (s, 9H).

c) [(S)-2-(3-Allyl-phenyl)-1-(S)-oxiranyl-ethyl]-carbamic acid tert-butyl ester A solution of 3.20 g (10.5 mmol) of [(1S,2S)-1-(3-allyl-benzyl)-3-chloro-2-hydroxy-propyl]-carbamic acid tert-butyl ester in a mixture of 19 ml of THF, 19 ml of MeOH and 21 ml (21 mmol, 2 eq) of 1 N aq sodium hydroxide is stirred at rt for 3 h. The reaction mixture is diluted with 80 ml of saturated aq ammonium chloride solution and extracted with DCM. The organic layer is dried over sodium sulfate and evaporated to give the product.

MS (LC/MS): 326=[M+Na]$^+$.
$^1$H-NMR (400 MHz, CDCl$_3$): 7.27 (d, 1H), 7.12-7.08 (m, 3H), 6.05-5.94 (m, 1H), 5.13 (d, 1H), 5.09 (s, 1H), 4.47 (br s, 1H), 3.71 (br s, 1H), 3.41 (d, 2H), 3.01-2.78 (m, 5H), 1.42 (s, 9H).

d) {(1S,2R)-1-(3-Allyl-benzyl)-2-hydroxy-3-[1-(3-isopropyl-phenyl)-cyclopropylamino]-propyl}-carbamic acid tert-butyl ester

[(S)-2-(3-Allyl-phenyl)-1-(S)-oxiranyl-ethyl]-carbamic acid tert-butyl ester (2.4 g, 7.04 mmol, 1 eq) is dissolved in 1-(3-isopropyl-phenyl)-cyclopropylamine (building block D1, 5.13 g, 24.2 mmol, 3.44 eq). The reaction mixture is heated to 80° C. for 15 h and purified by column chromatography using diethyl ether/NH$_3$ (25% in H$_2$O) in a ratio of 200 to 1 to give the product.

MS (ES+): 479=[M+H]$^+$.
HPLC (Nucleosil C18HD, 20-100% MeCN) retention time: 5.11 min.
$^1$H-NMR (400 MHz, CDCl$_3$): 7.28-7.03 (m, 8H), 6.03-5.92 (m, 1H), 5.13-5.02 (m, 2H), 4.52 (d, 1H), 3.80-3.68 (m, 1H), 3.40-3.34 (m, 3H), 3.02-2.77 (m, 3H), 2.72 (d, 2H), 1.33 (s, 9H), 1.26 (d, 6H), 1.03-0.90 (m, 4H).

e) ((1S,2R)-1-(3-Allyl-benzyl)-3-{benzyloxycarbonyl-[1-(3-isopropyl-phenyl)-cyclopropyl]-amino}-2-hydroxy-propyl)-carbamic acid tert-butyl ester {(1S,2R)-1-(3-Allyl-benzyl)-2-hydroxy-3-[1-(3-isopropyl-phenyl)-cyclopropylamino]-propyl}-carbamic acid tert-butyl ester (2.7 g, 5.08 mmol, 1 eq) is dissolved in DCM (25 ml). Saturated, aq Na$_2$CO$_3$ is added, followed by CbzCl (50% in toluene, 2.04 ml, 6.1 mmol, 1.2 eq). The reaction mixture is stirred for 2 h at rt and then diluted with water (80 ml) and DCM (160 ml). The organic layer is washed with water and then brine, dried over sodium sulfate, filtered and concentrated. The residue is purified by column chromatography using EtOAc/hexane in a ratio of 1 to 4 to give the product.

MS (ES+): 613=[M+H]$^+$.
HPLC (Nucleosil C18HD, 4×70 mm, 3 µm, 20-100% MeCN (6 min), 100% MeCN (1.5 min)) retention time: 7.41 min.

Building block C6: ((1S,2R)-1-(3-Allyloxy-benzyl)-3-{benzyloxycarbonyl-[1-(3-tert-butyl-phenyl)-cyclopropyl]-amino}-2-hydroxy-propyl)-carbamic acid tert-butyl ester The product is obtained by an analogous reaction sequence as for building block C5, starting from building block C3 and 1-(3-tert-butyl-phenyl)-cyclopropylamine (building block D2).

MS (ES+): 643=[M+H]$^+$.
HPLC (Nucleosil C18HD, 4×70 mm, 3 µm, 20-100% MeCN (6 min), 100% MeCN (1.5 min)) retention time: 7.32 min.

Building block C7: ((1S,2R)-1-(3-Allyloxy-benzyl)-3-{benzyloxycarbonyl-[1-(3-isopropyl-phenyl)-cyclopropyl]-amino}-2-hydroxy-propyl)-carbamic acid tert-butyl ester The product is obtained by an analogous reaction sequence as for building block C5, starting from building block C3.

MS (ES+): 629=[M+H]$^+$.
HPLC (Nucleosil C18HD, 4×70 mm, 3 µm, 20-100% MeCN (6 min), 100% MeCN (1.5 min)) retention time: 7.23 min.

Building block C8: [(2R,3S)-4-(3-Allyl-phenyl)-3-tert-butoxycarbonylamino-2-hydroxy-butyl]-[1-(4-tert-butyl-pyrid-2-yl)-cyclopropyl]-carbamic acid benzyl ester The product is obtained by an analogous reaction sequence as for building block C5, starting from building block C4 and 1-(4-tert-butyl-pyrid-2-yl)-cyclopropylamine (building block D3).

Rf (hexane/EtOAc=3/2): 0.45.
MS (LC/MS, ES+): 628=[M+H]$^+$.
HPLC (Zorbax SB-C18, 3×30 mm, 1.8 µm, 40-100% MeCN (3.25 min), 100% MeCN (0.75 min)) retention time: 3.36 min.
$^1$H-NMR (400 MHz, CDCl$_3$): 8.39 (br s, 1H), 7.41 (d, 1H), 7.4-7.0 (m, 11H), 6.92 (br s, 1H), 6.03-5.90 (m, 1H), 5.15-5.05 (m, 4H), 4.74 (d, 1H), 3.9-3.75 (m, 2H), 3.4-3.3 (m, 2H), 3.1-2.85 (m, 2H), 1.6-1.2 (m, 4H, 1.35 (s, 9H), 1.3211.26 (s, 9H).

Building block C9: (S)-3-(3-Allyloxy-4-fluoro-phenyl)-2-tert-butoxycarbonylamino-propionic acid methyl ester a) 4-Fluoro-3-hydroxy-benzoic acid methyl ester 4-Fluoro-3-hydroxy-benzoic acid (24.7 g, 112.8 mmol) is dissolved in methanol (300 ml) and cooled to 0° C. Thionyl Chloride (15 ml) is added dropwise and the mixture then heated at 70° C. for 60 min. The reaction mixture is concentrated in vacuo, taken up in EtOAc and washed with saturated sodium bicarbonate solution followed by saturated brine. The organic layer is dried over sodium sulfate, filtered and concentrated under reduced pressure to afford the title compound as a white solid.

HPLC/MS (SunFire C18 20×4.6 mm, 3.5 μm, reverse phase; Column temperature 40° C., 3 ml/min, 05-100% MeCN containing 0.1% trifluoroacetic acid (4 min) retention time: 2.34 min MS (LC/MS, ES+): 171=[M+H]$^+$
$^1$H-NMR (400 MHz, DMSO-d$_6$): 10.40 (s, 1H), 7.65 (dd, 1H), 7.40 (m, 1H), 7.35 (m, 1H), 3.80 (s, 3H).

b) 3-Allyloxy-4-fluoro-benzoic acid methyl ester

4-Fluoro-3-hydroxy-benzoic acid methyl ester (26.3 g, 154.5 mmol) is dissolved in acetone (300 ml). Potassium carbonate (42.7 g, 305.8 mmol) is added, followed 5 minutes later by the addition of allyl bromide (20 ml, 229 mmol). The reaction mixture is stirred overnight at rt, concentrated in vacuo and then diluted with ether and water. The organic layer is washed with saturated brine, dried over sodium sulfate, filtered and concentrated to give the product as a colourless oil.

$^1$H-NMR (400 MHz, DMSO-d$_6$): 7.67 (dd, 1H), 7.60 (m, 1H), 7.40 (dd, 1H), 6.1-6.0 (m, 1H), 5.45-5.30 (m, 2H), 4.72 (d, 2H), 3.85 (s, 3H).

c) (3-Allyloxy-4-fluoro-phenyl)-methanol

3-Allyloxy-4-fluoro-benzoic acid methyl ester (5.0 g, 23.5 mmol) is dissolved in THF under an argon atmosphere. Lithium aluminium hydride solution (17.7 ml, 1M in THF, 17.7 mmol) is added at rt, and the reaction mixture is stirred at rt for 55 minutes, quenched by dropwise addition of water, then solid sodium sulphate is added. The resulting slurry is filtered through celite and the filter cake washed with methanol. The filtrate is absorbed onto silica and purified by chromatography on silica (EtOAc) to give the product as a colourless oil.

HPLC/MS (SunFire C18 20×4.6 mm, 3.5 μm, reverse phase; Column temperature 40° C., 3 ml/min, 05-100% MeCN containing 0.1% trifluoroacetic acid (4 min) retention time: 2.52 min MS (LC/MS, ES+): 205=[M+Na]$^+$
$^1$H-NMR (400 MHz, DMSO-d$_6$): 7.15 (dd, 1H), 7.10 (dd, 1H), 6.87 (m, 11H), 6.1-6.0 (m, 1H), 5.45-5.30 (m, 2H), 4.60 (d, 2H), 4.42 (s, 2H).

d) 2-Allyloxy-4-chloromethyl-1-fluoro-benzene

A solution of (3-allyloxy-4-fluoro-phenyl)-methanol (3.76 g, 20.7 mmol) in thionylchloride (3.04 ml, 41.3 mmol) is mixed at 0° C. and then stirred at rt for 2-5 h. Excess thionylchloride is evaporated, the residue diluted with DCM and 1 M aq sodium carbonate. The layers are separated, the aqueous phase extracted with DCM, the combined organic layers are dried over sodium sulfate and evaporated. The residue is purified by chromatography on silica gel (hexane/Et$_2$O 95/5) to give the product as yellowish oil.

Rf (hexane/Et$_2$O=80/20): 0.54.
$^1$H-NMR (400 MHz, DMSO-d$_6$): 7.25 (dd, 1H), 7.20 (dd, 1H), 7.03-6.99 (m, 1H), 6.09-5.99 (m, 1H), 5.41 (dd, 1H), 5.28 (dd, 1H), 4.71 (s, 2H), 4.65-4.63 (m, 2H).

e) 2-Acetylamino-2-(3-allyloxy-4-fluoro-benzyl)-malonic acid diethyl ester

Sodium metal (324 mg, 14.0 mmol) is slowly dissolved in EtOH (18 ml). To this solution are added 2-acetylamino-malonic acid diethyl ester (3.45 g, 15.4 mmol) and a solution of 2-allyloxy-4-chloromethyl-1-fluoro-benzene (2.81 g, 14.0 mmol) in EtOH. The mixture is heated at 85° C. for 18 h. The solvent is removed at reduced pressure and the residue is dissolved in DCM/EtOH (80:20) and washed with water. After back washing the aqueous layer with DCM/EtOH (80:20) the combined organic layers are dried over sodium sulfate and evaporated. The residue crystallizes upon standing and is washed with hexane (3×) to give the product as colorless crystals.

m.p.: 53-57° C.
Rf (DCM/MeOH=99/1): 0.21.
MS (ES+): 382=[M+H]$^+$.
$^1$H-NMR (400 MHz, DMSO-d$_6$): 8.13 (s, 1H), 7.08 (dd, 1H), 6.67 (dd, 1H), 6.55-6.51 (m, 1H), 6.08-5.99 (m, 1H), 5.36 (dd, 1H), 5.25 (dd, 1H), 4.57 (d, 2H), 4.12 (q, 4H), 3.36 (s, 2H), 1.95 (s, 3H), 1.16 (t, 6H).

f) 2-Acetylamino-2-(3-allyloxy-4-fluoro-benzyl)-malonic acid monoethyl ester sodium salt To a solution of 2-acetylamino-2-(3-allyloxy-4-fluoro-benzyl)-malonic acid diethyl ester (5.15 g, 13.5 mmol) in EtOH (65 ml) are added at 0° C. 1N sodium hydroxide (18 ml, 18 mmol) and the mixture is stirred at rt for 5 h. The solvent is evaporated and the residue is used for the next step without further purification.

Rf (DCM/MeOH/NH$_3$=80/18/2): 0.27
MS (ES+): 354=[M+H]$^+$, 310=[M−Ac]$^+$
$^1$H-NMR (400 MHz, CDCl$_3$): 6.92 (dd, 1H), 6.86 (s, 1H), 6.64 (dd, 1H), 6.59-6.55 (m, 1H), 6.07-5.97 (m, 1H), 5.39 (dd, 1H), 5.27 (dd, 1H), 4.49 (d, 2H), 4.20 (t, 2H), 3.53 (q, 2H), 3.20 (br s, 1H), 1.97 (s, 3H), 1.26 (t, 3H).

g) 2-Acetylamino-3-(3-allyloxy-4-fluoro-phenyl)-propionic acid ethyl ester

A solution of 2-acetylamino-2-(3-allyloxy-4-fluoro-benzyl)-malonic acid monoethyl ester sodium salt (5.46 g, 13.3 mmol) in 53 ml dioxane is heated at 120° C. for 1.5 h. The reaction mixture is diluted with 78 ml DCM and 78 ml water, the layers are separated and the aqueous phase is extracted with DCM. The combined organic layers are washed with saturated brine, dried over sodium sulfate and evaporated. The residue is precipitated from cyclohexane and purified by chromatography on silica gel (cyclohexane/EtOAc 95/5), which gives the product as colorless residue that solidifies upon standing.

M.p.: 73-76° C.
Rf (DC M/MeOH=98/2): 0.27.
MS (ES+): 310=[M+H]$^+$, 236=[M−CO$_2$Et]$^+$.
$^1$H-NMR (400 MHz, DMSO-d$_6$): 7.07 (dd, 1H), 7.01 (dd, 1H), 6.76-6.72 (m, 1H), 6.08-5.98 (m, 1H), 5.38 (dd, 1H), 5.25 (dd, 1H), 4.58 (d, 2H), 4.43-4.37 (m, 1H), 4.03 (q, 2H), 2.93 (dd, 1H), 2.82 (dd, 1H), 1.79 (s, 3H), 1.11 (t, 3H).

h) (S)-3-(3-Allyloxy-4-fluoro-phenyl)-2-tert-butoxycarbonylamino-propionic acid methyl ester The title compound is obtained by an analogous reaction sequence as for building block C13 (steps c-e), starting from 2-acetylamino-3-(allyloxy-4-fluoro-phenyl)-propionic acid ethyl ester.
m.p.: 65-70° C.
Rf (cyclohexane/EtOAc=70/30): 0.41.
MS (ES+): 376=[M+Na]$^+$, 254=[M−Boc+H]$^+$.
$^1$H-NMR (400 MHz, DMSO-d$_6$): 7.25 (d, 1H), 7.09-7.03 (m, 2H), 6.78-6.74 (m, 1H), 6.08-5.98 (m, 1H), 5.39 (dd, 1H), 5.26 (dd, 1H), 4.59 (d, 2H), 4.19-4.13 (m, 1H), 3.60 (s, 3H), 2.95 (dd, 1H), 2.78 (dd, 1H), 1.31 (s, 9H).

Building block C10: [(2R,3S)-4-(3-Allyloxy-4-fluoro-phenyl)-3-tert-butoxycarbonylamino-2-hydroxy-butyl]-[1-(2-tert-butyl-phenyl)-cyclopropyl]-carbamic acid benzyl ester The product is obtained by an analogous reaction sequence as for building block C5, starting from (S)-3-(3-allyloxy-4-fluoro-phenyl)-2-tert-butoxycarbonylamino-propionic acid methyl ester (C9) and 1-(3-tert-butyl-phenyl)-cyclopropylamine (D2).
Rf (cyclohexane/EtOAc=80/20): 0.20.
MS (ES+): 661=[M+H]$^+$.
$^1$H-NMR (400 MHz, DMSO-d$_6$, 120° C.): 7.29-7.20 (m, 5H), 7.15-7.11 (m, 3H), 6.99-6.94 (m, 2H), 6.85-6.82 (m, 1H), 6.76-6.72 (m, 1H), 6.15-6.09 (m, 1H), 6.08-5.98 (m, 1H), 5.37 (dd, 1H), 5.23 (dd, 1H), 5.07 (q, 1H), 4.63 (d, 1H), 4.56 (d, 2H), 3.83-3.77 (m, 1H), 3.68 (dd, 1H), 3.59-3.52 (m, 1H), 3.19 (dd, 1H), 2.96 (d, 1H), 2.53 (dd, 1H), 1.79-1.74 (m, 1H), 1.55-1.42 (m, 1H), 1.32-1.17 (m, 2H), 1.26 (s, 9H), 1.22 (s, 9H), 1.10-1.04 (m, 1H).

Building block C11: [(2R,3S)-4-(3-Allyloxy-phenyl)-3-tert-butoxycarbonylamino-2-hydroxy-butyl]-[1-(4-isopropyl-pyridin-2-yl)-cyclopropyl]-carbamic acid benzyl ester The product is obtained by an analogous reaction sequence as for building block C5, starting from building block C3 and 1-(4-isopropyl-pyridin-2-yl)-cyclopropylamine (building block D4).
Rf (hexane/EtOAc=1/1): 0.37.
MS (LC/MS, ES+): 630=[M+H]$^+$.
HPLC (Zorbax SB-C18, 3×30 mm, 1.8 μm, 30-100% MeCN (3.25 min), 100% MeCN (0.75 min)) retention time: 3.41 min.
$^1$H-NMR (400 MHz, CDCl$_3$): 8.42 (br s, 1H), 7.36-7.08 (m, 8H), 6.91-6.77 (m, 4H), 6.14-6.03 (m, 1H), 5.43 (d, 1H), 5.30 (d, 1H), 5.15-5.06 (m, 2H), 4.57-4.49 (m, 2H), 3.87 (s, br, 1H), 3.08-2.8 (m, 3H), 1.55-1.15 (m, 6H), 1.36 (s, 9H), 1.29 (d, 3H), 1.21 (d, 3H).

Building block C12: [(2R,3S)-4-(3-Allyl-phenyl)-3-tert-butoxycarbonylamino-2-hydroxy-butyl]-[1-(4-isopropyl-pyridin-2-yl)-cyclopropyl]-carbamic acid benzyl ester The product is obtained by an analogous reaction sequence as for building block C5, starting from building block C4 and 1-(4-isopropyl-pyrid-2-yl)-cyclopropylamine (building block D4).

Rf (hexane/EtOAc=3/2): 0.41.
MS (LC/MS, ES+): 614=[M+H]$^+$.
HPLC (Zorbax SB-C18, 3×30 mm, 1.8 μm, 40-100% MeCN (3.25 min), 100% MeCN (0.75 min)) retention time: 3.24 min.
$^1$H-NMR (400 MHz, CDCl$_3$): 8.37 (br s, 1H), 7.36-7.0 (m, 11H), 6.77 (br s, 1H), 6.02-5.90 (m, 1H), 5.15-5.05 (m, 4H), 4.74 (s, br, 1H), 3.9-3.75 (m, 2H), 3.4-3.3 (m, 2H), 3.1-2.75 (m, 3H), 1.6-1.2 (m, 4H), 1.35 (s, 9H), 1.27 (d, 3H), 1.22 (d, 3H).

Building block C13: (S)-3-(3-Allyloxy-5-fluoro-phenyl)-2-tert-butoxycarbonylamino-propionic acid methyl ester a) 3-Allyloxy-5-fluoro-benzaldehyde A solution of 14.78 g (64 mmol) 1-allyloxy-3-bromo-5-fluoro-benzene (CAS 477956-04-0) in 500 ml THF is cooled to −85° C. Butyllithium (40 ml, 1.6 m solution in hexane) is added dropwise within 5 minutes. After 5 minutes a solution of 10 ml (128 mmol) DMF in 20 ml THF is added dropwise (T<−65° C.). After the addition the mixture is stirred 5 minutes and then poured onto a stirred mixture of 75 ml 2N aq hydrochloric acid and ice. The mixture is extracted with TBME. The organic phase is washed extensively with water and concentrated. The crude aldehyde is used without purification in the next step.
Rf: (hexane/EtOAc 6:1): 0.45
$^1$H-NMR (400 MHz, CDCl$_3$): 9.94 (s, 1H), 7.25-7.18 (m, 2H), 6.95-6.90 (m, 1H), 6.13-6.02 (m, 1H), 5.50-5.34 (m, 2H), 4.64-4.61 (m, 2H).

b) 4-[1-(3-Allyloxy-5-fluoro-phenyl)-meth-(Z)-ylidene]-2-methyl-4H-oxazol-5-one

A mixture of crude 3-allyloxy-5-fluoro-benzaldehyde (64 mmol), 7.49 g (64 mmol) acetic acid, 5.25 g (64 mmol) sodium acetate and 32.6 g (320 mmol) acetic anhydride is heated at 100° C. for 3.5 h. After cooling to 70° C. the mixture is poured onto a mixture of water, EtOH and ice and stirred vigorously for 0.5 h. The solid is filtered off, washed with water and hexane and dried in vacuo to produce a yellow powder.
Rf: (hexane/EtOAc 6:1): 0.44
$^1$H-NMR (400 MHz, CDCl$_3$): 7.54 (d, 1H), 7.43 (s, 1H), 7.06 (s, 1H), 6.77-6.74 (m, 1H), 6.13-6.03 (m, 1H), 5.52-5.35 (m, 2H), 4.62-4.60 (m, 2H), 2.45 (s, 3H).

c) 2-Acetylamino-3-(3-allyloxy-5-fluoro-phenyl)-propionic acid methyl ester

To a solution of 14.7 g (56.3 mmol) 4-[1-(3-allyloxy-5-fluoro-phenyl)-meth-Z)-ylidene]2-methyl-4H-oxazol-5-one in 500 ml MeOH are added 1 magnesium turnings. The mixture is heated to 40° C. and after an induction period an exothermic reaction starts. After the magnesium has been consumed more turnings are added portionwise at such a rate that a temperature of 40-45° C. is maintained. The total amount of magnesium added is 4.5 g (187 mmol). The reaction mixture is poured onto a mixture of 200 ml 2N aq hydrochloric acid and ice and extracted with EtOAc. The organic phase is washed with water and 5% aq sodium bicarbonate, dried over sodium sulfate and purified by chromatography on silica gel (hexane/EtOAc 1:1, 1:2) followed by crystallization from EtOAc/hexane, to give colorless crystals.

HPLC (Zorbax SB-C18, 3×30 mm, 1.8 μm, 30-100% MeCN (3.25 min), 100% MeCN (0.75 min)): 2.137 min.
MS (ES+): 296=[M+H]⁺
¹H-NMR (400 MHz, CDCl₃): 6.55 (d, 1H), 6.49 (s, 1H), 6.44 (d, 1H), 6.12-6.00 (m, 1H), 5.95 (br d, NH), 4.55 (q, 1H), 4.53 (d, 2H), 3.78 (s, 3H), 3.16-3.05 (m, 2H), 2.05 (s, 3H).

d) (S)-3-(3-Allyloxy-5-fluoro-phenyl)-2-tert-butoxy-carbonylamino-propionic acid The solution of 5.42 g racemic 2-acetylamino-3-(3-allyloxy-5-fluoro-phenyl)-propionic acid methyl ester in 2.4 ml toluene is added to 40 ml phosphate buffer pH 7.5. This mixture is treated with 300 μl Alcalase Typ DX (Lot: PMN0466) under pH-stat conditions. When the conversion reaches 48% the reaction mixture is washed with DCM [(R)-3-(3-allyloxy-5-fluoro-phenyl)-2-tert-butoxycarbonyl-amino-propionic acid methyl ester can be isolated from the organic extracts]. The aqueous phase is adjusted to pH 8 and cobalt(II)chloride is added to 0.1 mM final concentration. After addition of 400 mg Acylase Amano (Lot: ACV12502) the mixture is stirred at rt. When conversion is complete 70 ml THF and 2.53 g (18.35 mmol) sodium carbonate are added. At 0° C. 3.0 g (18.35 mmol) di-tert-butyl dicarbonate is added and the reaction is stirred at rt for 5 h. The organic solvent is evaporated at reduced pressure and remaining aqueous phase acidified to pH 3 and extracted with EtOAc. The combined organic layers are dried over magnesium sulfate and the solvent is evaporated under reduced pressure to give the yellow product.
¹H-NMR (CDCl₃): 6.50-6.54 (m, 3H), 5.97-6.06 (m, 1H), 5.39 (m, 1H), 5.28 (m, 1H), 4.99 (d, 1H), 4.49 (dt, 2H), 2.99-3.19 (m, 2H), 1.43 (s, 9H).

e) (S)-3-(3-Allyloxy-5-fluoro-phenyl)-2-tert-butoxy-carbonylamino-propionic acid methyl ester To a solution of (S)-3-(3-allyloxy-5-fluoro-phenyl)-2-tert-butoxycarbonylamino-propionic acid methyl ester in methanol is slowly added a solution of diazomethane in diethyl ether until complete conversion. The excess diazomethane is destroyed by addition of concentrated acetic acid (100 μl) and the reaction mixture is then concentrated under reduced pressure. The residue is dissolved in DCM and washed with water. The organic layer is dried over magnesium sulfate and the solvent is evaporated to give the product as a colourless oil.
¹H-NMR (CDCl₃): 6.42-6.54 (m, 3H), 5.98-6.07 (m, 1H), 5.41 (dq, 1H), 5.30 (dq, 1H), 5.0 (d, 1H), 4.57 (q, 1H), 4.49 (dt, 2H), 3.68 (s, 3H), 2.97-3.1 (m, 2H), 1.43 (s, 9H).
HPLC (Chiralpak AS-H 1205, 250×4.6 mm, 5 μl, hexane/isopropanol 95/5, 1 ml/min) retention time: 10.75 min, >99.9% e.e. (retention time of (R)-enantiomer: 8.48 min)

Building block C14: {(1S,2R)-1-(3-Allyloxy-5-fluoro-benzyl)-2-hydroxy-3-[1-(3-isopropyl-phenyl)-cyclopropylamino]-propyl}-carbamic acid tert-butyl ester The product is obtained by an analogous reaction sequence as for building block C5, starting from {(1S,2R)-1-(3-allyloxy-5-fluoro-benzyl)-2-hydroxy-3-[1-(3-isopropyl-phenyl)-cyclopropylamino]-propyl}-carbamic acid tert-butyl ester (building block C13) and 1-(3-isopropyl-phenyl)-cyclopropylamine (building block D1).
Rf: (hexane/EtOAc 1:1): 0.5
HPLC (Zorbax SB-C18, 3×30 mm, 1.8 μm, 30-100% MeCN (3.25 min), 100% MeCN (0.75 min)): 3.256 min
MS (ES+): 513=[M+H]⁺
¹H-NMR (400 MHz, CDCl₃): 7.23-7.06 (m, 4H), 6.60-6.45 (m, 4H), 6.13-5.95 (m, 1H), 5.43-5.25 (m, 2H), 4.51-4.44 (m, 3H), 3.76-3.68 (m, 1H), 3.57-3.45 (m, 1H), 3.37-3.30 (m, 1H), 2.98-2.64 (m, 4H), 1.30 (s, 9H), 1.23 (d, 6H), 1.1-0.87 (m, 4H).

Building block C16: [(1S,2R)-3-[1-(4-tert-Butyl-pyridin-2-yl)-cyclopropylamino]-2-hydroxy-1-(3-hydroxy-benzyl)-propyl]-carbamic acid tert-butyl ester a) {(1S,2R)-1-(3-Benzyloxy-benzyl)-3-[1-(4-tert-butyl-pyridin-2-yl)-cyclopropylamino]-2-hydroxy-propyl}-carbamic acid tert-butyl ester A solution of 5.53 g (15 mmol) [(S)-2-(3-benzyloxy-phenyl)-1-(S)-oxiranyl-ethyl]-carbamic acid tert-butyl ester (J. Med. Chem. 1996, 39, 1991) and 3.42 g (18 mmol) 1-(4-tert-butyl-pyrid-2-yl)-cyclopropylamine (building block D4) in 70 ml EtOH is stirred at 50° C. for 60 h. The mixture is evaporated and chromatographed on silica gel (EtOAc/hexanes 1:8, 1:5, 1:3, 1:1, 2:1).
Rf: (DCM/MeOH/25% aq NH₃ 90/9/1): 0.45
HPLC (Zorbax SB-C18, 3×30 mm, 1.8 μm, 30-100% MeCN (3.25 min), 100% MeCN (0.75 min): 3.323 min
MS (ES+): 560=[M+H]⁺
¹H-NMR (400 MHz, CDCl₃): 8.44 (d, 1H), 7.50-7.10 (m, 8H), 6.91-6.83 (m, 3H), 5.07 (s, 2H), 4.64 (d, 1H), 4.88-4.80 (m, 1H), 4.54-4.48 (m, 1H), 3.01-2.75 (m, 4H), 1.36 (br s, 9H), 1.32 (s, 9H), 1.28-1.18 (m, 4H).

b) [(1S,2R)-3-[1-(4-tert-Butyl-pyridin-2-yl)-cyclopropylamino]-2-hydroxy-1-(3-hydroxy-benzyl)-propyl]-carbamic acid tert-butyl ester A solution of 4.9 g (8.75 mmol) {(1S,2R)-1-(3-benzyloxy-benzyl)-3-[1-(4-tert-butyl-pyridin-2-yl)-cyclopropylamino]-2-hydroxy-propyl}-carbamic acid tert-butyl ester in 50 ml EtOH is hydrogenated in the presence of 0.49 g Pd—C 10% (Engelhardt 4505) for 12 h. The mixture is filtered over high-flow and purified by chromatography on silica gel using a gradient of DCM with 2-10% of 9/1 MeOH/25% aq NH₃.
Rf: (DCM/MeOH/25% aq NH₃ 90/9/1): 0.23
HPLC (Zorbax SB-C18, 3×30 mm, 1.8 μm, 30-100% MeCN (3.25 min), 100% MeCN (0.75 min): 2.394 min
MS (ES+): 470=[M+H]⁺
¹H-NMR (400 MHz, CDCl₃): 8.44 (d, 1H), 7.20-7.11 (m, 3H), 6.80-6.70 (m, 3H), 4.74 (d, 1H), 3.89-3.80 (m, 1H), 3.57-3.50 (m, 1H), 2.95-2.73 (m, 4H), 1.35 (br s, 9H), 1.30 (s, 9H), 1.28-1.18 (m, 4H).

Building block C17: [(2R,3S)-3-tert-Butoxycarbonyl-amino-2-hydroxy-4-(3-hydroxy-phenyl)-butyl]-[1-(3-isopropyl-phenyl)-cyclopropyl]-carbamic acid benzyl ester Under an atmosphere of nitrogen a solution of 0.70 g (1.11 mmol) [(2R,3S)-4-(3-allyloxy-phenyl)-3-tert-butoxycarbonylamino-2-hydroxy-butyl]-[1-(3-isopropyl-phenyl)-cyclopropyl]-carbamic acid benzyl ester (building block C7) and 12 mg (0.01 mmol) Pd(PPh₃)₄ in 7 ml MeOH is stirred for 2.5 h in the presence of 461 mg (3.34 mmol) potassium carbonate. The mixture is quenched with 5 ml 1 N aq hydrochloric acid and extracted with EtOAc. The organic phase is washed with water, concentrated and chromatographed on silica gel (EtOAc/hexane 1:2)

Rf: (hexane/EtOAc=1/1): 0.60
HPLC (Nucleosil C18-HD, 4×70 mm, 3 μm, 40-100% MeCN (6 min), 100% MeCN (1.5 min)): 5.66 min
MS(ES) MH$^+$=589

Building block C18: [(2R,3S)-4-(3-Allyloxy-phenyl)-3-tert-butoxycarbonylamino-2-hydroxy-butyl]-[1-(4-tert-butyl-pyridin-2-yl)-cyclopropyl]-carbamic acid benzyl ester The product is obtained by an analogous reaction sequence as for building block C5, starting from building block C4 and 1-(4-tert-butyl-pyrid-2-yl)-cyclopropylamine (building block D3).

Rf (hexane/EtOAc=3/2): 0.38.
MS (LC/MS, ES+): 644=[M+H]$^+$.
HPLC (Zorbax SB-C18, 3×30 mm, 1.8 μm, 30-100% MeCN (3.25 min), 100% MeCN (0.75 min)) retention time: 3.52 min.
$^1$H-NMR (400 MHz, CDCl$_3$): 8.38 (br s, 1H), 7.4-6.77 (m, 12H), 6.12-6.00 (m, 1H), 5.43 (d, 1H), 5.30 (d, 1H), 5.15-5.05 (m, 2H), 4.78 (s, br, 1H), 4.55-4.45 (m, 2H), 3.95-3.75 (m, 2H), 3.1-2.85 (m, 2H), 1.5-1.2 (m, 4H), 1.35 (s, 9H), 1.32/1.26 (s, 9H).

Building block C19: [(2R,3S)-4-(3-Allyloxy-phenyl)-3-tert-butoxycarbonylamino-2-hydroxy-butyl]-{1-[5-(2,2-dimethyl-propyl)-isoxazol-3-yl]-cyclopropyl}-carbamic acid benzyl ester The product is obtained by an analogous reaction sequence as for building block C5, starting from building block C3 and 1-[5-(2,2-dimethyl-propyl)-isoxazol-3-yl]-cyclopropylamine (building block D5).

MS (ES+): 648=[M+H]$^+$
HPLC (Nucleosil C18HD, 4×70 mm, 3 μm, 20-100% MeCN (6 min), 100% MeCN (1.5 min)) retention time=6.95 min Building block C20: [(2R,3S)-4-(3-Allyloxy-phenyl)-3-tert-butoxycarbonylamino-2-hydroxy-butyl]-(2-phenyl-cyclopropyl)-carbamic acid benzyl ester The product is obtained as a mixture of two diastereomers by an analogous reaction sequence as for building block C5, starting from building block C3 and the commercially available racemic trans-2-phenyl-cyclopropylamine.

MS (ES+): 587=[M+H]$^+$
HPLC (Nucleosil C18HD, 4×70 mm, 3 μm, 20-100% MeCN (6 min), 100% MeCN (1.5 min)) retention time=6.62 min Building block C21: [(2R,3S)-4-(3-Allyloxy-phenyl)-3-tert-butoxycarbonylamino-2-hydroxy-butyl]-[1-(3-propyl-isoxazol-5-yl)-cyclopropyl]-carbamic acid benzyl ester The product is obtained by an analogous reaction sequence as for building block C5, starting from building block C3 and 1-(3-propyl-isoxazol-5-yl)-cyclopropylamine (building block D6).

MS (ES+): 620=[M+H]$^+$
HPLC (Nucleosil C18HD, 4×70 mm, 3 μm, 20-100% MeCN (6 min), 100% MeCN (1.5 min)) retention time=6.52 min Building block C22: [(2R,3S)-4-(3-Allyloxy-phenyl)-3-tert-butoxycarbonylamino-2-hydroxy-butyl]-[1-(3-bromo-phenyl)-cyclopropyl]-carbamic acid benzyl ester The product is obtained by an analogous reaction sequence as for building block C5, starting from building block C3 and 1-(3-bromo-phenyl)-cyclopropylamine. The later is obtained following a published procedure (WO2006074940).

MS (ES+): 667 and 665=[M+H]$^+$
$^1$H-NMR (400 MHz, DMSO-d$_6$): 7.40-7.03 (m, 9H), 7.01-6.89 (m, 1H), 6.82-6.70 (m, 3H), 6.10-5.99 (m, 1H), 5.42-5.22 (m, 2H), 5.15 (s, 2H), 4.65-4.55 (s, 1H), 4.50 (d, 2H), 3.82-3.40 (m, 4H), 3.00-2.80 (m, 2H), 1.50-1.08 (m, 4H), 1.29 (s, 9H).

Building block D1:
1-(3-Isopropyl-phenyl)-cyclopropylamine a) 3-Isopropyl-benzonitrile 1-Bromo-3-isopropylbenzene (200 g, 954 mmol, 1 eq) is dissolved in 1 l of 1-methyl-2-pyrrolidone. Zinc cyanide (114 g, 954 mmol, 1 eq) and Pd(PPh$_3$)$_4$ (28.7 g, 24.8 mmol, 0.03 eq) are added under nitrogen. The reaction mixture is heated to 125° C., stirred at this temperature for 150 min, then cooled to rt and filtered over Hyflo Super Gel, and the filtrate is diluted with H$_2$O and EtOAc. The organic layer is washed with water, 1 N HCl solution and brine, dried over sodium sulfate, filtered and concentrated. The residue is purified by column chromatography using DCM/hexane in a ratio of 1 to 3 to give the product.

HPLC (Nucleosil C18HD, 4×70 mm, 3 μm, 20-100% MeCN (6 min), 100% MeCN (3 min)) retention time: 5.06 min.
$^1$H-NMR (400 MHz, CDCl$_3$): 7.57 (s, 1H), 7.53-7.48 (m, 2H), 7.43 (t, 1H), 3.01-2.92 (m, 1H), 1.29 (d, 6H).

b) 1-(3-Isopropyl-phenyl)-cyclopropylamine

3-Isopropyl-benzonitrile (42 g, 286 mmol, 1 eq) is dissolved in 670 ml of diethyl ether under argon. Titanium(IV)-isopropoxide (90.4 g, 315 mmol, 1.1 eq) is added. The reaction mixture is cooled to −70° C., and EtMgBr (3 M in diethyl ether, 210 ml, 630 mmol, 2.2 eq) is added within 60 min. The reaction mixture is warmed to 10° C., and BF$_3$*Et$_2$O (48%, 169 g, 573 mmol, 2 eq) is added at this temperature. After 1 h, the reaction mixture is quenched with 400 ml of 1 N HCl, basified to pH 10 using 2 N NaOH in H$_2$O and filtered over Hyflo Super Gel. The organic layer is dried over sodium sulfate, filtered and concentrated. The residue is purified by column chromatography using DCM/MeOH in a ratio of 19 to 1 to give the product.

HPLC (Nucleosil C18HD, 4×70 mm, 3 μm, 20-100% MeCN (6 min), 100% MeCN (3 min)) retention time: 2.80 min.
$^1$H-NMR (400 MHz, CDCl$_3$): 7.32-7.28 (t, 1H), 7.23 (s, 1H), 7.19-7.10 (m, 2H), 3.01-2.90 (m, 1H), 1.96 (s, 2H), 1.33 (d, 6H), 1.12-1.09 (m, 2H), 1.09-1.02 (m, 2H).

Building block D2:
1-(3-tert-Butyl-phenyl)-cyclopropylamine

The product is obtained by an analogous reaction sequence as for building block D1, starting from 1-Bromo-3-tert-butyl-benzene.

Rf (cyclohexane/EtOAc=50/50): 0.19.
MS (LC/MS): 190.1=[M+H]$^+$.
$^1$H-NMR (400 MHz, CDCl$_3$): 7.40-7.38 (m, 1H), 7.27-7.26 (m, 2H), 7.15-7.12 (m, 1H), 1.91 (br s, 2H), 1.35 (s, 9H), 1.09-1.05 (m, 2H), 1.03-0.99 (m, 2H).

Building block D3:
1-(4-tert-Butyl-pyrid-2-yl)-cyclopropylamine

The product is obtained by an analogous reaction sequence as for building block D1 starting from 4-tert-butyl-pyridine-2-carbonitrile. The starting material can be prepared following published procedures (Z. R. Bell et al, Polyhedron, 20(15-16), 2045-2053, 2001).
MS (LC/MS, ES+): 191=[M+H]$^+$.
HPLC (Zorbax SB-C18, 3×30 mm, 1.8 μm, 10-100% MeCN (3.25 min), 100% MeCN (0.75 min)) retention time: 2.35 min.
$^1$H-NMR (400 MHz, CDCl$_3$): 8.43 (d, 1H), 7.41 (s, 1H), 7.10 (dd, 1H), 2.13 (br s, 2H), 1.41-1.27 (m, 2H), 1.35 (s, 9H), 1.16-1.13 (m, 2H).

Building block D4:
1-(4-Isopropyl-pyridin-2-yl)-cyclopropylamine

The product is obtained by an analogous reaction sequence as for building block D3, starting from 4-isopropyl-pyridine-2-carbonitrile. The starting material can be prepared following published procedures (WO2006074950).
Rf: (DCM/MeOH/NH$_3$ 90/9/1): 0.55
MS (LC/MS): 177=[M+H]$^+$
$^1$H-NMR (400 MHz, DMSO-d$_6$): 8.23 (d, 1H), 7.61 (d, 1H), 6.95 (dd, 1H), 2.19-2.80 (m, 1H), 1.21 (d, 6H), 1.17 (q, 2H), 0.91 (q, 2H).

Building block D5: 1-[5-(2,2-Dimethyl-propyl)-isoxazol-3-yl]-cyclopropylamine a) (Z)-2-Hydroxy-6,6-dimethyl-4-oxo-hept-2-enoic acid ethyl ester To an ice-cooled solution of sodium ethanolate (128.5 g, 1.79 mol) in EtOH (2500 ml) under nitrogen atmosphere is added 4,4-dimethyl-pentan-2-one (195.0 g, 1.71 mol). Half an hour later, oxalic acid diethyl ester (231.5 g, 1.71 mol) is added. After being stirred at rt for 24 h, the reaction mixture is diluted with water, and acidified to pH 2.0 by 6N aq hydrochloric acid. The mixture is contracted to about 1 L and extracted with DCM. The combined extracts are washed with brine, dried over sodium sulfate, and concentrated in vacuo to yield the product as a brown liquid.
MS (LC/MS): 215=[M+H]$^+$
$^1$H-NMR (300 MHz, CDCl$_3$): 6.32 (s, 1H), 4.35 (q, 2H), 2.33 (s, 2H), 1.60 (t, 3H), 1.04 (s, 9H).

b) 5-(2,2-Dimethyl-propyl)-isoxazole-3-carboxylic acid

To a solution of (Z)-2-hydroxy-6,6-dimethyl-4-oxo-hept-2-enoic acid ethyl ester (298.5 g, 1.39 mol) in EtOH (1600 ml) is added hydroxylamine hydrochloride (106.5 g, 1.53 mol) and the resulting solution is stirred at room temperature for 24 h. 2N aq sodium hydroxide (1740 ml, 3.48 mol) is added to the reaction and the resulting solution is stirred at rt for 2 h. The reaction mixture is acidified with 6N aq hydrochloric acid, concentrated to about 3 L, and extracted with EtOAc (2000 ml). The combined organic layers are washed with brine, dried over magnesium sulfate and concentrated. The resulting solid is washed with ether and dried to afford the product.
$^1$H-NMR (300 MHz, DMSO-d$_6$): 6.61 (s, 1H), 2.72 (s, 2H), 0.94 (s, 9H).

c) 5-(2,2-Dimethyl-propyl)-isoxazole-3-carboxylic acid tert-butylamide

To a solution of 5-(2,2-dimethyl-propyl)-isoxazole-3-carboxylic acid (125.4 g, 0.685 mol) in THF (1500 ml) and MeCN (1500 ml) is added HOBT (101.75 g, 0.753 mol) and EDCI (144.3 g, 0.753 mol). After stirred 30 min, tert-butyl amine (86.7 ml, 0.821 mol) is added dropwise under nitrogen atmosphere and then the reaction is stirred at rt for 1.5 h. The solvents are evaporated under reduced pressure and the residue is taken into DCM (2000 ml). The mixture is washed with saturated aq sodium bicarbonate (500 ml×2), the organic layer is dried over sodium sulfate and concentrated. The residue is purified by chromatography on silica (DCM) to give the product as white solid.
MS (LC/MS): 239=[M+H]$^+$ d) 5-(2,2-Dimethyl-propyl)-isoxazole-3-carbonitrile A mixture of 5-(2,2-dimethyl-propyl)-isoxazole-3-carboxylic acid tert-butylamide (58.0 g, 0.243 mol) and phosphorus (III) oxychloride (156 ml, 1.70 mol) is heated under nitrogen atmosphere at reflux temperature for 2 h. The reaction mixture is cooled to rt and concentrated to remove excess phosphorus (III) oxychloride. The residue is diluted with DCM (2000 ml) and washed with saturated aq sodium bicarbonate (500 ml×2). The organic layer is washed with brine, dried over sodium sulfate, and concentrated. The residue is purified by chromatography on silica (DCM/hexanes 1/1) to yield the target compound as yellow liquid.
$^1$H-NMR (300 MHz, CDCl$_3$): 6.36 (s, 1H), 2.74 (s, 2H), 1.00 (s, 9H).

e) 1-[5-(2,2-Dimethyl-propyl)-isoxazol-3-yl]-cyclopropylamine

To a mixture of 5 g (30.4 mmol) of 5-(2,2-dimethyl-propyl)-isoxazole-3-carbonitrile and 10.1 ml (34.1 mmol) of titanium(IV) isopropoxide in 150 ml of dry diethyl ether a solution of 22 ml of ethylmagnesium bromide (3 M in diethyl ether, 66.0 mmol) is added at −70° C. The reaction mixture is allowed to reach rt within two hours, 7.6 ml (60.6 mmol) of boron trifluoride-diethyl etherate are added and stirring is continued for one hour. After addition of 90 ml of 1M aq hydrochloric acid and 450 ml of diethyl ether two clear phases are obtained which are treated with 300 ml of 10% aq sodium hydroxide. The aqueous phase is extracted with diethyl ether, the combined organic phases are dried over sodium sulfate and evaporated to afford a dark orange oil. After filtration over a C18-bond elut column (Varian) with THF/MeCN the oil is purified by HPLC (dissolved in 6 ml of tetrahydrofuran, 25 injections, XBridge C18 column, 19×150 mm, 5 μM, gradient of 95% MeCN in water to 10% MeCN in water, containing 0.02% of ammonium hydroxide). The combined product fractions are concentrated and the product is extracted with DCM to yield the product as an orange solid.
m.p. 39-47° C.
MS (ES+): 195=[M+H]$^+$.
$^1$H-NMR (360 MHz, CDCl$_3$): 5.50 (s, 1H), 2.50 (s, 2H), 1.80 (br s, 2H), 1.10-1.05 (m, 2H), 0.95-0.90 (m, 2H), 0.90 (s, 9H).

Building block D6: 1-(3-Propyl-isoxazol-5-yl)-cyclopropylamine a) 3-Propyl-isoxazole-5-carboxylic acid

Sodium (4.42 g, 193 mmol, 1.05 eq) is added to 260 ml of EtOH at 0° C. within 45 min, followed by addition of 2-pentanone (15.8 g, 184 mmol, 1 eq) and diethyl oxalate. The reaction mixture is heated to 60° C. After 3 hours, the mixture is concentrated, and the residue is dissolved is acetic acid (350 ml) and heated to 55° C. Hydroxylamine hydrochloride (38.4 g) is dissolved in 150 ml water and added to the reaction mixture within 15 min. The reaction mixture is heated at 75° C. for 20 h. The mixture is concentrated, and the residue is diluted with DCM (400 ml). The organic layer dried over sodium sulfate and concentrated to give the product which can be used for the next step without purification.

MS (ES+): 156=[M+H]$^+$

HPLC (Zorbax SB-C18, 3×30 mm, 1.8 µm, 30-100% MeCN (3.25 min), 100% MeCN (0.75 min)) retention time=0.66 min b) 3-Propyl-isoxazole-5-carboxylic acid amide

3-Propyl-isoxazole-5-carboxylic acid (21 g, 135 mmol, 1 eq) is dissolved in 400 ml DCM. Thionyl chloride (40 ml) and DMF (1 ml) are added. The reaction is heated at reflux temperature for 150 min and then cooled to rt. The mixture is poured onto 90 ml of aq ammonia (25% in water) at 0° C., and 600 ml EtOAc are added. The organic layer is dried over sodium sulfate and concentrated. The product crystallizes from the solution of the residue in EtOAc and diisopropyl ether.

MS (ES+): 155=[M+H]$^+$

HPLC (Zorbax SB-C18, 3×30 mm, 1.8 µm, 30-100% MeCN (3.25 min), 100% MeCN (0.75 min)) retention time=0.47 min $^1$H-NMR (600 MHz, DMSO-d$_6$): 8.3 (s, 1H), 7.9 (s, 1H), 6.94 (s, 1H), 2.66-2.60 (m, 2H), 1.69-1.59 (m, 2H), 0.93-0.87 (m, 3H).

c) 3-Propyl-isoxazole-5-carbonitrile

3-Propyl-isoxazole-5-carboxylic acid amide (770 mg, 4.99 mmol, 1 eq) is dissolved in 6 ml of phosphorus (III) oxychloride and heated at 110° C. for 45 min. The reaction mixture is concentrated, the residue is dissolved in DCM, washed with aq sodium bicarbonate, filtered and concentrated to give the product.

HPLC (Nucleosil C18HD, 4×70 mm, 3 µm, 20-100% MeCN (6 min), 100% MeCN (1.5 min)) retention time=4.55 min $^1$H-NMR (400 MHz, DMSO-d$_6$): 6.80 (s, 1H), 2.72 (t, 2H), 1.81-1.69 (m, 2H), 1.01 (t, 3H).

d) 1-(3-Propyl-isoxazol-5-yl)-cyclopropylamine

3-Propyl-isoxazole-5-carbonitrile (3 g, 22 mmol, 1 eq) is dissolved in 15 ml diethyl ether. Titan-IV-isopropoxide (7.18 ml, 24.2 mmol, 1.1 eq) is added at rt, and the reaction is cooled to −65° C. Ethyl magnesium bromide (16 ml, 48 mmol, 2.2 eq) is added, and the reaction is warmed to rt within 2 hours. BF$_3$*Et$_2$O (11.4 ml, 90.3 mmol, 4.1 eq) is added at 0° C., and the reaction is stirred at 0° C. for 1 h. The reaction is quenched by addition of 1N aq hydrochloric acid (4.9 ml), followed by addition of 2N aq sodium hydroxide (11 ml). The mixture is diluted with TBME (80 ml) and water (50 ml). The organic layer is washed with brine, dried over sodium sulfate and concentrated. The residue is purified by chromatography on silica (EtOAc/hexane 95/5) to give the product.

MS (ES+): 167=[M+H]$^+$

HPLC (Nucleosil C18HD, 4×70 mm, 3 µm, 20-100% MeCN (6 min), 100% MeCN (1.5 min)) retention time=1.20 min

Building block E3: 3-(3-Methanesulfonyloxy-propoxy)-5-methoxymethyl-benzoic acid methyl ester a) 3-Allyloxy-5-hydroxymethyl-benzoic acid methyl ester

5-Allyloxy-isophtalic acid monomethyl ester (Fang et al., J. Am. Chem. Soc. 1998, 8543-8544) (6.14 g, 26 mmol, 1 eq) is dissolved in THF (200 ml). Et$_3$N (4.4 ml, 31.2 mmol, 1.2 eq) is added, and the reaction mixture is cooled to 0° C. Isopropyl chloroformate (1N in toluene, 36.4 ml, 36 mmol, 1.4 eq) is added, and the reaction is stirred for 1 h at 0° C. Water (50 ml) and TBME (300 ml) are added, and the organic layer is washed with aq sodium bicarbonate and brine, dried over sodium sulfate and concentrated. The residue is dissolved in THF (200 ml) at 0° C., and NaBH$_4$ (3.25 g, 85.9 mmol, 3.31 eq) are added in 25 ml of ice water within 10 min. The reaction is stirred for 1 hour at 0° C. 100 ml of water and 300 ml of TBME are added, the organic layer is washed with aq sodium bicarbonate and brine, dried over sodium sulfate, and concentrated. The product is used in the next step without further purification.

HPLC (Nucleosil C18HD, 4×70 mm, 3 µm, 20-100% MeCN (6 min), 100% MeCN (1.5 min)) retention time=3.76 min $^1$H-NMR (400 MHz, CDCl$_3$): 7.58 (s, 1H), 7.42 (s, 1H), 7.10 (s, 1H), 6.05-5.92 (m, 1H), 5.41-5.22 (m, 2H), 4.66 (s, 2H), 4.53 (d, 2H), 3.86 (s, 3H).

b) 3-Allyloxy-5-methoxymethyl-benzoic acid methyl ester

3-Allyloxy-5-hydroxymethyl-benzoic acid methyl ester (5.3 g, 23.8 mmol, 1 eq) is dissolved in DMF (60 ml). Sodium hydride (1.19 g, 29.8 mmol, 1.25 eq) is added at 0° C., and the reaction mixture is stirred for 30 min. MeI (3.32 ml, 35.8 mmol, 1.5 eq) is added, and the reaction mixture is stirred for 2 h at rt. 20 ml 1N aq hydrochloric acid and TBME (200 ml) are added, the organic layer is washed with brine, dried over sodium sulfate, and concentrated. The product is used in the next step without further purification.

HPLC (Nucleosil C18HD, 4×70 mm, 3 µm, 20-100% MeCN (6 min), 100% MeCN (1.5 min)) retention time=4.99 min $^1$H-NMR (400 MHz, CDCl$_3$): 7.52 (s, 1H), 7.42 (s, 1H), 7.05 (s, 1H), 6.05-5.92 (m, 1H), 5.40-5.19 (m, 2H), 4.55 (d, 2H), 4.40 (s, 2H), 3.85 (s, 3H), 3.32 (s, 3H).

c) 3-(3-Hydroxy-propoxy)-5-methoxymethyl-benzoic acid methyl ester

3-Allyloxy-5-methoxymethyl-benzoic acid methyl ester (2.00 g, 8.46 mmol, 1 eq) is dissolved in THF (60 ml). 9-BBN (0.5 N in THF, 48.7 ml, 24.4 mmol, 2.88 eq) is added at 0° C., and the reaction mixture is stirred for 20 h. H$_2$O$_2$ (30% in water, 55 ml) and aq sodium carbonate (4% in water, 184 ml) are added, and the reaction is stirred for 1 h. TBME (250 ml) is added, the organic layer is washed with brine, dried over sodium sulfate, and concentrated. The residue is purified by chromatography on silica (EtOAc/hexane 55/45) to give the product.

MS (ES+): 272 [M+NH$_4$]$^+$

HPLC (Nucleosil C18HD, 4×70 mm, 3 μm, 20-100% MeCN (6 min), 100% MeCN (1.5 min)) retention time=3.38 min d) 3-(3-Methanesulfonyloxy-propoxy)-5-methoxymethyl-benzoic acid methyl ester 3-(3-Hydroxy-propoxy)-5-methoxymethyl-benzoic acid methyl ester (508 mg, 2.00 mmol, 1 eq) is dissolved in THF (10 ml). Et$_3$N (334 μl, 2.4 mmol, 1.2 eq) and methansulfonyl chloride (170 μl, 2.2 mmol, 1.1 eq) are added, and the reaction is stirred for 22 h. Aq sodium bicarbonate (10 ml) and EtOAc (20 ml) are added, and the organic layer is washed with brine, dried over sodium sulfate, and concentrated. The residue is purified by chromatography on silica (EtOAc/hexane 1/1) to give the product.

MS (ES+): 350 [M+NH$_4$]$^+$

HPLC (Nucleosil C18HD, 4×70 mm, 3 μm, 20-100% MeCN (6 min), 100% MeCN (1.5 min)) retention time=4.26 min

The invention claimed is:

1. A compound of the formula

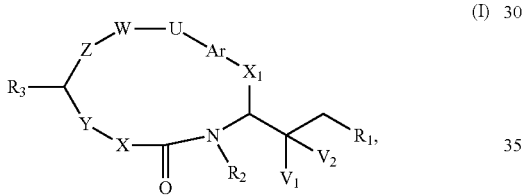

(I)

in which

R$_1$ is —(CH$_2$)$_k$N(R$_a$)R$_b$, in which
k is 0, 1 or 2;
R$_a$ is hydrogen or an optionally substituted (C$_{1-8}$)alkyl, (C$_{3-8}$)cycloalkyl, (C$_{3-8}$)cycloalkyl-(C$_{1-4}$)alkyl, aryl, aryl(C$_{1-4}$)alkyl, heteroaryl, heteroaryl(C$_{1-4}$)alkyl, chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydro-quinol-4-yl, 1,2,3,4-tetrahydro-isoquinol-4-yl, 1,2,3,4-tetrahydro-naphth-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl or 1,3,4,5-tetrahydro-benzo[c]oxepin-5-yl group; and
R$_b$ is a (C$_{3-8}$)cycloalkyl group, in which
(a) one of the carbon ring members of the (C$_{3-8}$) cycloalkyl moiety, which are different from the carbon ring member, to which the nitrogen atom carrying R$_a$ is attached, is optionally replaced by a hetero ring member, selected from the group consisting of —O—, —S—, —S(=O)—, —S(=O)$_2$— and —N(R$_c$)—, in which
R$_c$ is hydrogen or an optionally substituted (C$_{1-8}$) alkyl, (C$_{3-8}$)cycloalkyl, (C$_{3-8}$)cycloalkyl(C$_{1-4}$)alkyl, aryl, aryl(C$_{1-4}$)alkyl, heteroaryl or heteroaryl(C$_{1-4}$)alkyl group,
(b) the (C$_{3-8}$)cycloalkyl moiety is substituted by 1 to 4 substituents, independently selected from the group consisting of halogen, cyano, oxo, hydroxy, (C$_{1-4}$)-alkoxy, (C$_{1-4}$)alkoxy(C$_{1-4}$)alkoxy, (C$_{1-4}$)alkylthio, (C$_{1-4}$)alkylsulfinyl, (C$_{1-4}$)alkylsulfonyl, (C$_{1-4}$)alkylcarbonyl, (C$_{1-4}$)alkylcarbonyloxy, (C$_{1-4}$)alkoxycarbonyl, (C$_{1-4}$)alkoxycarbonyloxy and an optionally substituted (C$_{1-8}$)alkyl, (C$_{3-8}$)cycloalkyl, (C$_{3-8}$)cycloalkyl-(C$_{1-4}$)alkyl, aryl, aryl(C$_{1-4}$)alkyl, heteroaryl, heteroaryl(C$_{1-4}$)alkyl, non-aromatic heterocyclyl, non-aromatic heterocyclyl(C$_{1-4}$)alkyl, chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydro-quinol-4-yl, 1,2,3,4-tetrahydro-isoquinol-4-yl, 1,2,3,4-tetrahydro-naphth-1-yl, 1,1-dioxo-1,2,3,4-tetrahydro-1lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl or 1,3,4,5-tetrahydro-benzo[c]oxepin-5-yl group, and
(c) the (C$_{3-8}$)cycloalkyl moiety is optionally substituted at two adjacent carbon ring members by two substituents, which form, together with the two adjacent carbon ring members, to which they are attached, a (C$_{3-8}$)cycloalkyl group, in which
(i) one of the carbon ring members of the (C$_{3-8}$) cycloalkyl group thus formed, which are different from the said two adjacent carbon ring members, to which the said two substituents are optionally attached, is optionally replaced by a hetero ring member, selected from the group consisting of —O—, —S—, —S(=O)—, —S(=O)$_2$— and —N(R$_d$)—, in which R$_d$ is hydrogen or an optionally substituted (C$_{1-8}$) alkyl, (C$_{3-8}$)cycloalkyl, (C$_{3-8}$)cycloalkyl(C$_{1-4}$) alkyl, aryl, aryl(C$_{1-4}$)alkyl, heteroaryl or heteroaryl(C$_{1-4}$)alkyl group, and
(ii) the (C$_{3-8}$)cycloalkyl group thus formed is optionally substituted by 1 to 4 substituents, independently selected from the group consisting of halogen, cyano, oxo, hydroxy, (C$_{1-4}$) alkoxy, (C$_{1-4}$)alkoxy(C$_{1-4}$)alkoxy, (C$_{1-4}$)alkylthio, (C$_{1-4}$)alkylsulfinyl, (C$_{1-4}$)alkylsulfonyl, (C$_{1-4}$)alkylcarbonyl, (C$_{1-4}$)alkylcarbonyloxy, (C$_{1-4}$)alkoxycarbonyl, (C$_{1-4}$)alkoxycarbonyloxy and an optionally substituted (C$_{1-8}$)alkyl, (C$_{3-8}$)cycloalkyl, (C$_{3-8}$)cycloalkyl(C$_{1-4}$)alkyl, aryl, aryl(C$_{1-4}$)alkyl, heteroaryl, heteroaryl(C$_{1-4}$)alkyl, non-aromatic heterocyclyl, non-aromatic heterocyclyl(C$_{1-4}$)alkyl, chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydro-quinol-4-yl, 1,2,3,4-tetrahydro-isoquinol-4-yl, 1,2,3,4-tetrahydro-naphth-1-yl, 1,1-dioxo-1,2,3,4-tetrahydro-1 lambda*6*-benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]

oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl or 1,3,4,5-tetrahydro-benzo[c]oxepin-5-yl group;

$R_2$ is hydrogen or $(C_{1-4})$alkyl;

$R_3$ is hydrogen, $(C_{1-6})$alkyl or an optionally substituted $(C_{1-6})$alkylOC(=O)NH, $(C_{3-8})$cyclo-alkylOC(=O)NH, $(C_{3-8})$cycloalkyl$(C_{1-4})$alkylOC(=O)NH, aryl$(C_{1-4})$alkylOC(=O)NH, heteroaryl$(C_{1-4})$alkylOC(=O)NH, $(C_{1-4})$alkylC(=O)NH, $(C_{3-8})$cycloalkylC(=O)NH, arylC(=O)NH, aryl$(C_{1-4})$alkylC(=O)NH, heteroarylC(=O)NH or heteroaryl$(C_{1-4})$alkylC(=O)NH group;

Ar is a phenylene ring, which ring is optionally substituted with halogen, $(C_{1-4})$alkoxy, hydroxy or $(C_{1-4})$alkyl, whereby U and $X_1$ are in ortho- or meta-position to each other;

U is a bond, O, $CF_2$, $CF_2CF_2$, CHF, CHFCHF, cycloprop-1,2-ylene, $(C_{1-3})$alkylenoxy, $(C_{1-3})$alkylenamino, $(C_{1-8})$alkylene or $NR_e$, in which $R_e$ is hydrogen, $(C_{1-8})$alkyl or $(C_{3-8})$cycloalkyl;

either $V_1$ is hydrogen and $V_2$ is hydroxy or $V_1$ and $V_2$ together are oxo;

W is CH=CH, cycloprop-1,2-ylene, phen-1,2-ylene, $CH_2CH(OH)$, $CH(OH)CH_2$ or $CR_fR_fCR_fR_f$, in which each $R_f$, independently, is hydrogen, fluorine or $(C_{1-4})$alkyl;

X is an optionally substituted phenylene or pyridinyl ring, whereby Y and C(=O)$NR_2$ are in meta-position to each other;

$X_1$ is $CR_gR_g$, in which each $R_g$, independently, is hydrogen, fluorine or an optionally substituted $(C_{1-8})$alkyl, $(C_{1-4})$alkoxy$(C_{1-4})$alkyl, $(C_{3-8})$cycloalkyl or $(C_{3-8})$cycloalkyl$(C_{1-4})$alkyl group;

Y is O or NH; and

Z is O, $CH_2$, $CF_2$, CHF, cycloprop-1,2-ylene or a bond, the number of ring atoms included in the macrocyclic ring being 14, 15, 16 or 17, in free base form or in acid addition salt form;

wherein the optional substituents on alkyl, alkoxy or cycloalkyl groups or moieties are one to three groups, independently selected from hydroxy, hydroxy$(C_{1-4})$alkyl, $(C_{1-4})$alkoxy, $(C_{1-4})$alkoxy$(C_{1-4})$alkyl, $(C_{1-4})$alkoxy$(C_{1-4})$alkoxy, $(C_{1-4})$alkylthio, $(C_{1-4})$alkoxycarbonyl, $(C_{1-4})$-alkylcarbonyloxy, $(C_{1-4})$alkylcarbonyl, $(C_{1-4})$alkylsulfonyl, cyano, oxo and $(C_{3-8}$ cycloalkyl;

the optional substituents on chroman-4-yl, isochroman-4-yl, thiochroman-4-yl, isothiochroman-4-yl, 1,1-dioxo-1lambda*6*-thiochroman-4-yl, 2,2-dioxo-2lambda*6*-isothiochroman-4-yl, 1,2,3,4-tetrahydro-quinol-4-yl, 1,2,3,4-tetrahydro-isoquinol-4-yl, 1,2,3,4-tetrahydro-naphth-1-yl, 1,1-dioxo-1,2,3,4-tetrahydro-1lambda*6* -benzo[e][1,2]thiazin-4-yl, 2,2-dioxo-1,2,3,4-tetrahydro-2lambda*6*-benzo[c][1,2]thiazin-4-yl, 1,1-dioxo-3,4-dihydro-1H-1lambda*6*-benzo[c][1,2]oxathiin-4-yl, 2,2-dioxo-3,4-dihydro-2H-2lambda*6*-benzo[e][1,2]oxathiin-4-yl, 2,3,4,5-tetrahydro-benzo[b]oxepin-5-yl, 1,3,4,5-tetrahydro-benzo[c]oxepin-5-yl, non-aromatic heterocyclyl, aryl or heteroaryl rings or moieties are one to three groups independently selected from hydroxy, optionally substituted $(C_{1-8})$alkyl, optionally substituted $(C_{1-6})$alkoxy, $S(=O)_2(C_{1-4})$alkyl, $(C_{3-8})$cycloalkyl, $(C_{3-8})$cycloalkyl$(C_{1-4})$alkyl, cyano, nitro, trifluoromethyl, halogen, aryl, heteroaryl and optionally substituted carbamoyl;

an optionally substituted aryl or heteroaryl group may also carry, as optional substituents, one to three groups selected from benzyloxy, phenoxy, $S(=O)_2NH_2$, N(H)$S(=O)_2(C_{1-6})$alkyl, N[$(C_{1-6})$alkyl]$S(=O)_2(C_{1-6})$alkyl, 2-oxo-pyrrolidin-1-yl, 2,5-dioxa-cyclopent-1-yl, carboxy, $(C_{1-4})$alkoxycarbonyl, $(C_{1-4})$alkylcarbamoyl, $(C_{1-4})$alkylsulfonyl, $(C_{1-4})$alkylcarbonyloxy, $(C_{1-4})$alkylcarbonyl, hydroxy$(C_{1-4})$alkyl and optionally substituted amino;

optional substituents on amino groups can be one or two groups independently selected from $(C_{1-4})$alkyl, $(C_{1-4})$alkoxy$(C_{1-4})$alkyl, $(C_{1-4})$alkoxycarbonyl, aryl$(C_{1-4})$alkoxycarbonyl and heteroaryl$(C_{1-4})$alkoxycarbonyl;

optional substituents on carbamoyl can be one or two groups selected from $(C_{1-4})$alkyl and $(C_{1-4})$alkoxy$(C_{1-4})$alkyl;

aryl is naphthyl or phenyl;

a heteroaryl is an aromatic 5- or 6-membered ring, in which 1, 2 or 3 ring atoms are hetero atoms independently selected from O, N and S; and a non-aromatic heterocyclyl is a non-aromatic 5- or 6-membered ring, in which 1, 2 or 3 ring atoms are hetero atoms independently selected from O, N and S.

2. A pharmaceutical composition, comprising:

the compound as claimed in claim 1, in free base form or in pharmaceutically acceptable acid addition salt form, as active ingredient and a pharmaceutical carrier or diluent.

3. A compound according to claim 1, in free base form or in pharmaceutically acceptable acid addition salt form, selected from:

(S)-19-Acetyl-4-{(R)-1-hydroxy-2-[1-(3-isopropyl-phenyl)-cyclopropylamino]-ethyl}-11-oxa-3,16-diaza-tricyclo[15.3.1.1*6,10*]docosa-1(21),6,8,10(22),17,19-hexaen-2-one;

(S)-4-{(R)-1-Hydroxy-2-[1-(3-isopropyl-phenyl)-cyclopropylamino]-ethyl}-19-(2-oxo-propoxy)-11,16-dioxa-3-aza-tricyclo[15.3.1.1*6,10*]docosa-1(21),6,8,10(22),17,19-hexaen-2-one;

(S)-4-{(R)-1-Hydroxy-2-[1-(3-isopropyl-phenyl)-cyclopropylamino]-ethyl}-19-oxazol-2-yl-11-oxa-3,16-diaza-tricyclo[15.3.1.1*6,10*]docosa-1(21),6,8,10(22),17,19-hexaen-2-one;

(S)-4-{(R)-2-[3-tert-Butyl-phenyl)-cyclopropylamino]-1-hydroxy-ethyl}-2-oxo-11,16-dioxa-3-aza-tricyclo[15.3.1.1*6,10*]docosa-1(21),6,8,10(22),17,19-hexaene-19-carboxylic acid dimethylamide;

(S)-18-Acetyl-4-{(R)-1-hydroxy-2-[1-(3-isopropyl-phenyl)-cyclopropylamino]-ethyl}-15-oxa-3-aza-tricyclo[14.3.1.1*6,10*]henicosa-1(20),6,8,10(21),16,18-hexaen-2-one;

(S)-18-Acetyl-4-{(R)-1-hydroxy-2-[1-(3-isopropyl-phenyl)-cyclopropylamino]-ethyl}-3,15-diaza-tricyclo[14.3.1.1*6,10*]henicosa-1(20),6,8,10(21),16,18-hexaen-2-one;

(S)-4-{(R)-1-Hydroxy-2-[1-(3-isopropyl-phenyl)-cyclopropylamino]-ethyl}-18-methoxymethyl-3,15,17-triaza-tricyclo[14.3.1.1*6,10*]henicosa-1(20),6,8,10(21),16,18-hexaen-2-one;

(S)-4-{(R)-1-Hydroxy-2-[1-(3-isopropyl-phenyl)-cyclopropylamino]-ethyl}-19-methoxymethyl-11-oxa-3,16-diaza-tricyclo[15.3.1.1*6,10*]docosa-1(21),6,8,10(22),17,19-hexaen-2-one;

(S)-4-{(R)-1-Hydroxy-2-[1-(3-isopropyl-phenyl)-cyclopropylamino]-ethyl}-19-methyl-11-oxa-3,16,18-triaza-tricyclo[15.3.1.1*6,10*]docosa-1(21),6,8,10(22),17,19-hexaen-2-one;

(S)-19-Acetyl-4-{(R)-1-hydroxy-2-[1-(3-isopropyl-phenyl)-cyclopropylamino]-ethyl}-11,16-dioxa-3-aza-tricyclo[15.3.1.1*6,10*]docosa-1(21),6,8,10(22),17,19-hexaen-2-one;

(S)-4-{(R)-1-Hydroxy-2-[1-(3-isopropyl-phenyl)-cyclopropylamino]-ethyl}-19-methoxymethyl-11-oxa-3,16,18-triaza-tricyclo[15.3.1.1*6,10*]docosa-1(21),6,8,10(22), 17,19-hexaen-2-one;

(S)-4-{(R)-1-Hydroxy-2-[1-(3-isopropyl-phenyl)-cyclopropylamino]-ethyl}-18-methoxymethyl-3,15-diaza-tricyclo[14.3.1.1*6,10*]henicosa-1(20),6,8,10(21),16,18-hexaen-2-one;

(S)-4-{(R)-1-Hydroxy-2-[1-(3-isopropyl-phenyl)-cyclopropylamino]-ethyl}-18-(2-oxo-propoxy)-15-oxa-3-aza-tricyclo[14.3.1.1*6,10*]henicosa-1(20),6,8,10(21),16,18-hexaen-2-one;

(S)-4-{(R)-1-Hydroxy-2-[1-(3-isopropyl-phenyl)-cyclopropylamino]-ethyl}-18-oxazol-2-yl-3,15-diaza-tricyclo[14.3.1.1*6,10*]henicosa-1(20),6,8,10(21),16,18-hexaen-2-one;

(S)-4-{(R)-2-[1-(3-tert-Butyl-phenyl)-cyclopropylamino]-1-hydroxy-ethyl}-19-methoxymethyl-11-oxa-3,16-diaza-tricyclo[15.3.1.1*6,10*]docosa-1(21),6,8,10(22),17,19-hexaen-2-one;

(S)-4-{(R)-2-[1-(3-tert-Butyl-phenyl)-cyclopropylamino]-1-hydroxy-ethyl}-19-methoxymethyl-11-oxa-3,16,18-triaza-tricyclo[15.3.1.1*6,10*]docosa-1(21),6,8,10(22), 17,19-hexaen-2-one;

(S)-4-{(R)-2-[1-(3-tert-Butyl-phenyl)-cyclopropylamino]-1-hydroxy-ethyl}-19-(2-oxo-propoxy)-11,16-dioxa-3-aza-tricyclo[15.3.1.1*6,10*]docosa-1(21),6,8,10(22), 17,19-hexaen-2-one;

(S)-4-{(R)-2-[1-(3-tert-Butyl-phenyl)-cyclopropylamino]-1-hydroxy-ethyl}-19-oxazol-2-yl-11-oxa-3,16-diaza-tricyclo[15.3.1.1*6,10*]docosa-1(21),6,8,10(22),17,19-hexaen-2-one;

(S)-4-{(R)-2-[1-(4-tert-Butyl-pyridin-2-yl)-cyclopropylamino]-1-hydroxy-ethyl}-18-(2-oxo-propoxy)-15-oxa-3-aza-tricyclo[14.3.1.1*6,10*]henicosa-1(19),6,8,10(21),16(20),17-hexaen-2-one;

(S)-4-{(R)-2-[1-(4-tert-Butyl-pyridin-2-yl)-cyclopropylamino]-1-hydroxy-ethyl}-18-oxazol-2-yl-3,15-diaza-tricyclo[14.3.1.1*6,10*]henicosa-1(19),6,8,10(21),16(20), 17-hexaen-2-one;

Propane-1-sulfonic acid ((S)-4-{(R)-1-hydroxy-2-[1-(3-isopropyl-phenyl)-cyclopropylamino]-ethyl}-2-oxo-11-oxa-3,16-diaza-tricyclo[15.3.1.1*6,10*]docosa-1(21),6,8,10(22),17,19-hexaen-19-yl)-methyl-amide;

(S)-19-Acetyl-4-{(R)-2-[1-(3-tert-butyl-phenyl)-cyclopropylamino]-1-hydroxy-ethyl}-11,16-dioxa-3-aza-tricyclo[15.3.1.1*6,10*]docosa-1(21),6,8,10(22),17,19-hexaen-2-one;

Propane-1-sulfonic acid((S)-4-{(R)-1-hydroxy-2-[1-(3-isopropyl-phenyl)-cyclopropylamino]-ethyl}-2-oxo-11,16-dioxa-3-aza-tricyclo[15.3.1.1*6,10*]docosa-1(21),6,8,10(22),17,19-hexaen-19-yl)-methyl-amide;

(S)-4-{(R)-2-[1-(4-tert-Butyl-pyridin-2-yl)-cyclopropylamino]-1-hydroxy-ethyl}-19-methyl-11,16-dioxa-3,18-diaza-tricyclo[15.3.1.1*6,10*]docosa-1(21),6,8,10(22),17,19-hexaen-2-one;

(S)-4-{(R)-1-Hydroxy-2-[1-(3-isopropyl-phenyl)-cyclopropylamino]-ethyl}-2-oxo-11-oxa-3,16-diaza-tricyclo[15.3.1.1*6,10*]docosa-1(21),6,8,10(22),17,19-hexaene-19-carboxylic acid dimethylamide;

(S)-4-{(R)-1-Hydroxy-2-[1-(3-isopropyl-phenyl)-cyclopropylamino]-ethyl}-19-methoxy-11-oxa-3,16-diaza-tricyclo[15.3.1.1*6,10*]docosa-1(21),6,8,10(22),17,19-hexaen-2-one;

(S)-4-{(R)-1-Hydroxy-2-[1-(3-isopropyl-phenyl)-cyclopropylamino]-ethyl}-19-(2-oxo-propoxy)-11-oxa-3,16-diaza-tricyclo[15.3.1.1*6,10*]docosa-(21),6,8,10(22),17,19-hexaen-2-one;

(S)-19-Acetyl-4-{(R)-2-[1-(3-tert-butyl-phenyl)-cyclopropylamino]-1-hydroxy-ethyl}-11-oxa-3,16-diaza-tricyclo[15.3.1.1*6,10*]docosa-1(21),6,8,10(22),17,19-hexaen-2-one;

(S)-4-{(R)-1-Hydroxy-2-[1-(3-isopropyl-phenyl)-cyclopropylamino]-ethyl}-18-methoxymethyl-11,15-dioxa-3-aza-tricyclo[14.3.1.1*6,10*]henicosa-1(20),6,8,10(21),16,18-hexaen-2-one;

(S)-4-{(R)-1-Hydroxy-2-[1-(3-isopropyl-phenyl)-cyclopropylamino]-ethyl}-19-methoxymethyl-11,16-dioxa-3,18-diaza-tricyclo[15.3.1.1*6,10*]docosa-1(21),6,8,10(22),17,19-hexaen-2-one;

(S)-4-{(R)-2-{1-[5-(2,2-Dimethyl-propyl)-isoxazol-3-yl]-cyclopropylamino}-ethyl}-1-hydroxy-ethyl)-19-methoxymethyl-11-oxa-3,16-diaza-tricyclo[15.3.1.1*6,10*]docosa-1(21),6,8,10(22),17,19-hexaen-2-one;

(S)-4-{(R)-1-Hydroxy-2-[1-(4-isopropyl-pyridin-2-yl)-cyclopropylamino]-ethyl}-18-methoxymethyl-3,15,17-triaza-tricyclo[14.3.1.1*6,10*]henicosa-1(20),6,8,10(21),16,18-hexaen-2-one;

(S)-4-{(R)-1-Hydroxy-2-[1-(4-isopropyl-pyridin-2-yl)-cyclopropylamino]-ethyl}-19-methoxymethyl-11-oxa-3,16,18-triaza-tricyclo[15.3.1.1*6,10*]docosa-1(21),6,8,10(22),17,19-hexaen-2-one;

(S)-18-Acetyl-4-{(R)-2-[1-(4-tert-butyl-pyridin-2-yl)-cyclopropylamino]-1-hydroxy-ethyl}-3,15-diaza-tricyclo[14.3.1.1*6,10*]henicosa-1(20),6,8,10(21),16,18-hexaen-2-one;

(S)-4-[(R)-1-Hydroxy-2-(2-phenyl-cyclopropylamino)-ethyl]-19-methoxymethyl-11-oxa-3,16-diaza-tricyclo[15.3.1.1*6,10*]docosa-1(21),6,8,10(22),17,19-hexaen-2-one;

(S)-4-{(R)-1-Hydroxy-2-[1-(3-propyl-isoxazol-5-yl)-cyclopropylamino]-ethyl}-19-methoxymethyl-11-oxa-3,16-diaza-tricyclo[15.3.1.1*6,10*]docosa-1(21),6,8,10(22),17,19-hexaen-2-one;

(S)-19-Acetyl-4-{(R)-2-[1-(4-tert-butyl-pyridin-2-yl)-cyclopropylamino]-1-hydroxy-ethyl}-11-oxa-3,16-diaza-tricyclo[15.3.1.1*6,10*]docosa-1(21),6,8,10(22),17,19-hexaen-2-one;

(S)-4-{(R)-2-[1-(4-tert-Butyl-pyridin-2-yl)-cyclopropylamino]-1-hydroxy-ethyl}-19-methoxy-11-oxa-3,16-diaza-tricyclo[15.3.1.1*6,10*]docosa-1(21),6,8,10(22),17,19-hexaen-2-one;

(E)-(S)-4-{(R)-2-[1-(3-tert-Butyl-phenyl)-cyclopropylamino]-1-hydroxy-ethyl}-9-fluoro-19-methyl-11-oxa-3,16,18-triaza-tricyclo[15.3.1.1*6,10*]docosa-1(21),6,8,10(22),13,17,19-heptaen-2-one;

(E)-(S)-4-{(R)-2-[1-(3-tert-Butyl-phenyl)-cyclopropylamino]-1-hydroxy-ethyl}-9-fluoro-2-oxo-11-oxa-3,16-diaza-tricyclo[15.3.1.1*6,10*]docosa-1(21),6,8,10(22),13,17,19-heptaene-19-carboxylic acid dimethylamide;

(S)-4-{(R)-1-Hydroxy-2-[1-(3-isopropyl-phenyl)-cyclo-propylamino]-ethyl}-18-methoxy-3,15,17-triaza-tricyclo[14.3.1.1*6,10*]henicosa-1(19),6,8,10(21),16(20),17-hexaen-2-one;

(S)-4-{(R)-2-[1-(3-tert-Butyl-phenyl)-cyclopropylamino]-1-hydroxy-ethyl}-19-methyl-11-oxa-3,16,18-triaza-tricyclo[15.3.1.1*6,10*]docosa-1(21),6,8,10(22),17,19-hexaen-2-one;

13,14-Benzo-(S)-4-{(R)-1-Hydroxy-2-[1-(3-isopropyl-phenyl)-cyclo-propylamino]-ethyl}-19-methyl-11,16-dioxa-3,18-diaza-tricyclo[15.3.1.1*6,10*]docosa-1(21),6,8,10(22),17,19-hexaen-2-one;

(S)-19-[1,3]Dioxolan-2-yl-4-{(R)-1-hydroxy-2-[1-(3-isopropyl-phenyl)-cyclopropylamino]-ethyl}-11-oxa-3,16-diaza-tricyclo[15.3.1.1*6,10*]docosa-1(21),6,8,10(22),17,19-hexaen-2-one;

(S)-4-{(R)-1-Hydroxy-2-[1-(3-isopropyl-phenyl)-cyclopropylamino]-ethyl}-19-thiazol-2-yl-11-oxa-3,16-diaza-tricyclo[15.3.1.1*6,10*]docosa-1(20),6,8,10(22),17(21),18-hexaen-2-one;

(S)-4-{(R)-1-Hydroxy-2-[1-(3-isopropyl-phenyl)-cyclopropylamino]-ethyl}-19-(2-oxo-pyrrolidin-1-yl)-11-oxa-3,16-diaza-tricyclo[15.3.1.1*6,10*]docosa-1(21),6,8,10(22),17,19-hexaen-2-one;

(S)-8-Fluoro-4-{(R)-1-hydroxy-2-[1-(3-isopropyl-phenyl)-cyclopropylamino]-ethyl}-19-methoxymethyl-11-oxa-3,16-diaza-tricyclo[15.3.1.1*6,10*]docosa-1(21),6,8,10(22),17,19-hexaen-2-one;

(S)-18-Chloro-4-{(R)-1-hydroxy-2-[1-(4-isopropyl-pyridin-2-yl)-cyclopropylamino]-ethyl}-3,15,17-triaza-tricyclo[14.3.1.1*6,10*]henicosa-1(20),6,8,10(21),16,18-hexaen-2-one;

(S)-19-Chloro-4-{(R)-1-hydroxy-2-[1-(4-isopropyl-pyridin-2-yl)-cyclopropylamino]-ethyl}-11-oxa-3,16,18-triaza-tricyclo[15.3.1.1*6,10*]docosa-1(21),6,8,10(22),17,19-hexaen-2-one;

(S)-4-{(R)-1-Hydroxy-2-[1-(3-isopropyl-phenyl)-cyclopropylamino]-ethyl}-19-methyl-11,16-dioxa-3,18-diaza-tricyclo[15.3.1.1*6,10*]docosa-1(21),6,8,10(22),17,19-hexaen-2-one;

(S)-4-{(R)-1-Hydroxy-2-[1-(3-isopropyl-phenyl)-cyclopropylamino]-ethyl}-19-(2-oxo-pyrrolidin-1-yl)-11,16-dioxa-3-aza-tricyclo[15.3.1.1*6,10*]docosa-1(21),6,8,10(22),17,19-hexaen-2-one;

(S)-4-{(R)-2-[1-(4-tert-Butyl-pyridin-2-yl)-cyclopropylamino]-1-hydroxy-ethyl}-18-methyl-3,15,17-triaza-tricyclo[14.3.1.1*6,10*]henicosa-1(19),6,8,10(21),16(20),17-hexaen-2-one;

(S)-4-{(R)-2-[1-(4-tert-Butyl-pyridin-2-yl)-cyclopropylamino]-1-hydroxy-ethyl}-19-methyl-11-oxa-3,16,18-triaza-tricyclo[15.3.1.1*6,10*]docosa-1(21),6,8,10(22),17,19-hexaen-2-one;

(S)-4-{(R)-1-Hydroxy-2-[1-(4-isopropyl-pyridin-2-yl)-cyclopropylamino]-ethyl}-18-methoxymethyl-3,15-diaza-tricyclo[14.3.1.1*6,10*]henicosa-1(19),6,8,10(21),16(20),17-hexaen-2-one;

(S)-4-{(R)-2-[1-(4-tert-Butyl-pyridin-2-yl)-cyclopropylamino]-1-hydroxy-ethyl}-18-methoxymethyl-3,15-diaza-tricyclo[14.3.1.1*6,10*]henicosa-1(19),6,8,10(21),16(20),17-hexaen-2-one;

(S)-4-{(R)-1-Hydroxy-2-[1-(4-isopropyl-pyridin-2-yl)-cyclopropylamino]-ethyl}-19-methoxymethyl-11-oxa-3,16-diaza-tricyclo[15.3.1.1*6,10*]docosa-1(21),6,8,10(22),17,19-hexaen-2-one;

(S)-4-{(R)-2-[1-(4-tert-Butyl-pyridin-2-yl)-cyclopropylamino]-1-hydroxy-ethyl}-19-methoxymethyl-11-oxa-3,16-diaza-tricyclo[15.3.1.1*6,10*]docosa-1(21),6,8,10(22),17,19-hexaen-2-one;

(S)-4-{(R)-2-[1-(4-tert-Butyl-pyridin-2-yl)-cyclopropylamino]-1-hydroxy-ethyl}-19-oxazol-2-yl-11-oxa-3,16-diaza-tricyclo[15.3.1.1*6,10*]docosa-1(20),6,8,10(22),17(21),18-hexaen-2-one;

(S)-4-{(R)-2-[1-(4-tert-Butyl-pyridin-2-yl)-cyclopropylamino]-1-hydroxy-ethyl}-19-(2-oxo-propoxy)-11,16-dioxa-3-aza-tricyclo[15.3.1.1*6,10*]docosa-1(20),6,8,10(22),17(21),18-hexaen-2-one; and (S)-4-((R)-1-Hydroxy-2-{1-[3-(1-hydroxy-1-methyl-ethyl)-phenyl]-cyclopropylamino}-ethyl)-19-methoxymethyl-11-oxa-3,16-diaza-tricyclo[15.3.1.1*6,10*]docosa-1(21),6,8,10(22),17,19-hexaen-2-one.

\* \* \* \* \*